·

US008512696B2

(12) United States Patent  
Anversa et al.

(10) Patent No.: US 8,512,696 B2  
(45) Date of Patent: Aug. 20, 2013

(54) METHODS OF ISOLATING NON-SENESCENT CARDIAC STEM CELLS AND USES THEREOF

(75) Inventors: Piero Anversa, Boston, MA (US); Annarosa Leri, Boston, MA (US); Jan Kajstura, Brookline, MA (US)

(73) Assignee: Autologous, LLC, New York, NY (US)

( * ) Notice: Subject to any disclaimer, the term of this patent is extended or adjusted under 35 U.S.C. 154(b) by 246 days.

(21) Appl. No.: 12/938,159

(22) Filed: Nov. 2, 2010

(65) Prior Publication Data

US 2011/0123500 A1   May 26, 2011

Related U.S. Application Data

(63) Continuation-in-part of application No. 12/324,031, filed on Nov. 26, 2008.

(60) Provisional application No. 60/991,637, filed on Nov. 30, 2007, provisional application No. 61/057,049, filed on May 29, 2008.

(51) Int. Cl.
*C12N 5/00* (2006.01)

(52) U.S. Cl.
USPC .......................................... 424/93.7; 435/325

(58) Field of Classification Search
None
See application file for complete search history.

(56) References Cited

U.S. PATENT DOCUMENTS

| 5,434,134 | A | 7/1995 | Gluckman et al. |
| 5,824,696 | A | 10/1998 | Griswold et al. |
| 5,908,782 | A | 6/1999 | Marshak et al. |
| 6,036,972 | A | 3/2000 | Nakamura et al. |
| 6,087,386 | A | 7/2000 | Chen et al. |
| 6,258,357 | B1 | 7/2001 | Spaner |
| 6,258,634 | B1 | 7/2001 | Wang et al. |
| 6,387,369 | B1 | 5/2002 | Pittenger et al. |
| 6,767,738 | B1 | 7/2004 | Gage et al. |
| 2002/0146680 | A1 | 10/2002 | Rich |
| 2003/0054973 | A1 | 3/2003 | Anversa |
| 2003/0105015 | A1 | 6/2003 | Gilbertson et al. |
| 2004/0258669 | A1 | 12/2004 | Dzau et al. |
| 2005/0170506 | A1 | 8/2005 | Sayre et al. |
| 2006/0239983 | A1 | 10/2006 | Anversa |
| 2006/0263337 | A1 | 11/2006 | Maziarz et al. |
| 2007/0054397 | A1 | 3/2007 | Ott et al. |
| 2008/0219957 | A1 | 9/2008 | Lim et al. |
| 2009/0143296 | A1 | 6/2009 | Anversa |
| 2009/0148421 | A1 | 6/2009 | Anversa et al. |
| 2009/0157046 | A1 | 6/2009 | Anversa |
| 2009/0162329 | A1 | 6/2009 | Anversa et al. |
| 2009/0169525 | A1 | 7/2009 | Anversa et al. |
| 2009/0180998 | A1 | 7/2009 | Anversa et al. |
| 2010/0239538 | A9 | 9/2010 | Anversa et al. |

FOREIGN PATENT DOCUMENTS

| JP | 11-246433 | 9/1999 |
| WO | WO 92/11865 | 7/1992 |
| WO | WO 95/28174 | 10/1995 |
| WO | WO 99/45775 | 9/1999 |
| WO | WO 99/47163 A | 9/1999 |
| WO | WO 99/49015 A | 9/1999 |
| WO | WO 01/26694 | 4/2001 |
| WO | WO 01/34179 | 5/2001 |
| WO | WO 01/94420 | 12/2001 |
| WO | WO 02/13760 A | 2/2002 |
| WO | WO 03/033678 A | 4/2003 |
| WO | WO 03/103611 A | 12/2003 |
| WO | WO 2006/045331 A | 5/2006 |
| WO | WO 07/100530 A1 | 9/2007 |
| WO | WO 2008/058216 A | 5/2008 |
| WO | WO 2009/073518 A1 | 6/2009 |
| WO | WO 2009/073594 A | 6/2009 |

OTHER PUBLICATIONS

Shinin V et al. 2006. Asymmetric division and cosegregation of template DNA strands in adult muscle satellite cells. Nat Cell Biol 8: 677-687.*
Kajstura J et al. 2012. Tracking Chromatid Segregation to Identify Human Cardiac Stem Cells That Regenerate Extensively the Infarcted Myocardium. Circ Res 111: 894-906.*
Jackson et al., "Regeneration of ischemic cardiac muscle and vascular endothelium by adult stem cells," Journal of Clinical Investigation, vol. 107:1395-1402, 2001.
Oh et al., "Telomerase reverse transcriptase promotes cardiac muscle cell proliferation, hypertrophy, and survival," Proc. Natl. Acad. Sci. USA, vol. 98:10308-10313, 2001.
Forraz et al., "Characterization of a Lineage-Negative Stem-Progenitor Cell Population Optimized for Ex Vivo Expansion and Enriched for LTC-IC," Stem Cells, vol. 22: 100-108, 2004.
Svegliani-Baroni et al., "Insulin and Insulin-Like Growth Factor-1 Stimulate Proliferation and Type I Collagen Accumulation by Human Hepatic Stellate Cells: Differential Effects on Signal Transduction Pathways," Hepatology, vol. 29: 1743-1751, 1999.
Nakajima et al., "The angiotensin II type 2 (AT2) receptor antagonizes the growth effects of the AT1 receptor: Gain-of function study using gene transfer," Proc Natl Acad Sci USA, vol. 92: 10663-10667, 1995.
Morrison et al., "Telomerase activity in hematopoietic cells is associated with self-renewal potential," Immunity, vol. 5: 207-216, 1996.
Piacibello et al., "Proliferative senescence in hematopoietic stem cells during ex vivo expansion," Folia Histochem. Cytobiol., vol. 43: 197-202, 2005.
Copenheaver, International Search Report and Written Opinion for PCT/US2011/058949, mailed Feb. 10, 2012 (6 pages).
Torella et al., "Biological properties and regenerative potential, in vitro and in vivo, of human cardiac stem cells isolated from each of the four chambers of the adult human heart" Circulation, vol. 114, No. 18, suppl: 87, 2006.

(Continued)

*Primary Examiner* — Lora E Barnhart Driscoll
(74) *Attorney, Agent, or Firm* — Cooley LLP

(57) ABSTRACT

The invention describes the isolation and methods of use of a non-senescent pool of adult cardiac stem cells. In particular, a subset of adult cardiac stem cells with superior regenerative capacity is disclosed. Such cells were found to have immortal DNA. Compositions comprising the non-senescent stem cells are also described. In addition, the present invention provides methods for repairing aged myocardium or damaged myocardium using the isolated non-senescent adult cardiac stem cells.

21 Claims, 66 Drawing Sheets

(56) References Cited

OTHER PUBLICATIONS

Bearzi et al., "Human cardiac stem cells" Proc. Natl. Acad Sci. USA, vol. 104: 14068-14073, 2007.

Messina et al., "Isolation and expansion of adult cardiac stem cells from human and murine heart" Circulation Research, vol. 95: 911-921, 2004.

Linke et at., "Stem cells in the dog heart are self-renewing, clonogenic, and multipotent and regenerate infarcted myocardium, improving cardiac function" Proc. Natl. Acad. Sci. USA, vol. 102: 8966-8971, 2005.

Beltrami et al., "Adult cardiac stem cells are multipotent and support myocardial regeneration" Cell, vol. 114: 763-776, 2003.

Dawn et al., "Cardiac stem cells delivered intravasculary traverse the vessel barrier, regenerate infarcted myocardium, and improve cardiac function" Proc. Natl. Acad. Sci. USA, vol. 102: 3766-3771, 2005.

Urbanek et al., "Cardiac stem cells possess growth factor-receptor systems that after activation regenerate the infarcted myocardium, improving ventricular function and long-term survival" Circulation Research, vol. 97: 663-673, 2005.

Urbanek et al., "Myocardial regeneration by activation of multipotent cardiac stem cells in ischemic heart failure" Proc. Natl. Acad. Sci. USA, vol. 102: 8692-8697, 2005.

Urbanek et al., "Intense myocyte formation from cardiac stem cells in human cardiac hypertophy" Proc. Natl. Acad. Sci. USA, vol. 100: 10440-10445, 2003.

Anversa et al., "Life and death of cardiac stein cells—A paradigm shift in cardiac biology" Circulation, vol. 113: 1451-1463, 2006.

Sussman et al., "Myocardial aging and senescence: Where have the stem cells gone?" Annual Review of Physiology, vol. 66: 29-48, 2004.

Armandola, Written Opinion of International Search Authority for PCT/US08/084877, Apr. 2009.

Young et al., "Mesenchymal Stein Cells Reside Within the Connective Tissues of Many Organs." *Developmental Dynamics* 1995, vol. 202 pp. 137-144.

Nakamura et al., "Myocardial protection from ischemia/reperfusion injury by endogenous and exogenous HGF." *J. Clin. Invest.* 2000, vol. 106, pp. 1511-1519.

Yamamura et al., "IGF-I differentially regulates Bcl-xL and Bax and confers myocardial protection in the rat heart." *Am. J. Physiol. Heart Circ. Physiol.* 2001, vol. 280, pp. H1191-H1200.

Segers et al., "Stem-cell therapy for cardiac disease." *Nature* 2008, vol. 451, pp. 937-942.

Pêche et al., "Prolongation of Heart Allograft Survival by Immature Dendritic Cells Generated from Recipient Type Bone Marrow Progenitors", *American Journal of Transplantation*, Feb. 2005, vol. 5, No. 2, pp. 255-267.

Metcalfe et al., "Transplantation tolerance: gene expression profiles comparing allotolerance vs. allorejection", *International Immunopharmacology*, Jan. 2005, vol. 5, No. 1, pp. 33-39.

International Search Report Based on International Application No. PCT/US08/085108 (Apr. 28, 2009).

Orlic et al., "Mobilized bone marrow cells repair the infarcted heart, improving function and survival", Proc. Natl. Acad. Sci. USA, vol. 98: 10344-10349, 2001.

Beltrami et al., "Adult cardiac stem cells are multipotent and support myocardial regeneration", *Cell*, Sep. 19, 2003, 114(6):763-776.

International Search Report based on International Application PCT/US2008/085163 (Oct. 14, 2009).

Baba et al., "Flk 1+ cardiac stem/progenitor cells derived from embryonic stem cells improve cardiac function in a dilated cardiomyopathy mouse model",*Cardiovascular Research*, 2007, 76:119-131.

Leri et al., "Heart failure and regenerative cardiology", *Regenerative Medicine*, 2006, 1(2):153-159.

International Search Report based on International Application PCT/US2008/085158 (Jan. 11, 2010).

Bardelli et al., "Asymmetric Division of Human Cardiac Progenitor Cells Involves Immortal DNA Strand Cosegregation," *Circulation*, 2008, 118:S_421, Abstract 3422.

D'Amario et al., "Immortal DNA Strand and Human Cardiac Stem Cell Renewal," *Circulation*, 2009, 120:S595, Abstract 2112.

\* cited by examiner

Figure 21 A-B
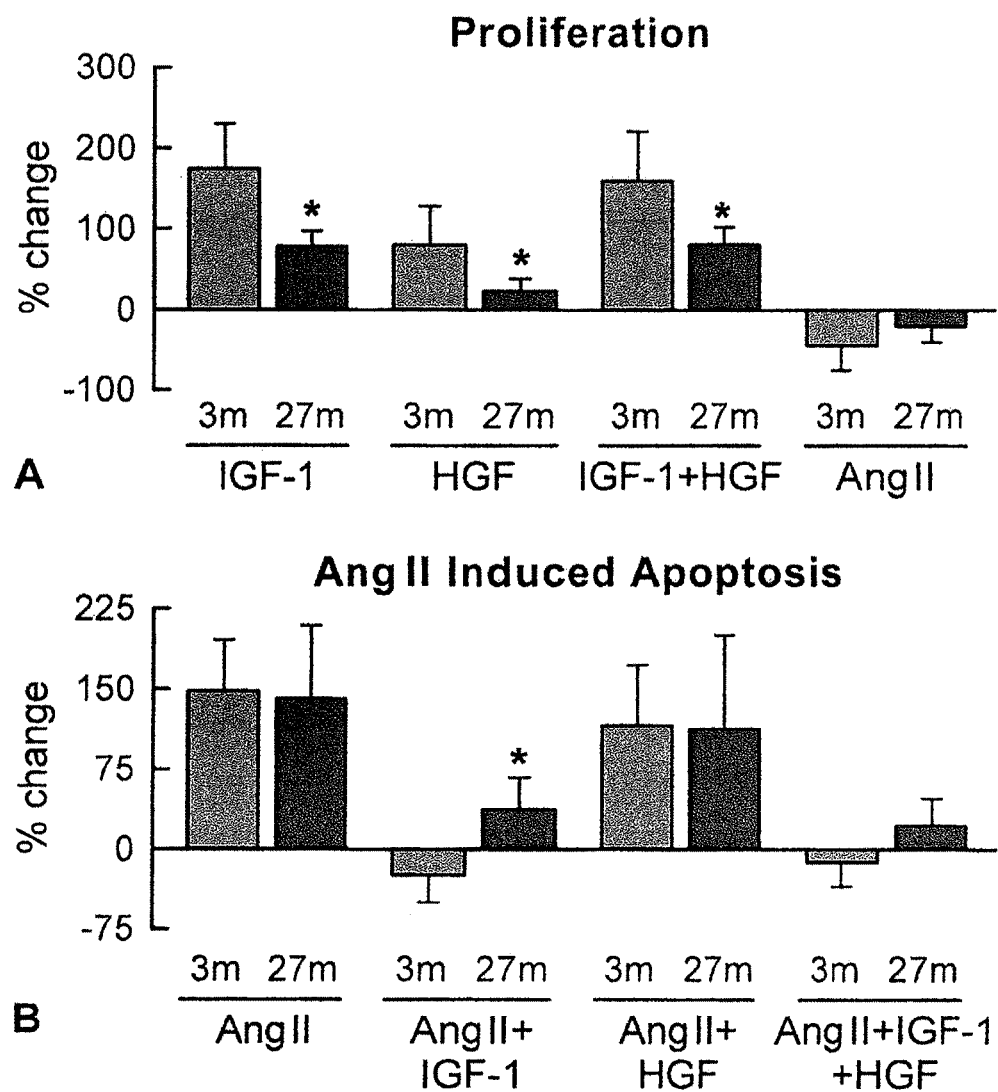

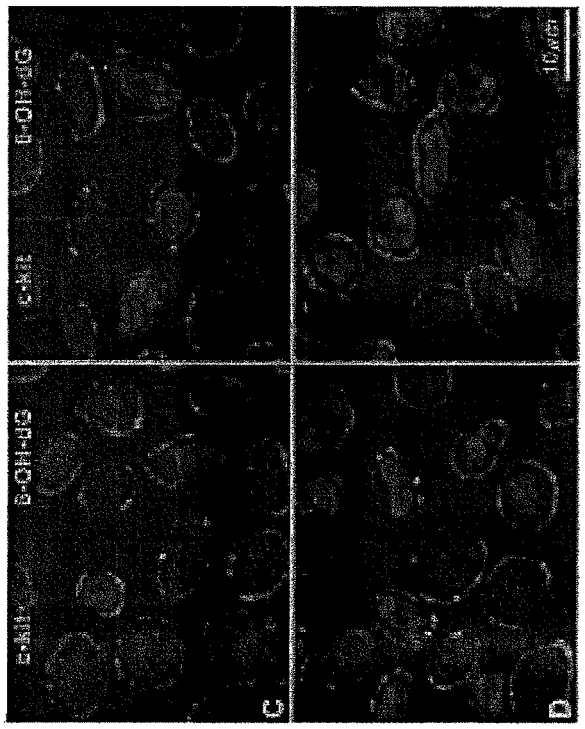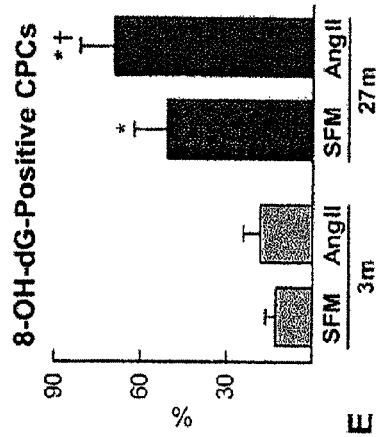
Figure 21C-E

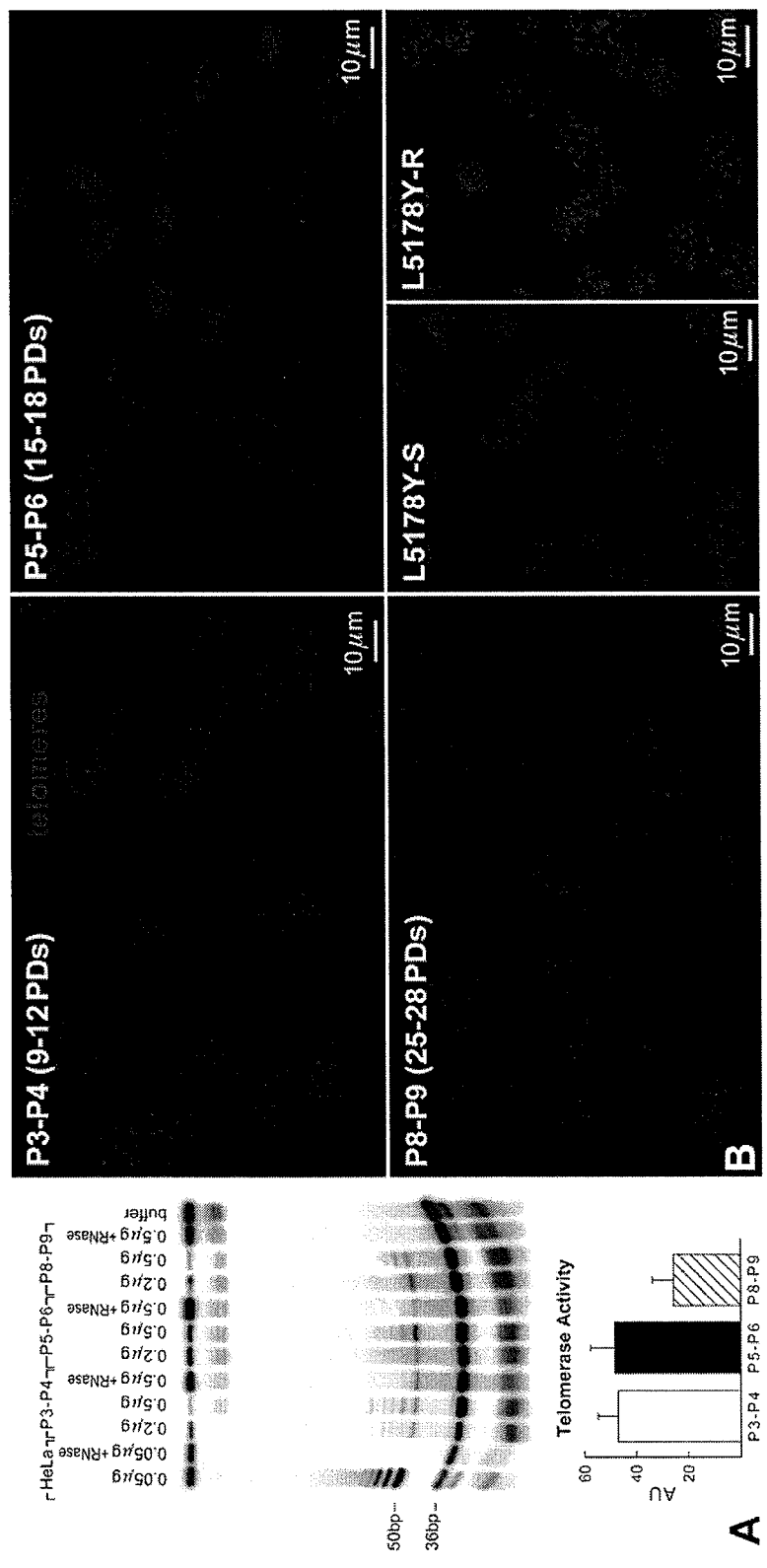
Figure 52 A-B

Figure 53 A-G
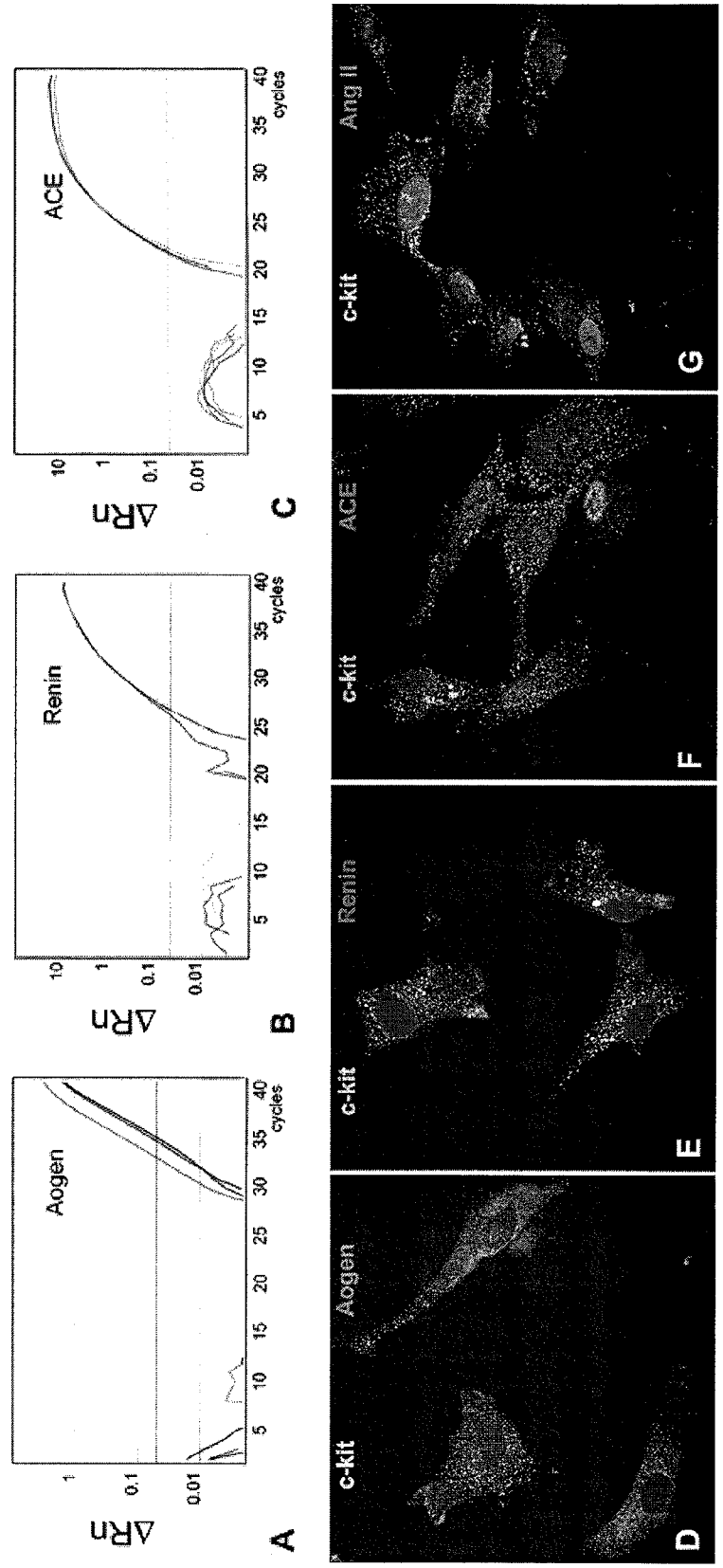

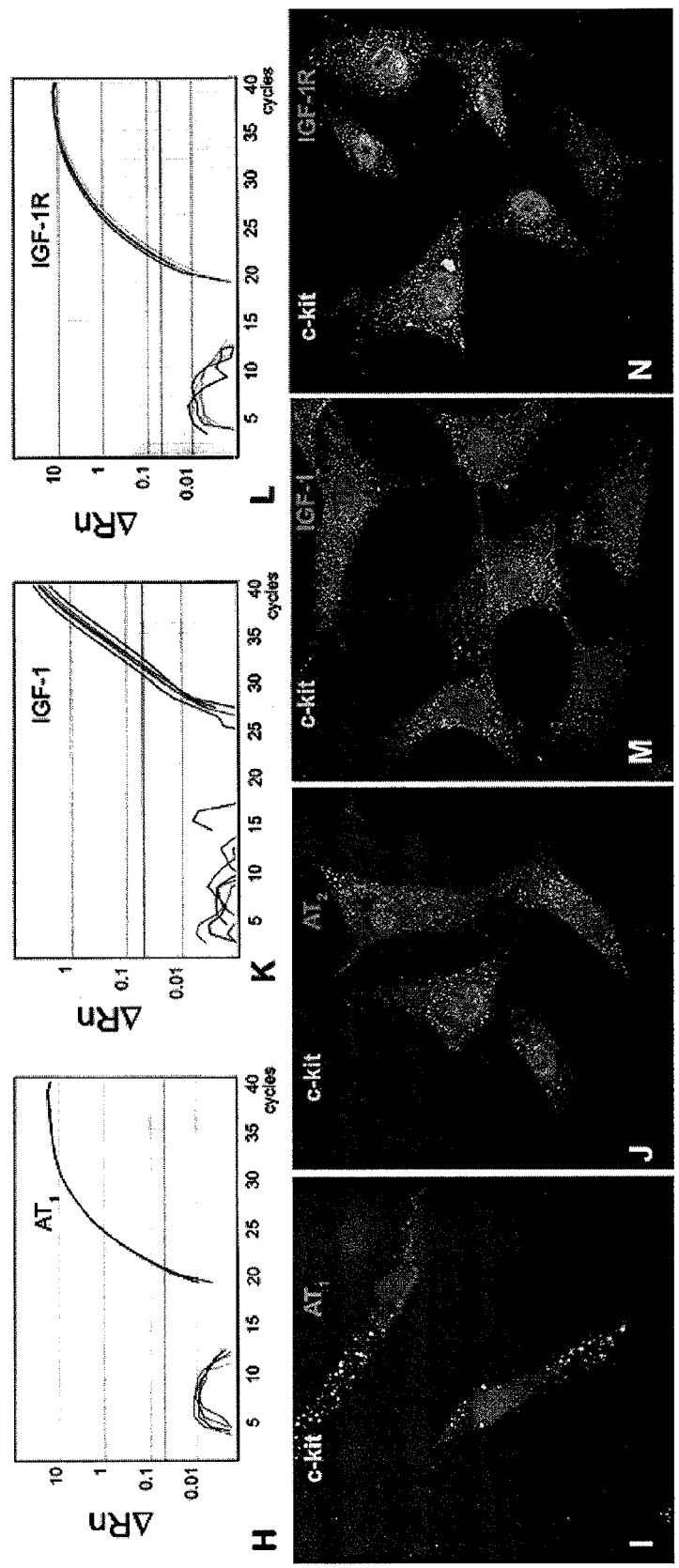
Figure 53 H-N

Figure 54
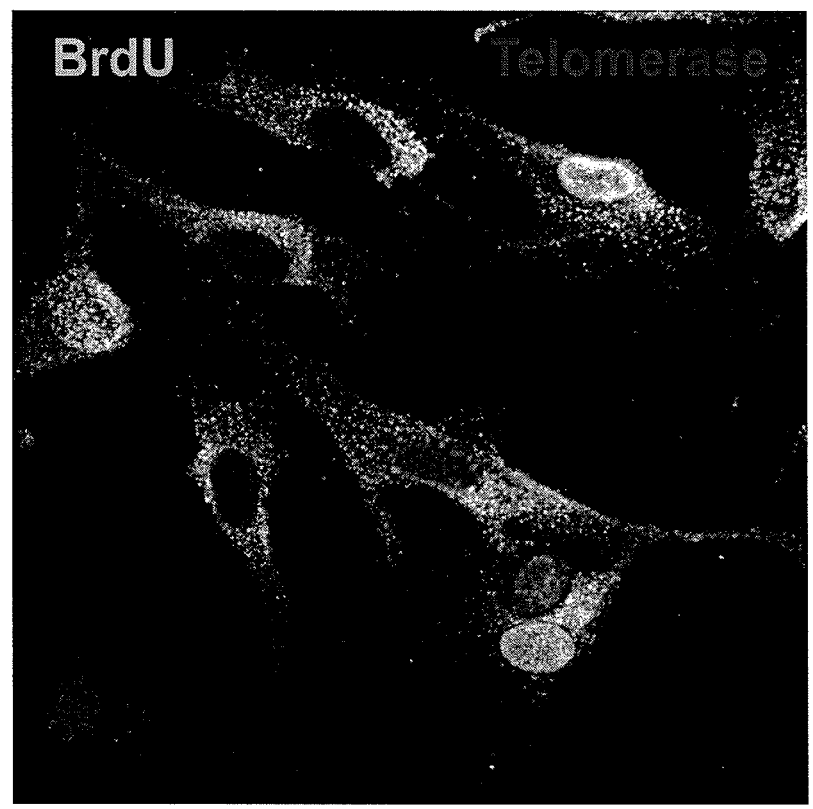
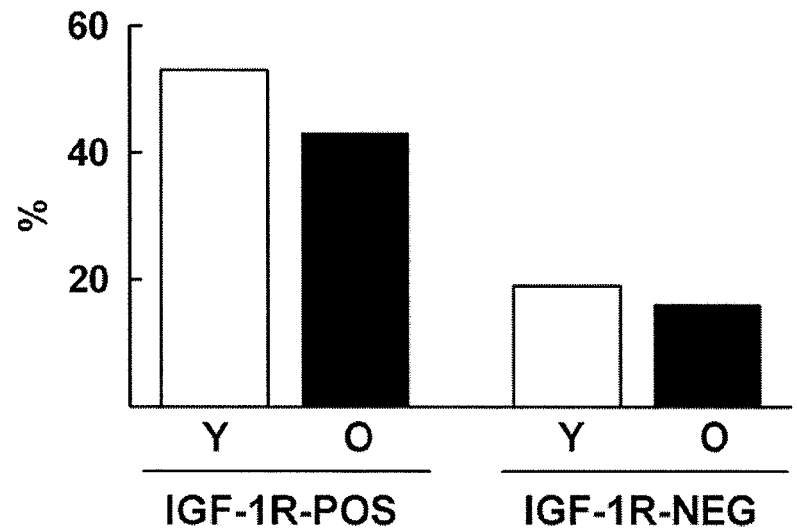

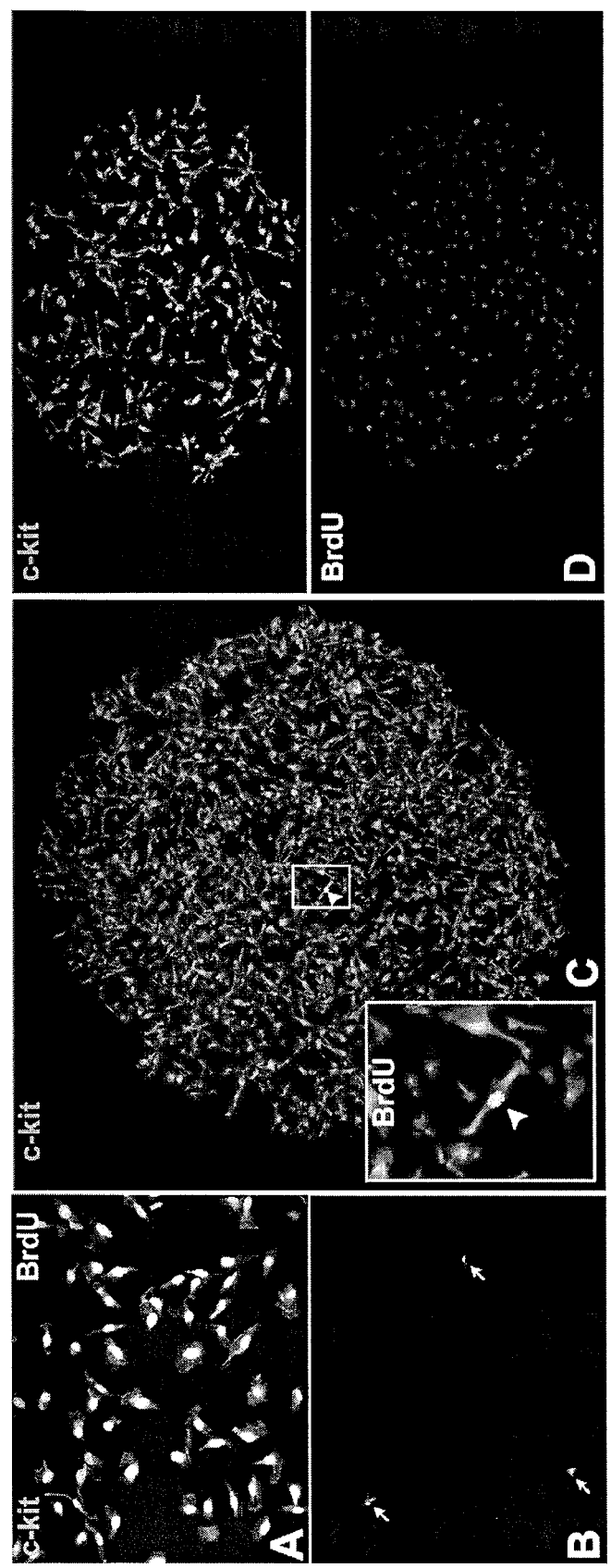
Figure 56 A-D

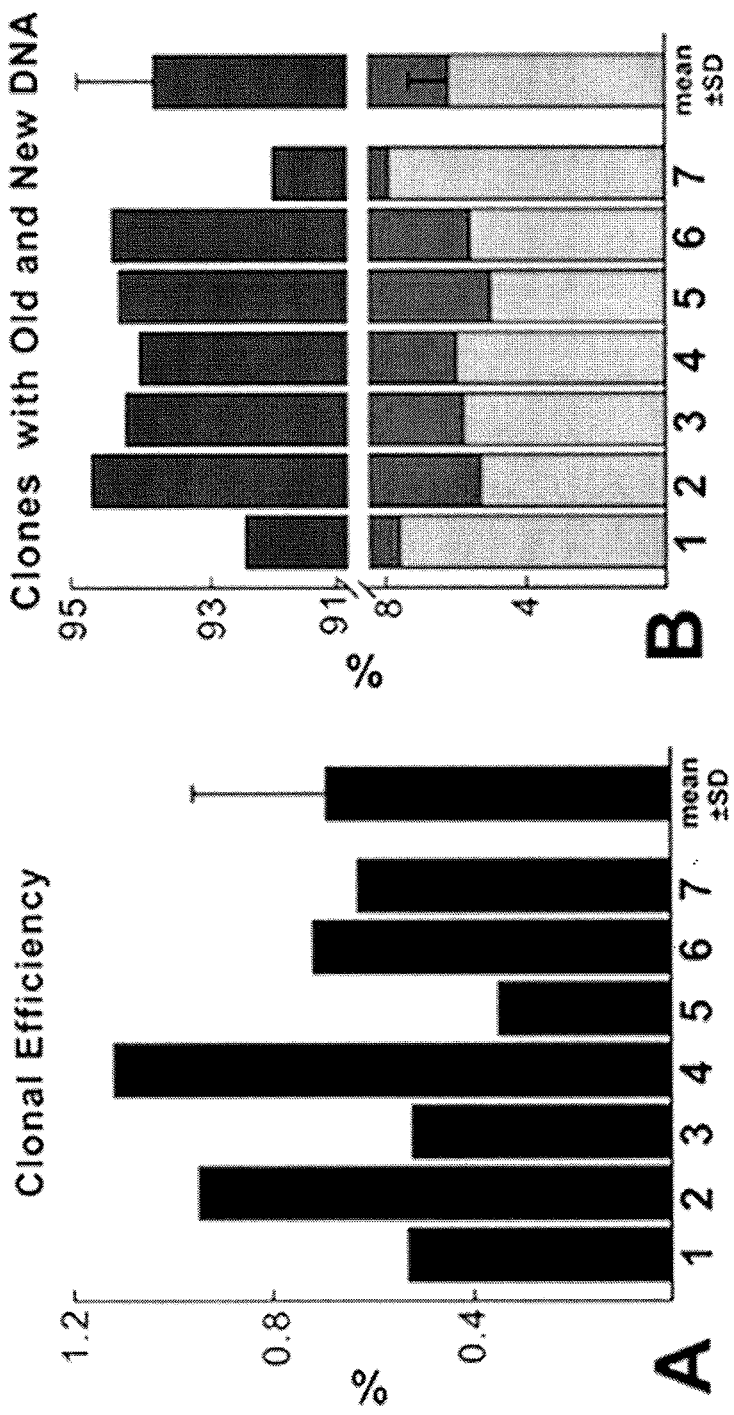
Figure 57 A-B

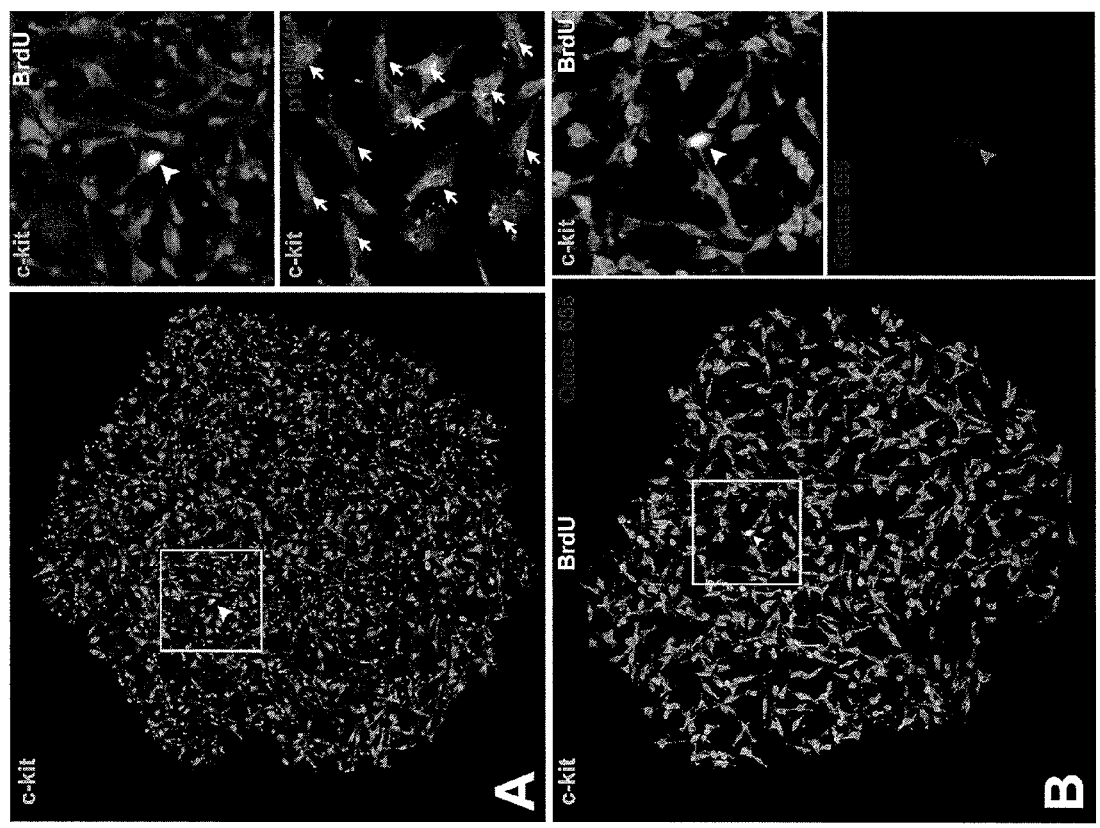
Figure 58 A-B

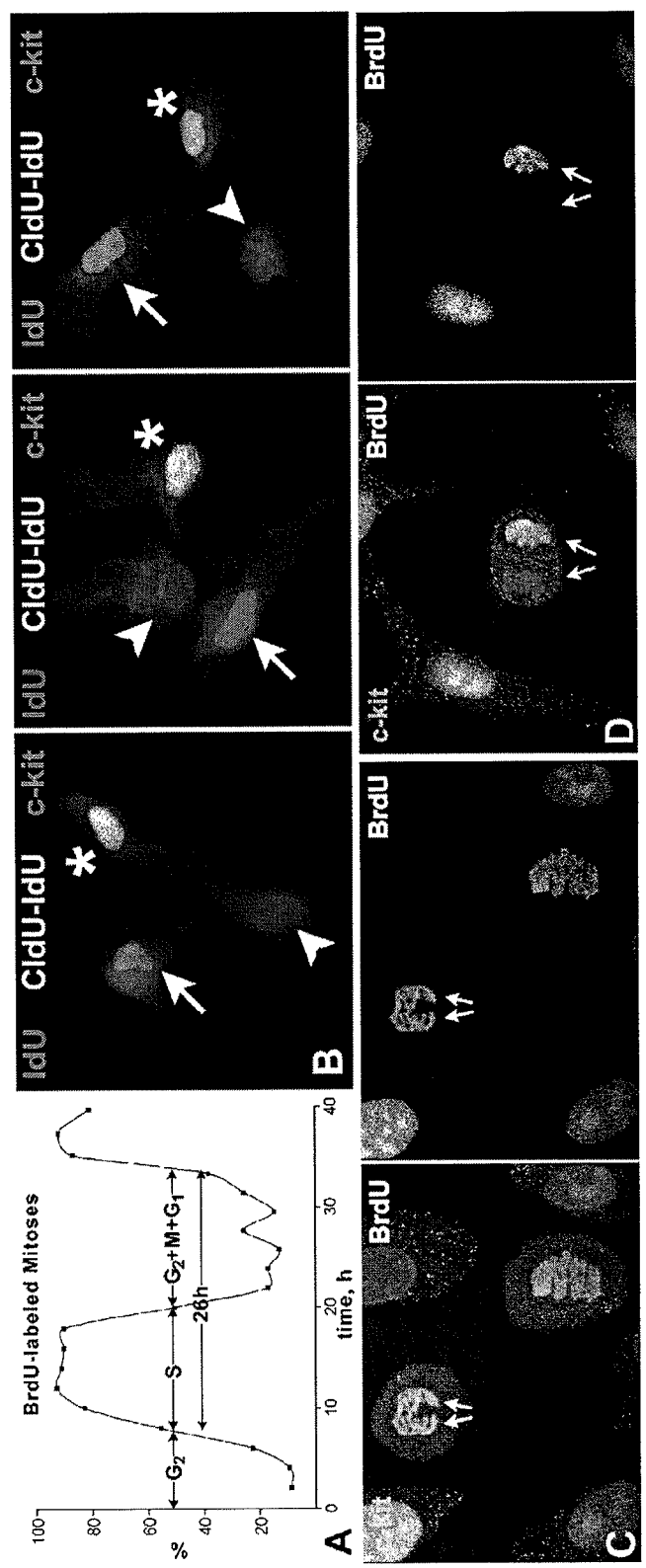
Figure 59 A-D

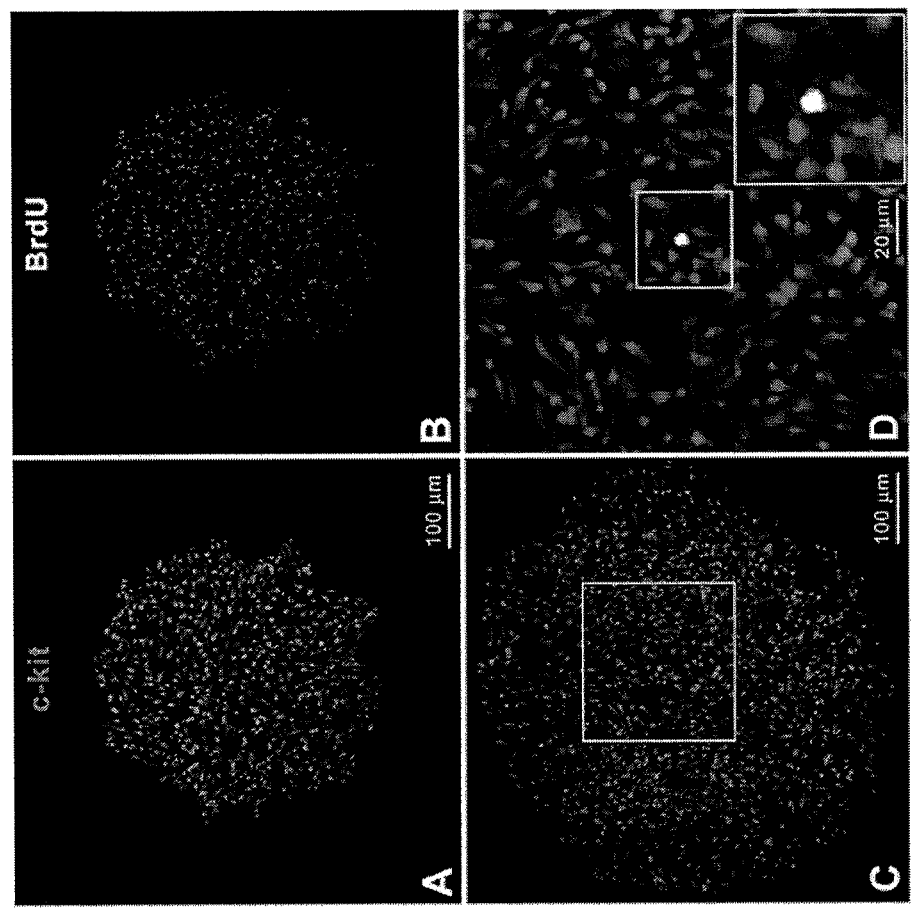
Figure 60 A-D

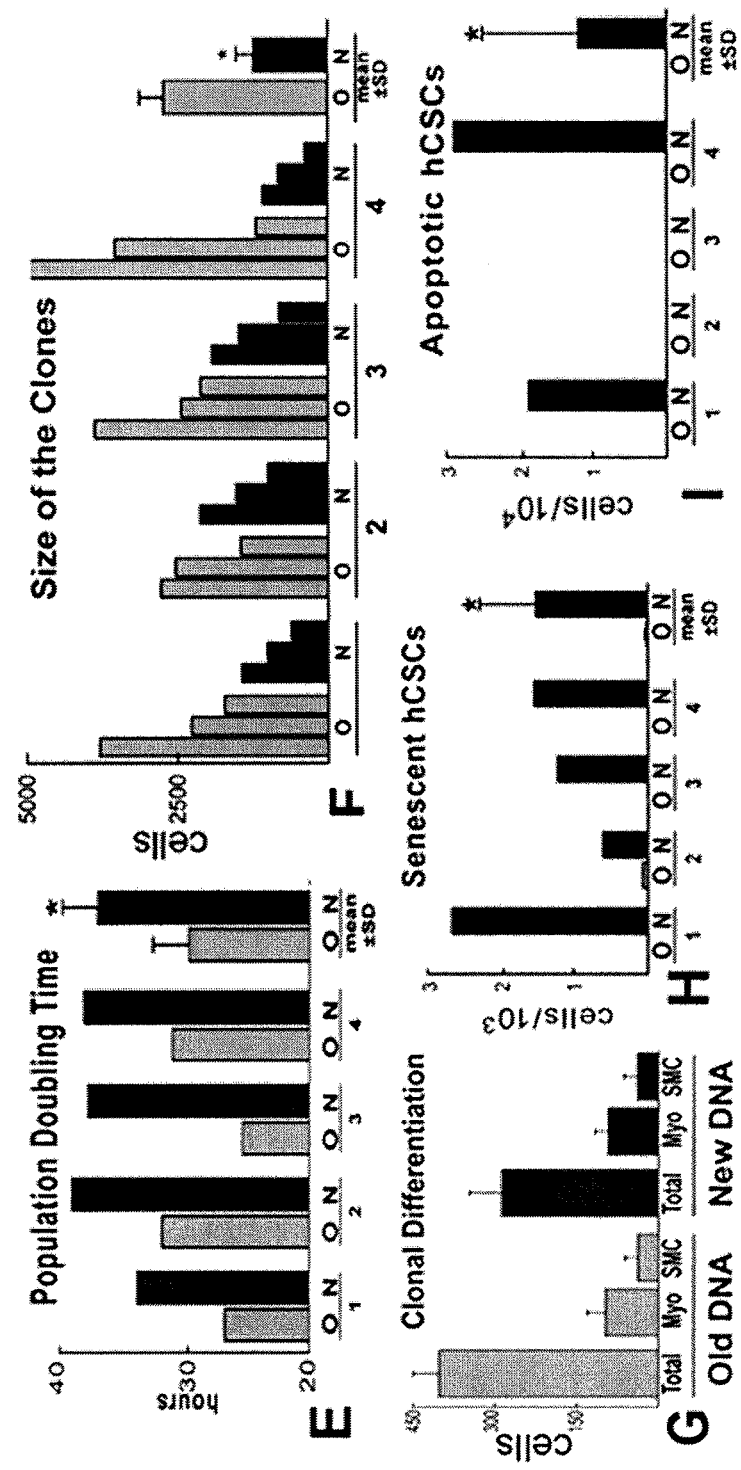
Figure 60 E-I

SEQUENCE LISTING

```
<160> NUMBER OF SEQ ID NOS: 23

<210> SEQ ID NO 1
<211> LENGTH: 18
<212> TYPE: DNA
<213> ORGANISM: Unknown
<220> FEATURE:
<223> OTHER INFORMATION: Telomerase substrate PCR primer

<400> SEQUENCE: 1
aatccgtcga gcagagtt                                                18

<210> SEQ ID NO 2
<211> LENGTH: 30
<212> TYPE: DNA
<213> ORGANISM: Rattus sp.

<400> SEQUENCE: 2
gcgcgcctaa ccctaacccct aaccctaacc                                  30

<210> SEQ ID NO 3
<211> LENGTH: 22
<212> TYPE: DNA
<213> ORGANISM: Rattus sp.

<400> SEQUENCE: 3
cgaacctcca ataaagatac ac                                           22

<210> SEQ ID NO 4
<211> LENGTH: 20
<212> TYPE: DNA
<213> ORGANISM: Rattus sp.

<400> SEQUENCE: 4
caacactcat ccacaatgcc                                              20

<210> SEQ ID NO 5
<211> LENGTH: 21
<212> TYPE: DNA
<213> ORGANISM: Rattus sp.

<400> SEQUENCE: 5
cgagcaagtt cttcgtttcg t                                            21
```

```
<210> SEQ ID NO 6
<211> LENGTH: 19
<212> TYPE: DNA
<213> ORGANISM: Rattus sp.

<400> SEQUENCE: 6
tgtactgcca gcacatgcg                                                      19

<210> SEQ ID NO 7
<211> LENGTH: 19
<212> TYPE: DNA
<213> ORGANISM: Rattus sp.

<400> SEQUENCE: 7
tgccctattt cccgttgtg                                                      19

<210> SEQ ID NO 8
<211> LENGTH: 23
<212> TYPE: DNA
<213> ORGANISM: Rattus sp.

<400> SEQUENCE: 8
aatgccattt acaactcgca gtt                                                 23

<210> SEQ ID NO 9
<211> LENGTH: 20
<212> TYPE: DNA
<213> ORGANISM: Rattus sp.

<400> SEQUENCE: 9
acaacaaaac gggtgcgaaa                                                     20

<210> SEQ ID NO 10
<211> LENGTH: 21
<212> TYPE: DNA
<213> ORGANISM: Rattus sp.

<400> SEQUENCE: 10
tcatgagctc ccagagaagc a                                                   21

<210> SEQ ID NO 11
<211> LENGTH: 21
<212> TYPE: DNA
<213> ORGANISM: Rattus sp.

<400> SEQUENCE: 11
cctgggagtc aaagagaaga g                                                   21

<210> SEQ ID NO 12
<211> LENGTH: 22
<212> TYPE: DNA
<213> ORGANISM: Rattus sp.

<400> SEQUENCE: 12
gtatagaact tgcggatgaa gg                                                  22

<210> SEQ ID NO 13
<211> LENGTH: 20
<212> TYPE: DNA
<213> ORGANISM: Rattus sp.

<400> SEQUENCE: 13
atcaacaggt ttgtgcaggc                                                     20
```

```
<210> SEQ ID NO 14
<211> LENGTH: 22
<212> TYPE: DNA
<213> ORGANISM: Rattus sp.

<400> SEQUENCE: 14
gttgtccacc cagaactcat gg                                              22

<210> SEQ ID NO 15
<211> LENGTH: 22
<212> TYPE: DNA
<213> ORGANISM: Rattus sp.

<400> SEQUENCE: 15
gtcctctcag ctctgccaca tt                                              22

<210> SEQ ID NO 16
<211> LENGTH: 24
<212> TYPE: DNA
<213> ORGANISM: Rattus sp.

<400> SEQUENCE: 16
cacttgacct ttacctggtg atca                                            24

<210> SEQ ID NO 17
<211> LENGTH: 20
<212> TYPE: DNA
<213> ORGANISM: Rattus sp.

<400> SEQUENCE: 17
accctgtgct gctcaccgag                                                 20

<210> SEQ ID NO 18
<211> LENGTH: 20
<212> TYPE: DNA
<213> ORGANISM: Rattus sp.

<400> SEQUENCE: 18
ccagtggtac gaccagaggc                                                 20

<210> SEQ ID NO 19
<211> LENGTH: 30
<212> TYPE: DNA
<213> ORGANISM: Homo sapiens

<400> SEQUENCE: 19
gcgcgcctta cccttaccct taccctaacc                                      30

<210> SEQ ID NO 20
<211> LENGTH: 10
<212> TYPE: PRT
<213> ORGANISM: Unknown
<220> FEATURE:
<223> OTHER INFORMATION: H2B histone sequence

<400> SEQUENCE: 20

Arg Lys Arg Ser Arg Lys Glu Ser Tyr Ser
1               5                   10

<210> SEQ ID NO 21
<211> LENGTH: 10
<212> TYPE: PRT
<213> ORGANISM: Homo sapiens

<400> SEQUENCE: 21
```

```
Ala Val Arg Ile Arg Gly Lys Ser Tyr Val
1               5                   10

<210> SEQ ID NO 22
<211> LENGTH: 6
<212> TYPE: PRT
<213> ORGANISM: Unknown
<220> FEATURE:
<223> OTHER INFORMATION: Akt consensus site
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Ser may be phosphorylated

<400> SEQUENCE: 22

Arg Xaa Arg Xaa Xaa Ser
1               5

<210> SEQ ID NO 23
<211> LENGTH: 10
<212> TYPE: PRT
<213> ORGANISM: Artificial Sequence
<220> FEATURE:
<223> OTHER INFORMATION: Consensus sequence for Akt phosphorylation in
      mouse telomerase

<400> SEQUENCE: 23

Arg Val Arg Leu Arg Glu Leu Ser Gln Glu
1               5                   10
```

METHODS OF ISOLATING NON-SENESCENT CARDIAC STEM CELLS AND USES THEREOF

CROSS REFERENCE TO RELATED APPLICATIONS

This application is a continuation-in-part of U.S. application Ser. No. 12/324,031, filed Nov. 26, 2008, which claims the benefit of U.S. Provisional Application No. 60/991,637, filed Nov. 30, 2007, and U.S. Provisional Application No. 61/057,049, filed May 29, 2008, all of which are herein incorporated by reference in their entirety.

STATEMENT OF GOVERNMENT SUPPORT

This work was in part supported by the government, by grants from the National Institutes of Health, Grant Nos: HL-38132, AG-15756, HL-65577, HL-66923, HL-65573, HL-075480, AG-17042, HL-081737, AG-026107 and AG-023071. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: AUTL_003_03US_SeqList_ST25.txt, date recorded: Jan. 17, 2011, file size 5 kilobytes).

FIELD OF THE INVENTION

The present invention relates generally to the field of cardiology, and more particularly relates to methods of isolating a particular class of adult cardiac stem cells. The invention also encompasses compositions containing these isolated stem cells and methodologies using these compositions for the treatment of cardiovascular disease, the repair of age-related cardiomyopathy, and the prevention of heart failure.

BACKGROUND OF THE INVENTION

Heart failure is the leading cause of death in the elderly. However, it is unclear whether this is the result of a primary aging cardiomyopathy or the consequence of chronic coronary artery disease. In humans, it is difficult to separate the inevitable pathology of the coronary circulation with age from the intrinsic mechanisms of myocardial aging and heart failure. The aging heart typically shows a decreased functional reserve and limited capacity to adapt to cardiac diseases (Maggioni et al. (1993) N. Engl. J. Med. 329: 1442-1448). An important question is whether average lifespan reflects the ineluctable genetic clock (Sanderson and Scherbov (2005) Nature 435: 811-813) or heart failure interferes with the programmed death of the organ and organism negatively affecting lifespan in humans.

Cardiovascular disease is one possible cause of heart failure and a major health risk throughout the industrialized world. Atherosclerosis, the most prevalent of cardiovascular diseases, is the principal cause of heart attack, stroke, and gangrene of the extremities, and thereby the principal cause of death in the United States. Atherosclerosis is a complex disease involving many cell types and molecular factors (for a detailed review, see Ross (1993) Nature 362: 801-809).

Ischemia is a condition characterized by a lack of oxygen supply in tissues of organs due to inadequate perfusion. Such inadequate perfusion can have a number of natural causes, including atherosclerotic or restenotic lesions, anemia, or stroke, to name a few. Many medical interventions, such as the interruption of the flow of blood during bypass surgery, for example, also lead to ischemia. In addition to sometimes being caused by diseased cardiovascular tissue, ischemia may sometimes affect cardiovascular tissue, such as in ischemic heart disease. Ischemia may occur in any organ, however, that is suffering a lack of oxygen supply.

The most common cause of ischemia in the heart is myocardial infarction (MI). Commonly known as a heart attack, MI is one of the most well-known types of cardiovascular disease. 1998 estimates show 7.3 million people in the United States suffer from MI, with over one million experiencing an MI in a given year (American Heart Association, 2000). Of these individuals, 25% of men, and 38% of females will die within a year of their first recognized MI (American Heart Association, 2000). MI is caused by a sudden and sustained lack of blood flow to an area of the heart, typically caused by narrowing of a coronary artery. Without adequate blood supply, the tissue becomes ischemic, leading to the death of myocytes and vascular structures. This area of necrotic tissue is referred to as the infarct site, and will eventually become scar tissue. Survival is dependent on the size of this infarct site, with the probability of recovery decreasing with increasing infarct size. For example, in humans, an infarct of 46% or more of the left ventricle triggers irreversible cardiogenic shock and death.

Most studies on MI have focused on reducing infarct size. There have been a few attempts to regenerate the necrotic tissue by transplanting cardiomyocytes or skeletal myoblasts (Leor et al. (1996) Circulation 94:(Supplement II) II-332-II-336; Murray et al. (1996) Clin. Invest. 98:2512-2523; Taylor et al. (1998) Nature Med. 4, 929-933; Tomita et al. (1999) Circulation 100(suppl II), II-247-II-256; Menasche et al. (2000) Circulation 100(suppl II), II-247-II-256). While the cells may survive after transplantation, they fail to reconstitute healthy myocardium and coronary vessels that are both functionally and structurally sound.

All of the cells in the normal adult originate as precursor cells which reside in various sections of the body. These cells, in turn, derive from very immature cells, called progenitors, which are assayed by their development into contiguous colonies of cells in 1-3 week cultures in semisolid media such as methylcellulose or agar or liquid media. Progenitor cells themselves derive from a class of progenitor cells called stem cells. Stem cells have the capacity, upon division, for both self-renewal and differentiation into progenitors. Thus, dividing stem cells generate both additional primitive stem cells and somewhat more differentiated progenitor cells. In addition to the well-known role of stem cells in the development of blood cells, stem cells also give rise to cells found in other tissues, including but not limited to the liver, brain, and heart.

Stem cells have the ability to divide indefinitely, and to specialize into specific types of cells. Totipotent stem cells, which exist after an egg is fertilized and begins dividing, have total potential, and are able to become any type of cell. Once the cells have reached the blastula stage, the potential of the cells has lessened, with the cells still able to develop into any cell within the body, however they are unable to develop into the support tissues needed for development of an embryo. The cells are considered pluripotent, as they may still develop into many types of cells. During development, these cells become more specialized, committing to give rise to cells with a specific function. These cells, considered multipotent, are found in human adults and referred to as adult stem cells. It is well known that stem cells are located in the bone marrow, and that there is a small amount of peripheral blood stem cells that circulate throughout the blood stream (National Institutes of Health, 2000).

To date, with the exception of a few hematological disorders (Bagby et al. (2004) Hematology Am. Soc. Hematol. Educ. Program 318-336), stem cell failure does not occur in self-renewing organs including the human heart. Pools of functionally competent cardiac stem cells are present in the heart of patients who die acutely after a large myocardial infarct or undergo cardiac transplantation for end-stage ischemic and non-ischemic cardiomyopathy (Urbanek et al. (2003) Proc. Natl. Acad. Sci. USA 100, 10440-10445; Urbanek et al. (2005) Proc. Natl. Acad. Sci. USA 102, 8692-8697). Similarly, cycling cardiac stem cells with long telomeres have been identified in the old decompensated human heart in the absence of risk factors of coronary artery disease and cardiac failure (Chimenti et al. (2003) Circ. Res. 93: 604-613).

SUMMARY OF THE INVENTION

The present invention is based, in part, on the discovery of a subset of adult cardiac stem cells that reside in the adult myocardium which exhibit superior regenerative capabilities and do not show cellular senescence even after several passages in culture. These cells retain relatively high amounts of telomerase activity, have long telomeres, and are $p16^{INK4a}$ negative. In some embodiments, these cells express the IGF-1 receptor. The present invention provides methods for isolating this non-senescent subset of adult cardiac stem cells as well as methods of using this pool of non-senescent cardiac stem cells to treat various cardiac conditions.

The present invention includes methods of isolating non-senescent adult cardiac stem cells from myocardial tissue, such as human myocardial tissue. In one embodiment, the method comprises extracting cardiac stem cells from a subject; expanding and culturing said stem cells; determining telomere length, telomerase activity, and/or IGF-1 receptor expression in the expanded stem cells; and selecting those stem cells positive for IGF-1 receptors and/or having specified telomere lengths and levels of telomerase activity. In one embodiment, the isolated non-senescent stem cells express one or more stem cells markers, such as c-kit and MDR1.

In another aspect of the invention, the non-senescent cardiac stem cells can be further selected for stem cells possessing immortal DNA. Cardiac stem cells retaining old DNA template strands (e.g. immortal DNA) following cell replication have greater growth potential (i.e. generate larger numbers of non-senescent cells) and repair capabilities than cardiac stem cells that have only new DNA templates. In one embodiment, such cardiac stem cells having immortal DNA are identified by selecting clones of cardiac stem cells that do not retain a DNA label following at least one passage in cell culture.

The invention also provides pharmaceutical compositions of the isolated non-senescent adult cardiac stem cells. In one embodiment, the pharmaceutical composition comprises isolated human cardiac stem cells and a pharmaceutically acceptable carrier, wherein said isolated human cardiac stem cells are c-kit positive, IGF-1 receptor positive, and have telomeres greater than 5 kbp in length. In another embodiment, the human cardiac stem cells are $p16^{INK4a}$ negative. In some embodiments, the pharmaceutical compositions comprise a mixture of isolated human cardiac stem cells having immortal DNA and other stem cells (e.g. other cardiac stem cells, such as those with new DNA template strands). In such compositions, the compositions comprise at least 8% or more of isolated cardiac stem cells comprising the immortal DNA.

The invention also encompasses methods of repairing damaged myocardium and/or age-related cardiomyopathy in a subject comprising administering the isolated non-senescent adult cardiac stem cells to an area of damaged and/or aged myocardium, wherein the cardiac stem cells generate myocardium and/or myocardial cells after their administration, thereby repairing damaged myocardium and/or age-related cardiomyopathy. In certain embodiments, the isolated non-senescent cardiac stem cells contain immortal DNA. In such embodiments, the non-senescent cardiac stem cells restore the structural and functional integrity of the damaged myocardium to a greater extent than senescent cardiac stem cells (e.g. cardiac stem cells not having the markers of non-senescence as described herein). The isolated non-senescent adult cardiac stem cells may be activated prior to administration. In one embodiment, the isolated non-senescent adult cardiac stem cells are activated by exposing them to one or more cytokines, such as hepatocyte growth factor or insulin-like growth factor-1. In another embodiment, the activated stem cells are autologous or isolated from the same subject to which they are re-administered. In some embodiments, the method further comprises the intramyocardial administration of one or more cytokines to form a chemotactic gradient, wherein said chemotactic gradient facilitates the mobilization of the administered non-senescent adult cardiac stem cells to areas of aged or damaged myocardium.

The present invention also includes methods of preventing or treating heart failure in a subject comprising administering the isolated non-senescent adult cardiac stem cells (including those cardiac stem cells containing immortal DNA) to the subject's heart, and administering an angiotensin II receptor antagonist. In some embodiments, the method further comprises the administration of an angiotensin converting enzyme (ACE) inhibitor. The isolated non-senescent cardiac stem cells may be activated by exposure to one or more cytokines prior to administration. In other embodiments, the method further comprises the intramyocardial administration of one or more cytokines, such as hepatocyte growth factor or insulin-like growth factor-1, to form a chemotactic gradient to promote the migration of the implanted activated stem cells to areas of aged or damaged myocardium.

BRIEF DESCRIPTION OF THE DRAWINGS

FIG. 21. Proliferation (A) and apoptosis (B) of young and old CPCs. Percent changes were computed with respect to the values in non-stimulated CPCs. *p<0.05 versus 3 months (3 m). Localization of 8-OH-dG (magenta) in young (C) and old (D) CPCs at baseline (left panels) and following Ang II stimulation (right panels). (E) CPCs positive for 8-OH-dG. *p<0.05 versus 3 m; †p<0.05 versus SFM.

FIG. 53. Detection of the components of the local RAS (A-J) and IGF-1-IGF-1R system (K-N) in hCPC by real-time RT-PCR (A-C,H,K,L) and immunocytochemistry (D-G,I,J,M,N).

FIG. 54. The upper panel illustrates the localization of telomerase (magenta) and BrdU (green) in hCPCs positive for IGF-1R (not shown) collected from an old patient. The lower panel shows that BrdU labeling is higher in hCPCs expressing IGF-1R in both young (Y) and old (O) patients.

FIG. 57. HCSC Growth. A: Clonal efficiency. B: hCSCs with old (green) and new (red) DNA; mean±SD.

FIG. 58. $p16^{INK4a}$ and Qdots labeling of hCSCs. A: Clone in which the 1 BrdU-positive cell (white, arrowhead), shown at higher power in the adjacent panel is p16-negative. Control for senescent p16-positive hCSCs (magenta, arrows) is shown. B: Clone in which the 1 BrdU-positive cell (white, arrowhead) is shown at higher power in the adjacent panel. This cell retained a large number of Qdots (red fluorescence). Minimal amounts of Qdots are present in the other clonal cells which underwent multiple rounds of division.

FIG. 59. hCSC division. A: Length of the cell cycle in hCSCs. B: Examples of clones consisting each of 3 c-kit-positive hCSCs. In each case, one cell is positive for CldU and IdU (asterisks), one cell for IdU only (arrows), and one cell is negative for both CldU and IdU (arrowheads). C and D: hCSCs in anaphase showing uniform (C; white, arrows) and non-uniform (D; white, arrows) localization of BrdU in the two sets of chromosomes; in panel D only one set of chromosomes is BrdU-positive.

FIG. 60. hCSC clones. A-D: At 9 days after plating, a single BrdU-labeled hCSC with new DNA formed a clone of ~350 c-kit-positive cells (A, green), all labeled by BrdU (B, white). In contrast, a single BrdU-labeled hCSC with old DNA generated a clone of ~700 c-kit-positive cells (C) in which only one cell was BrdU-positive (D: inset, white). Population doubling time (PDT) (E) and clone size (F). hCSCs with old (green) and new (red) DNA. G: Cell differentiation. H: Only one p16-positive clonal cell was detected in the 12 clones from hCSCs with old DNA (green). Senescent cells were more frequent in the 12 clones from hCSCs with new DNA (red). I: Apoptosis was rare.

DETAILED DESCRIPTION OF THE INVENTION

Figure 1:
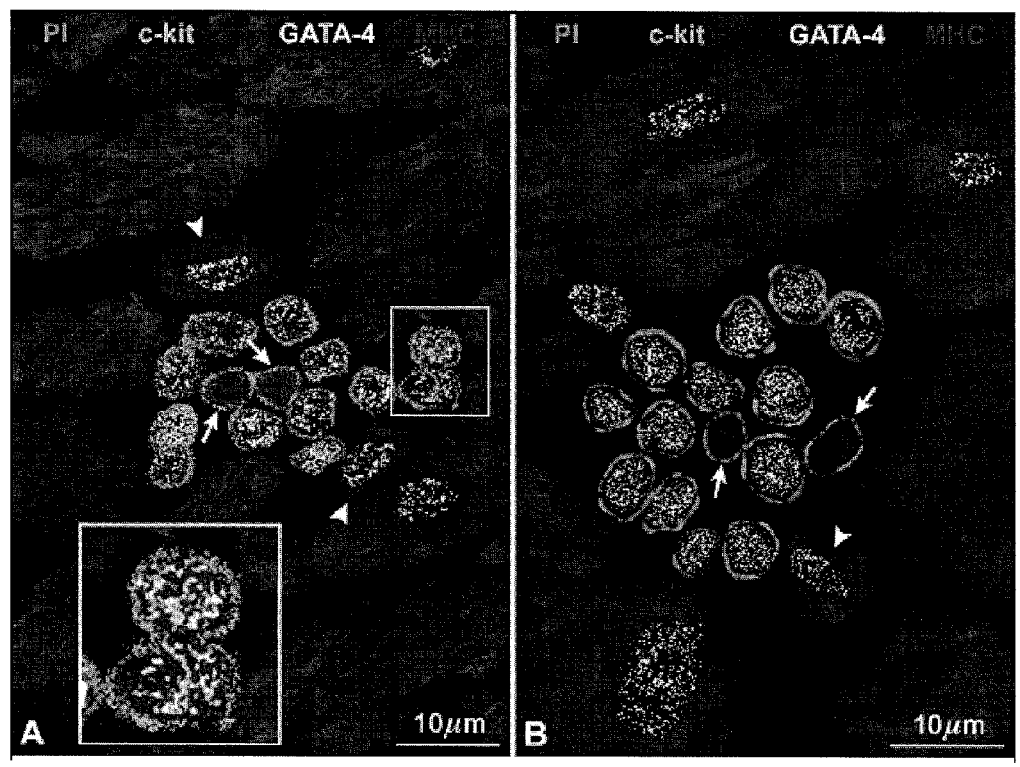
FIG. 1. (A) Cluster of 14 c-kit-positive-CPCs (green) in the apex of the left ventricle (LV) at 29 months; 12 of the 14 CPCs express GATA-4 (yellow; myocyte progenitors). Two of the 12 GATA-4-positive-CPCs (inset) express cardiac-myosin-heavy-chain (MHC, red; myocyte precursors). Two CPCs express only c-kit (green, arrows; $Lin^{neg}$-CPCs). Two small developing myocytes are present (arrowheads). Nuclei, PI (blue). (B) Cluster of 15 CPCs in the left atrium at 20 months; 13 are GATA-4-positive and 2 express only c-kit (arrows). A developing myocyte is present (arrowhead).

As used herein, "autologous" refers to something that is derived or transferred from the same individual's body (i.e., autologous blood donation; an autologous bone marrow transplant).

As used herein, "allogeneic" refers to something that is genetically different although belonging to or obtained from the same species (e.g., allogeneic tissue grafts).

As used herein, "stem cells" are used interchangeably with "progenitor cells" and refer to cells that have the ability to renew themselves through mitosis (self-renewing), are clonogenic, and can differentiate into various specialized cell types. The stem cells used in the invention are somatic stem cells, such as bone marrow or cardiac stem cells.

As used herein, "adult" stem cells refers to stem cells that are not embryonic in origin nor derived from embryos or fetal tissue.

Stem cells employed in the invention are advantageously selected to be lineage negative. The term "lineage negative" is known to one skilled in the art as meaning the cell does not express antigens characteristic of specific cell lineages. And, it is advantageous that the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

As used herein, "non-senescent stem cells" refer to stem cells that retain the ability to divide many times over without showing replicative senescence. Non-senescent stem cells have long telomeres and/or levels of telomerase activity that are at least 60% of the telomerase activity in freshly isolated c-kit positive cardiac cells from young animals. "Long telomeres" refer to telomeres that have lengths that are about or greater than the average telomere length from cardiac stem cells isolated from younger animals. By way of example, long telomeres in rodents are telomeres having lengths greater than or equal to about 18 kbp. In humans, long telomeres are telomeres having lengths greater than or equal to about 5 kbp. As used herein, "human non-senescent stem cells" refer to stem cells that have telomere lengths greater than or equal to about 5 kbp or levels of telomerase activity that are at least 60% of the telomerase activity in freshly isolated c-kit positive cardiac cells from young (20-40 years) individuals. Non-senescent stem cells are negative for markers of senescence such as $p16^{INK4a}$. Thus, non-senescent cardiac stem cells are $p16^{INK4a}$-negative. In some embodiments, non-senescent cardiac stem cells express the IGF-1 receptor (i.e. the non-senescent cardiac stem cells are IGF-1R positive).

As used herein "damaged myocardium" refers to myocardial cells which have been exposed to ischemic conditions. These ischemic conditions may be caused by a myocardial infarction, or other cardiovascular disease or related complaint. The lack of oxygen causes the death of the cells in the surrounding area, leaving an infarct, which will eventually scar.

As used herein "age-related cardiomyopathy" refers to the deterioration of the myocardium as a result of intrinsic mechanisms occurring as the organism ages.

As used herein, the tet "cytokine" is used interchangeably with "growth factor" and refers to peptides or proteins that bind receptors on cell surfaces and initiate signaling cascades thus influencing cellular processes. The terms "cytokine" and "growth factor" encompass functional variants of the native cytokine or growth factor. A functional variant of the cytokine or growth factor would retain the ability to activate its corresponding receptor. Variants can include amino acid substitutions, insertions, deletions, alternative splice variants, or fragments of the native protein. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological activity can be found using computer programs well known in the art, for example, DNASTAR software.

The pharmaceutical compositions of the present invention may be used as therapeutic agents—i.e. in therapy applications. As herein, the terms "treatment" and "therapy" include curative effects, alleviation effects, and prophylactic effects. In certain embodiments, a therapeutically effective dose of stem cells and/or cytokines is applied, delivered, or administered to the heart or implanted into the heart. An effective dose or amount is an amount sufficient to effect a beneficial or desired clinical result. Said dose could be administered in one or more administrations.

As used herein, "patient" or "subject" may encompass any vertebrate including but not limited to humans, mammals, reptiles, amphibians and fish. However, advantageously, the patient or subject is a mammal such as a human, or a mammal such as a domesticated mammal, e.g., dog, cat, horse, and the like, or production mammal, e.g., cow, sheep, pig, and the like. In a preferred embodiment, the patient or subject is human.

The present invention provides methods of isolating a specific subset of adult cardiac stem cells. These "non-senescent" adult cardiac stem cells avoid cellular senescence by retaining normal telomerase activity and long telomeres, which enable the stem cells to continue to divide and differentiate without giving rise to progeny with shortened telomeres. Thus, the viable myocytes, endothelial cells, and smooth muscle cells generated from the non-senescent adult cardiac stem cells can integrate functionally into pre-existing myocardium to repair age-related cardiomyopathy or damaged myocardium, thereby preserving organ function. The non-senescent cardiac stem cells exhibit enhanced growth and regenerative capabilities compared to cardiac stem cells that lack the non-senescent markers described herein (e.g. long telomeres, high telomerase activity, p16$^{INK4a}$-negative, and IGF-1R).

In one embodiment of the invention, the method of isolating non-senescent adult cardiac stem cells comprises extracting cardiac stem cells from a subject; expanding and culturing the stem cells; determining at least one non-senescent characteristic of the cultured stem cells, wherein said characteristic is selected from the group consisting of telomere length, telomerase activity, p16$^{INK4a}$ expression, and IGF-1 receptor expression; and selecting stem cells with long telomeres, stem cells with at least 60% telomerase activity as compared to a control, stem cells that are p16$^{INK4a}$-negative, stem cells expressing IGF-1 receptor, or combinations thereof, wherein said selected stem cells are non-senescent adult cardiac stem cells. In some embodiments, the isolated non-senescent adult cardiac stem cells express c-kit, MDR-1, or combinations thereof. In another embodiment, the step of extracting cardiac stem cells from a subject comprises obtaining a myocardial tissue specimen from a subject and isolating the stem cells from the tissue specimen. In preferred embodiments, the subject is human.

Methods of isolating adult stem cells are known in the art. Stem cells may be isolated from tissue specimens, such as myocardium or bone marrow, obtained from a subject or patient. By way of example, the tissue specimens may be minced and placed in appropriate culture medium. Stem cells growing out from the tissue specimens can be observed in approximately 1-2 weeks after initial culture. At approximately 4 weeks after the initial culture, the expanded stem cells may be collected by centrifugation. U.S. Patent Application Publication No. 2006/0239983, filed Feb. 16, 2006, which is herein incorporated by reference, describes media appropriate for culturing and expanding adult stem cells. However, one of ordinary skill in the art would be able to determine the necessary components and modify commonly used cell culture media to be employed in culturing the isolated stem cells of the invention.

It is preferable that the stem cells of the invention are lineage negative (Lin$^{NEG}$). Lin$^{NEG}$ stem cells can be isolated by various means, including but not limited to, removing lineage positive cells by contacting the stem cell population with antibodies against lineage markers and subsequently isolating the antibody-bound cells by using an anti-immunoglobulin antibody conjugated to magnetic beads and a biomagnet. Alternatively, the antibody-bound lineage positive stem cells may be retained on a column containing beads conjugated to anti-immunoglobulin antibodies. For instance, cells expressing markers of the cardiac lineage (e.g. markers of vascular cell or cardiomyocyte commitment) may be removed from cardiac stem cell populations to isolate lineage negative cardiac stem cells. Markers of the vascular lineage include, but are not limited to, GATA6 (SMC transcription factor), Ets1 (EC transcription factor), Tie-2 (angiopoietin receptors), VE-cadherin (cell adhesion molecule), CD62E/E-selectin (cell adhesion molecule), alpha-SM-actin (α-SMA, contractile protein), CD31 (PECAM-1), vWF (carrier of factor VIII), Bandeiraera simplicifolia and *Ulex europaeus* lectins (EC surface glycoprotein-binding molecules). Markers of the myocyte lineage include, but are not limited to, GATA4 (cardiac transcription factor), NRx2.5 and MEF2C (myocyte transcription factors), and alpha-sarcomeric actin (α-SA, contractile protein).

In a preferred embodiment of the invention, the Lin$^{NEG}$ stem cells express one or more stem cell surface markers including c-kit, which is the receptor for stem cell factor and multidrug resistance-1 (MDR1), which is a P-glycoprotein capable of extruding dyes, toxic substances and drugs from the cell. Positive selection methods for isolating a population of Lin$^{NEG}$ stem cells expressing any one of these surface markers are well known to the skilled artisan. Examples of possible methods include, but are not limited to, various types of cell sorting, such as fluorescence activated cell sorting (FACS) and magnetic cell sorting as well as modified forms of affinity chromatography. In a preferred embodiment, the Lin$^{NEG}$ stem cells are c-kit positive.

Isolated Lin$^{NEG}$ stem cells expressing a stem cell marker may be plated individually in single wells of a cell culture plate and expanded to obtain clones from individual stem cells. In one embodiment, telomere length is measured in the clones derived from single stem cells. Methods of determining telomere length are well known in the art. Telomere length may be assessed by using methods such as quantitative fluorescence in situ hybridization (Q-FISH), Southern Blot, or quantitative PCR. Cells with telomeres that are at least 5 kbp, at least 7 kbp, at least 8 kbp, at least 9 kbp, at least 10 kbp, at least 12 kbp, at least 13 kbp, at least 14 kbp, at least 15 kbp, at least 16 kbp, at least 17 kbp, or at least 18 kbp in length may be selected for use or further expansion in cell culture. In a preferred embodiment, human cardiac stem cells with telomeres that are at least 5 kbp in length, more preferably at least 7 kbp in length, are selected for further use.

In another embodiment, telomerase activity is measured in the expanded stem cell clones. Methods of measuring telomerase activity may include electrophoretic and ELISA-based telomere repeat amplification protocol (TRAP) assays as well as real time PCR methods. Telomerase activity in the isolated stem cells may be compared to that in control cells. The control cells may be freshly isolated c-kit positive cardiac cells from young animals. In the case of human non-senescent cardiac stem cells, the control cells may be freshly isolated c-kit positive cardiac cells from a young (20-40 years) individual. Stem cells expressing at least 60%, at least 70%, at least 80%, preferably 90%, or more preferably 95% of the telomerase activity as compared to control cells may be selected for use and further expansion.

In yet another embodiment, insulin-like growth factor-1 (IGF-1) receptor expression is assessed in the expanded stem cell clones. The IGF-1 receptor is a surface protein and can be detected by routine methods known to the skilled artisan to measure expression of surface markers. Such methods include, but are not limited to FACS, magnetic cell sorting, and modified forms of affinity chromatography. Alternatively, IGF-1 receptor expression can be measured by immunocytochemistry or Western blotting techniques. In a preferred embodiment, stem cell clones positive for IGF-1 receptor expression are selected for further use.

In still another embodiment, the expanded stem cell clones can be measured for p16$^{INK4a}$ expression. In a preferred embodiment, stem clones negative for p16$^{INK4a}$ expression are selected for further use.

In certain embodiments, the expanded cardiac stem clones can be selected for clones containing immortal DNA. As used herein "immortal DNA" refers to the old template strands (as opposed to the newly synthesized DNA strands) that are retained following cell replication. A small subset of cardiac stem cells divide by non-random chromatid segregation resulting in daughter cells that retain the old template strands (i.e. immortal DNA) and daughter cells that inherit the newer template strands (i.e. new DNA). The inventors have discovered that while both classes of cardiac stem cells (i.e. those possessing immortal DNA and new DNA) can effectively repair the structure and function of damaged heart tissue, the cardiac stem cells containing immortal DNA exhibit superior growth and regenerative capabilities as compared to cardiac stem cells containing the new DNA. See Example 8F. Cardiac stem cell clones containing immortal DNA can be identified by selecting those clones that are negative for a DNA marker following at least one passage or population doubling of the DNA labeled-parent cardiac stem cells in culture. For instance, cardiac stem cells are labeled with bromodeoxyuridine (BrdU) and clones are then subsequently generated from individual BrdU-labeled cells by growing the labeled parent cells in culture in the absence of the DNA label until at least one population doubling has occurred. The resulting clones that are BrdU-negative represent the cardiac stem cells that retain the old template or immortal DNA. The cardiac stem cells containing the immortal DNA can also be identified by other methods, such as those employing a FRET strategy followed by a FACs analysis as described in Example 8. Other methods of differentiating between cells containing newly synthesized DNA templates and old DNA templates using other labels are known to those of skill in the art and can be employed to identify cardiac stem cells containing immortal DNA.

The present invention also provides methods of repairing and/or regenerating damaged myocardium or age-related cardiomyopathy in a subject in need thereof by administering isolated non-senescent stem cells to areas of damaged myocardium, wherein the administered stem cells differentiate into one or more of myocytes, endothelial cells, or smooth muscle cells. The differentiated cells may proliferate and form various cardiac structures including coronary arteries, arterioles, capillaries, and myocardium, which are all structures essential for proper function in the heart. It has been shown in the literature that implantation of cells including endothelial cells and smooth muscle cells will allow for the implanted cells to live within the damaged region, however they do not form the necessary structures to enable the heart to regain full functionality. The ability to restore both functional and structural integrity is yet another aspect of this invention. In a preferred embodiment, the non-senescent stem cells are adult cardiac stem cells. In another embodiment, non-senescent adult cardiac stem cells are isolated from cardiac tissue harvested from the subject in need of therapeutic treatment for one of the cardiac or vasculature conditions described herein and implanted back into said subject.

In one embodiment, the method comprises administering isolated non-senescent cardiac stem cells that contain immortal DNA. As described above, this subset of cardiac stem cells exhibits superior regenerative properties as compared to other populations of cardiac stem cells (e.g. cardiac stem cells that contain the new DNA or cardiac stem cells that do not possess a non-senescent marker as described herein). For instance, in some embodiments, the structural repair of the damaged myocardium is enhanced following the administration of cardiac stem cells containing immortal DNA relative to the repair observed with cardiac stem cells not containing immortal DNA. Measurements of structural repair include, but are not limited to, increased wall thickening, number of myocytes formed, extent of cell replication, and number of regenerated arterioles and capillaries. In other embodiments, the functional repair of the damaged myocardium is enhanced following the administration of cardiac stem cells containing immortal DNA relative to the repair observed with cardiac stem cells not containing immortal DNA. Measurements of functional repair include, but are not limited to, hemodynamic measurements, such as recovery of systolic pressure, positive and negative dP/dt, and the attenuation in the increase of computed diastolic stress.

Thus, the invention involves administering a therapeutically effective dose or amount of stem cells to the heart. An effective dose is an amount sufficient to effect a beneficial or desired clinical result. Said dose could be administered in one or more administrations. As illustrated in the examples in co-pending U.S. Application Publication No. 2006/0239983, filed Feb. 16, 2006, which is herein incorporated by reference, $2 \times 10^4$-$1 \times 10^5$ stem cells were sufficient to effect myocardial repair and regeneration in a mouse model of myocardial infarction. While there would be an obvious size difference between the hearts of a mouse and a human, it is possible that this range of stem cells would be sufficient in a human as well. An effective dose of cardiac stem cells may be from about $2\times10^4$ to about $2\times10^7$, more preferably about $1\times10^5$ to about $6\times10^6$, or most preferably about $2\times10^6$. However, the precise determination of what would be considered an effective dose may be based on factors individual to each patient, including their size, age, area of myocardial damage, and amount of time since damage. One skilled in the art, specifically a physician or cardiologist, would be able to determine the number of stem cells that would constitute an effective dose without undue experimentation.

In some embodiments of the invention, the isolated non-senescent stem cells are activated prior to administration to a subject. Activation of the stem cells may be accomplished by exposing the isolated stem cells to one or more cytokines, such as hepatocyte growth factor (HGF), insulin-like growth factor-1 (IGF-1), or variant thereof.

HGF positively influences stem cell migration and homing through the activation of the c-Met receptor (Kollet et al. (2003) J. Clin. Invest. 112: 160-169; Linke et al. (2005) Proc. Natl. Acad. Sci. USA 102: 8966-8971; Rosu-Myles et al. (2005) J. Cell. Sci. 118: 4343-4352; Urbanek et al. (2005) Circ. Res. 97: 663-673). Similarly, IGF-1 and its corresponding receptor (IGF-1R) induce cardiac stem cell division, upregulate telomerase activity, hinder replicative senescence and preserve the pool of functionally-competent cardiac stem cells in the heart (Kajstura et al. (2001) Diabetes 50: 1414-1424; Torella et al. (2004) Circ. Res. 94: 514-524; Davis et al. (2006) Proc. Natl. Acad. Sci. USA 103: 8155-8160). In a preferred embodiment, the isolated non-senescent stem cells are contacted with hepatocyte growth factor (HGF) and/or insulin-like growth factor-1 (IGF-1). In one embodiment, HGF is present in an amount of about 0.1 to about 400 ng/ml. In another embodiment, HGF is present in an amount of about 25, about 50, about 75, about 100, about 125, about 150, about 175, about 200, about 225, about 250, about 275, about 300, about 325, about 350, about 375 or about 400 ng/ml. In another embodiment, IGF-1 is present in an amount of about 0.1 to about 500 ng/ml. In yet a further embodiment, IGF-1 is present in an amount of about 25, about 50, about 75, about 100, about 125, about 150, about 175, about 200, about 225, about 250, about 275, about 300, about 325, about 350, about 375, about 400, about 425, about 450, about 475, or about 500 ng/ml.

Some other non-limiting examples of cytokines that are suitable for the activation of the isolated non-senescent stem cells include Activin A, Bone Morphogenic Protein 2, Bone Morphogenic Protein 4, Bone Morphogenic Protein 6, Cardiotrophin-1, Fibroblast Growth Factor 1, Fibroblast Growth Factor 4, Flt3 Ligand, Glial-Derived Neurotrophic Factor, Heparin, Insulin-like Growth Factor-II, Insulin-Like Growth Factor Binding Protein-3, Insulin-Like Growth Factor Binding Protein-5, Interleukin-3, Interleukin-6, Interleukin-8, Leukemia Inhibitory Factor, Midkine, Platelet-Derived Growth Factor AA, Platelet-Derived Growth Factor BB, Progesterone, Putrescine, Stem Cell Factor, Stromal-Derived Factor-1, Thrombopoietin, Transforming Growth Factor-α, Transforming Growth Factor-β1, Transforming Growth Factor-β2, Transforming Growth Factor-β3, Vascular Endothelial Growth Factor, Wnt1, Wnt3a, and Wnt5a, as described in Kanemura et al. (2005) Cell Transplant. 14:673-682; Kaplan et al. (2005) Nature 438:750-751; Xu et al. (2005) Methods Mol. Med. 121:189-202; Quinn et al. (2005) Methods Mol. Med. 121:125-148; Almeida et al. (2005) J Biol. Chem. 280: 41342-41351; Barnabe-Heider et al. (2005) Neuron 48:253-265; Madlambayan et al. (2005) Exp Hematol 33:1229-1239; Kamanga-Sollo et al. (2005) Exp Cell Res 311:167-176; Heese et al. (2005) Neuro-oncol. 7:476-484; He et al. (2005) Am J. Physiol. 289:H968-H972; Beattie et al. (2005) Stem Cells 23:489-495; Sekiya et al. (2005) Cell Tissue Res 320: 269-276; Weidt (2004) Stem Cells 22:890-896; Encabo et al (2004) Stem Cells 22:725-740; and Buytaeri-Hoefen et al. (2004) Stem Cells 22:669-674, the entire text of each of which is incorporated herein by reference.

Functional variants of the above-mentioned cytokines can also be employed in the invention. Functional cytokine variants would retain the ability to bind and activate their corresponding receptors. Variants can include amino acid substitutions, insertions, deletions, alternative splice variants, or fragments of the native protein. For example, NK1 and NK2 are natural splice variants of HGF, which are able to bind to the c-MET receptor. These types of naturally occurring splice variants as well engineered variants of the cytokine proteins that retain function are contemplated by the invention.

In some embodiments, the administration of non-senescent stem cells to a subject in need thereof is accompanied by the administration of one or more cytokines to the heart. The cytokines may be selected from the group consisting of stem cell factor (SCF), granulocyte-colony stimulating factor (G-CSF), granulocyte-macrophage colony stimulating factor (GM-CSF), stromal cell-derived factor-1, steel factor, vascular endothelial growth factor, macrophage colony stimulating factor, granulocyte-macrophage stimulating factor, hepatocyte growth factor (HGF), insulin-like growth factor-1 (IGF-1), Interleukin-3, or any cytokine capable of the stimulating and/or mobilizing stem cells. In a preferred embodiment, the cytokines are selected from HGF, IGF-1, functional variants of HGF or IGF-1, or combinations thereof. The cytokines may be delivered simultaneously with the non-senescent stem cells. Alternatively, the administration of the cytokines may either precede or follow the administration of the non-senescent stem cells by a specified time period. The time period may be about 15 minutes, about 30 minutes, about 1 hour, about 3 hours, about 6 hours, about 12 hours, about 24 hours, about 36 hours, about 1 week, about 2 weeks, about 1 month, or about 6 months.

The cytokines may be delivered to the heart by one or more administrations. In one embodiment, cytokines are delivered by a single administration. In another embodiment, multiple administrations of the same dosage of cytokines are delivered to the heart. A preferred embodiment of the invention includes administration of multiple doses of the cytokines to the heart, such that a chemotactic gradient is foamed. A chemotactic gradient extending from the atria and/or apex of the heart to the mid-region of the left ventricle may be established by administering multiple doses of increasing cytokine concentration. Alternatively, the chemotactic gradient can be formed from the site of implantation of the non-senescent stem cells to the mid-region of the left ventricle or the border region of infarcted myocardium.

In one embodiment, at least two cytokines are used in the formation of the chemotactic gradient. In another embodiment, the concentration of the first cytokine remains constant while the concentration of the second cytokine is variable, thereby forming the chemotactic gradient. In a preferred embodiment, the chemotactic gradient is formed by multiple administrations of IGF-1 and HGF, wherein the concentration of IGF-1 remains constant and the concentration of HGF is variable. In some embodiments, the variable concentrations of HGF may range from about 0.1 to about 400 ng/ml. In other embodiments, the concentration of IGF-1 may be from about 0.1 to about 500 ng/ml.

The isolated non-senescent stem cells and cytokines may be administered to the heart by injection. The injection is preferably intramyocardial. As one skilled in the art would be aware, this is the preferred method of delivery for stem cells and/or cytokines as the heart is a functioning muscle. Injection by this route ensures that the injected material will not be lost due to the contracting movements of the heart. In another embodiments, the cardiac stem cells are administered intracoronarily.

In a further aspect of the invention, the stem cells and/or cytokines are administered by injection transendocardially or trans-epicardially. This preferred embodiment allows the cytokines to penetrate the protective surrounding membrane, necessitated by the embodiment in which the cytokines are injected intramyocardially. Another preferred embodiment of the invention includes use of a catheter-based approach to deliver the trans-endocardial injection. The use of a catheter precludes more invasive methods of delivery wherein the opening of the chest cavity would be necessitated. As one skilled in the art would appreciate, optimum time of recovery would be allowed by the more minimally invasive procedure. A catheter approach involves the use of such techniques as the NOGA catheter or similar systems. The NOGA catheter system facilitates guided administration by providing electromechanic mapping of the area of interest, as well as a retractable needle that can be used to deliver targeted injections or to bathe a targeted area with a therapeutic. Any of the embodiments of the present invention can be administered through the use of such a system to deliver injections or provide a therapeutic. One of skill in the art will recognize alternate systems that also provide the ability to provide targeted treatment through the integration of imaging and a catheter delivery system that can be used with the present invention. Information regarding the use of NOGA and similar systems can be found in, for example, Sherman (2003) Basic Appl. Myol. 13: 11-14; Patel et al. (2005) The Journal of Thoracic and Cardiovascular Surgery 130:1631-38; and Perrin et al. (2003) Circulation 107: 2294-2302; the text of each of which are incorporated herein in their entirety. In another embodiment, the isolated non-senescent cardiac stem cells are administered by an intracoronary route of administration. One of skill in the art will recognize other useful methods of delivery or implantation which can be utilized with the present invention, including those described in Dawn et al. (2005) Proc. Natl. Acad. Sci. USA 102, 3766-3771, the contents of which are incorporated herein in their entirety.

The methods of the present invention are useful for the treatment of cardiovascular disease, including, but not limited to, atherosclerosis, ischemia, hypertension, restenosis, angina pectoris, rheumatic heart disease, congenital cardiovascular defects, age-related cardiomyopathy, and arterial inflammation and other disease of the arteries, arterioles and capillaries. Specifically, the methods of the present invention provide for the repair and/or regeneration of damaged myocardium resulting from one of the diseases listed above or from the general decline of myocardial cells with age.

The present invention also encompasses methods of preventing or treating heart failure in a subject comprising administering isolated non-senescent adult cardiac stem cells into said subject's heart and administering an angiotensin II receptor antagonist. In one embodiment, the non-senescent adult cardiac stem cells contain immortal DNA. In another embodiment, the non-senescent adult cardiac stem cells are activated prior to administration by exposure to one or more cytokines as described herein. In yet another embodiment, one or more cytokines are administered to the heart to form a chemotactic gradient causing said administered non-senescent adult cardiac stem cells to migrate to areas of myocardial damage. In another embodiment, said one or more cytokines are HGF, IGF-1, or variants thereof.

The renin-angiotensin system (RAS) is a hormone system that facilitates the regulation of blood pressure and extracellular volume in the body. When renal perfusion drops, cells in the kidney release the enzyme renin. Renin cleaves angiotensinogen, an inactive precursor peptide secreted by the liver, into angiotensin I. Angiotensin I is subsequently converted into angiotensin II (Ang II) by angiotensin-converting enzyme (ACE), which is predominantly found in the lungs. Ang II produces many effects, including vasoconstriction and secretion of aldosterone and vasopressin, through activation of the AT1 receptor. Ang II has been implicated in the age-dependent accumulation of oxidative damage in the heart (Fiordaliso et al. (2001) Diabetes 50: 2363-2375; Kajstura et al. (2001) Diabetes 50: 1414-1424), and has been reported to induce senescence and decrease the number and function of endothelial progenitor cells (Kobayashi et al. (2006) Hypertens. Res. 29: 449-455). In addition, Ang II triggers apoptosis in myocytes (Leri et al. (1998) J. Clin. Invest. 101: 1326-1342) and may contribute to the progression of heart failure (McMurray et al. (2003) Lancet 362: 767-771). In fact, inhibition of AT1 receptors has been shown to improve the clinical outcome of patients with chronic heart failure and prolong life in humans (McMurray et al. (2003) Lancet 362: 767-771).

The invention provides for methods of preventing heart failure and/or treating chronic heart failure in a subject by administering an Ang II receptor antagonist in combination with administration of non-senescent adult cardiac stem cells to the subject's heart. Preferably, the Ang II receptor antagonist is an antagonist of the AT1 receptor. Some non-limiting examples of Ang II receptor antagonists that would be encompassed by the invention include Valsartan, Telmisartan, Losartan, Irbesartan, Olmesartan, Candesartan, and Eprosartan.

In addition, inhibitors of angiotensin converting enzyme (ACE) may be administered in addition to or instead of the Ang II receptor antagonist. As described above, ACE converts angiotensin I into angiotensin II. Inhibition of this enzyme would lead to decreased levels of Ang II and thus reduce the deleterious effects of Ang II on cardiac stem cells. ACE inhibitors which may be used in the methods of the prevent invention include, but are not limited to, Benazepril, Enalapril, Lisinopril, Captopril, Fosinopril, Ramipril, Perindopril, Quinapril, Moexipril, and Trandolapril.

The Ang II receptor antagonists or ACE inhibitors may be administered to the subject in multiple doses subsequent to the administration of the non-senescent adult cardiac stem cells. The antagonists or inhibitors may be taken on a routine schedule for a set period of time. For example, the inhibitors may be taken once daily for about 1 month, about 2 months, about 3 months, about 6 months, about 12 months, or about 24 months after administration of the non-senescent adult cardiac stem cells. Other dosing schedules may be employed. One of skill in the art, particularly a physician or cardiologist, would be able to determine the appropriate dose and schedule for the administration of the ACE inhibitors or Ang II receptor antagonists.

Preferably, one or more symptoms of heart failure is reduced or alleviated following administration of the non-senescent cardiac stem cells and the angiotensin II receptor antagonist and/or ACE inhibitor. Symptoms of heart failure include, but are not limited to, fatigue, weakness, rapid or irregular heartbeat, dyspnea, persistent cough or wheezing, edema in the legs and feet, and swelling of the abdomen.

The invention also comprehends methods for preparing compositions, such as pharmaceutical compositions, including non-senescent adult stem cells and/or at least one cytokine, for instance, for use in inventive methods for treating cardiovascular disease, heart failure or other cardiac conditions. In one embodiment, the pharmaceutical composition comprises isolated non-senescent human cardiac stem cells and a pharmaceutically acceptable carrier, wherein said isolated human cardiac stem cells are c-kit positive, IGF-1 receptor positive, and have telomeres greater than 5 kbp in length. In another embodiment, the cardiac stem cells have telomeres greater than 7 kbp in length. In still another embodiment, the cardiac stem cells have telomeres greater than 9 kbp in length. In some embodiments, the non-senescent cardiac stem cells are p16$^{INK4a}$ negative.

In certain embodiments, the pharmaceutical compositions comprise non-senescent adult cardiac stem cells that contain immortal DNA. In one embodiment, the pharmaceutical compositions can comprise other adult cardiac stem cells or other stem cell types (e.g. hematopoietic stem cells) in addition to the non-senescent adult cardiac stem cells containing the immortal DNA. Preferably, such pharmaceutical compositions comprise at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99% of the non-senescent adult cardiac stem cells containing the immortal DNA. In other embodiments, the pharmaceutical compositions comprise pure (i.e. 100%) non-senescent adult cardiac stem cells containing the immortal DNA.

In a preferred aspect, the methods and/or compositions, including pharmaceutical compositions, comprise effective amounts of non-senescent adult cardiac stem cells or two or more cytokines in combination with an appropriate pharmaceutical agent useful in treating cardiac and/or vascular conditions.

In an additionally preferred aspect, the pharmaceutical compositions of the present invention are delivered via injection. These routes for administration (delivery) include, but are not limited to, subcutaneous or parenteral including intravenous, intraarterial (e.g. intracoronary), intramuscular, intraperitoneal, intramyocardial, transendocardial, trans-epicardial, intranasal administration as well as intrathecal, and infusion techniques. Accordingly, the pharmaceutical composition is preferably in a form that is suitable for injection.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion, and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

The pharmaceutical compositions of the present invention, e.g., comprising a therapeutic dose of non-senescent cardiac stem cells, can be administered to the subject in an injectable formulation containing any compatible carrier, such as various vehicles, adjuvants, additives, and diluents; or the compounds utilized in the present invention can be administered parenterally to the subject in the form of slow-release subcutaneous implants or targeted delivery systems such as monoclonal antibodies, iontophoretic, polymer matrices, liposomes, and microspheres.

The pharmaceutical compositions utilized in the present invention can be administered orally to the subject. Conventional methods such as administering the compounds in tablets, suspensions, solutions, emulsions, capsules, powders, syrups and the like are usable. Known techniques which deliver the compound orally or intravenously and retain the biological activity are preferred.

In one embodiment, a composition of the present invention can be administered initially, and thereafter maintained by further administration. For instance, a composition of the invention can be administered in one type of composition and thereafter further administered in a different or the same type of composition. For example, a composition of the invention can be administered by intravenous injection to bring blood levels to a suitable level. The subject's levels are then maintained by an oral dosage form, although other forms of administration, dependent upon the subject's condition, can be used.

The quantity of the pharmaceutical composition to be administered will vary for the subject being treated. In one embodiment, $2 \times 10^4$-$1 \times 10^5$ adult cardiac stem cells and 50-500 µg/kg per day of a cytokine or variant of said cytokine are administered to the subject. However, the precise determination of what would be considered an effective dose may be based on factors individual to each subject, including their size, age, area of damaged myocardium, and amount of time since damage. Thus, the skilled artisan can readily determine the dosages and the amount of compound and optional additives, vehicles, and/or carrier in compositions to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Examples of compositions comprising a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Pharmaceutical compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like (e.g., for transdermal administration) and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

The inventive compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular subject, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

The pharmaceutical compositions of the present invention are used to treat heart failure and cardiovascular diseases, including, but not limited to, atherosclerosis, ischemia, hypertension, restenosis, angina pectoris, rheumatic heart disease, congenital cardiovascular defects and arterial inflammation and other diseases of the arteries, arterioles and capillaries or related complaint. Accordingly, the invention involves the administration of non-senescent adult stem cells as herein discussed, alone or in combination with one or more cytokines or variant of said cytokine, as herein discussed, for the treatment or prevention of any one or more of these conditions or other conditions involving weakness in the heart. And, advantageous routes of administration involves those best suited for treating these conditions, such as via injection, including, but are not limited to subcutaneous or parenteral including intravenous, intraarterial, intramuscular, intraperitoneal, intramyocardial, transendocardial, trans-epicardial, intranasal administration as well as intrathecal, and infusion techniques.

This invention is further illustrated by the following examples that should not be construed as limiting. The contents of all references, patents and published patent applications cited throughout this application, as well as the Figures, are incorporated herein by reference for all purposes.

EXAMPLES

Example 1

A Functional Pool of Cardiac Stem Cells is Preserved in the Aging Heart

A. Characterization of Cardiac Stem Cells in the Old Heart

Cardiac stem cells (CSCs), also known as cardiac progenitor cells (CPCs), are lineage-negative ($Lin^{NEG}$) cells that express the stem cell antigens c-kit, MDR-1 and Sca-1, alone or in combination (Beltrami et al. (2003) Cell 114: 763-776). $Lin^{NEG}$-CPCs are clustered with early committed cells in the cardiac niches (Urbanek et al. (2006) Proc. Natl. Acad. Sci. USA 103: 9226-9231), which are predominantly located in the atria and apex although they are also present at the base-mid-region of the left ventricle (LV) (see FIGS. 1A and 1B). To define whether myocardial aging is conditioned by alterations in CPC function with accumulation of old myocytes, we measured the number of CPCs together with the expression of the aging-associated protein $p16^{INK4a}$ in rats at 4, 12, 20 and 28 months of age. These ages correspond to young-adult, fully mature-adult, aged and senescent animals, respectively.

This analysis was restricted to c-kit-positive-CPCs in the atria, base-mid-region and apex of the LV in rats at 4, 12, 20 and 28 months of age. CPCs were identified by employing an antibody against c-kit (R&D Systems). Cell phenotype was defined by immunocytochemistry. CPCs were tested for markers of cardiac, skeletal muscle, neural and hematopoietic cell lineages to detect $Lin^{NEG}$-CPCs (Beltrami et al. (2003) Cell 114: 763-776; Linke et al. (2005) Proc. Natl. Acad. Sci. USA 102: 8966-8971; Urbanek et al. (2005) Cir. Res. 97: 663-673). To recognize myocyte progenitors and precursors the presence of c-kit together with transcription factors and cytoplasmic proteins specific of myocytes was determined. A complete list of antibodies used is shown below in Table 1.

TABLE 1

Antibodies and their labeling

| Protein | Antibody | Labeling | Fluorochrome(s) |
|---|---|---|---|
| Stem cell markers | | | |
| c-kit | goat polyclonal | direct and indirect | F, T, Cy5, QD655 |
| MDR-1 | mouse monoclonal | direct and indirect | F, T, Cy5, QD655 |
| Sca-1 | rat monoclonal | direct and indirect | F, T, Cy5, QD655 |
| Structural proteins of myocardial cells | | | |
| α-sarcomeric actin | mouse monoclonal | direct and indirect | F, T, Cy5, QD655 |
| β-myosin heavy chain | mouse monoclonal | direct and indirect | T, QD655 |
| von Willebrand factor | sheep polyclonal | direct and indirect | T, Cy5, QD655 |
| α-smooth muscle actin | mouse monoclonal | direct and indirect | F, T, Cy5, QD655 |
| Transcription factors of myocardial cells | | | |
| MEF2C | goat polyclonal | direct and indirect | T, Cy5, QD655 |
| GATA-4 | mouse monoclonal | direct and indirect | T, Cy5, QD655 |
| Nkx2.5 | goat polyclonal | direct and indirect | T, Cy5, QD655 |
| Growth factors | | | |
| HGF | rabbit polyclonal | direct and indirect | T, Cy5, QD605 |
| IGF-1 | goat polyclonal | direct and indirect | T, Cy5, QD605 |
| AngII | rabbit polyclonal | direct and indirect | T, Cy5, QD605 |
| c-Met | rabbit polyclonal | direct and indirect | T, Cy5, QD605 |
| IGF-1R | mouse monoclonal | direct and indirect | T, Cy5, QD605 |
| AT1 receptor | rabbit polyclonal | direct and indirect | T, Cy5, QD605 |
| Other stainings | | | |
| Ki67 | rabbit polyclonal | direct and indirect | Cy5, QD655 |
| BrdU | mouse monoclonal | direct and indirect | Cy5, QD655 |
| Phospho-H3 | rabbit polyclonal | direct and indirect | Cy5, QD655 |
| $p16^{INK4a}$ | mouse monoclonal | direct and indirect | Cy5, QD655 |
| 8-OH-dG | rabbit polyclonal | direct and indirect | Cy5, QD655 |
| EGFP | rabbit polyclonal | direct and indirect | Cy5, QD655 |
| Telomeres | | direct | F |
| TUNEL | TdT/dUTP | direct | F |
| Laminin | rabbit polyclonal | direct and indirect | Cy5, QD655 |

Direct labeling: Primary antibody conjugated with the fluorochrome. Indirect labeling: species-specific secondary antibody conjugated with the fluorochrome. F: fluorescein isothiocyanate, T: tetramethyl rhodamine isothiocyanate, Cy5: cyanine 5, QD655: quantum dots with emission at 655 nm, QD605: quantum dots with emission at 605 nm.

Morphometric measurements of CPCs, myocyte progenitors and myocyte precursors were obtained by counting at confocal microscopy the number of CPCs or the two other cell categories per unit area, N(cpc)A, of LV and atrial myocardium. Additionally, the number of CPCs per unit volume of myocardium, N(cpc)V, and the average diameter of CPCs, D(cpc), were obtained utilizing the Schwartz-Saltykov methodology (Anversa and Olivetti (2002) in Handbook of Physiology, E. Page, H. A. Fozzard and R. J. Solaro, eds., New York: Oxford Univ. Press, Sect. 2, Vol. 1:75-144; Rota et al. (2006) Circ. Res. 99: 42-52; Urbanek et al. (2006) Proc. Natl. Acad. Sci. USA 103: 9226-9231). An identical approach was followed for the measurements of myocyte progenitors and precursors. Additionally, the number of CPCs that reached replicative senescence and irreversible growth arrest (Janzen et al. (2006) Nature 443: 421-426; Molofsky et al. (2006) Nature 443: 448-452; Krishnamurthy et al. (2006) Nature 443: 453-457) was evaluated by the expression of the senescence-associated protein $p16^{INK4a}$. Also, the fraction of CPCs undergoing apoptosis (Linke et al. (2005) Proc. Natl. Acad. Sci. USA 102: 8966-8971; Rota et al. (2006) Cir. Res. 99: 42-52; Kajstura et al. (2001) Diabetes 50: 1414-1424) was evaluated by the hairpin 1 to establish the number of functionally-competent CPCs (Urbanek et al. (2005) Proc. Natl. Acad. Sci. USA 102: 8692-8697; Rota et al. (2006) Cir. Res. 99: 42-52) in the various anatomical areas of the heart with aging.

Figure 2:
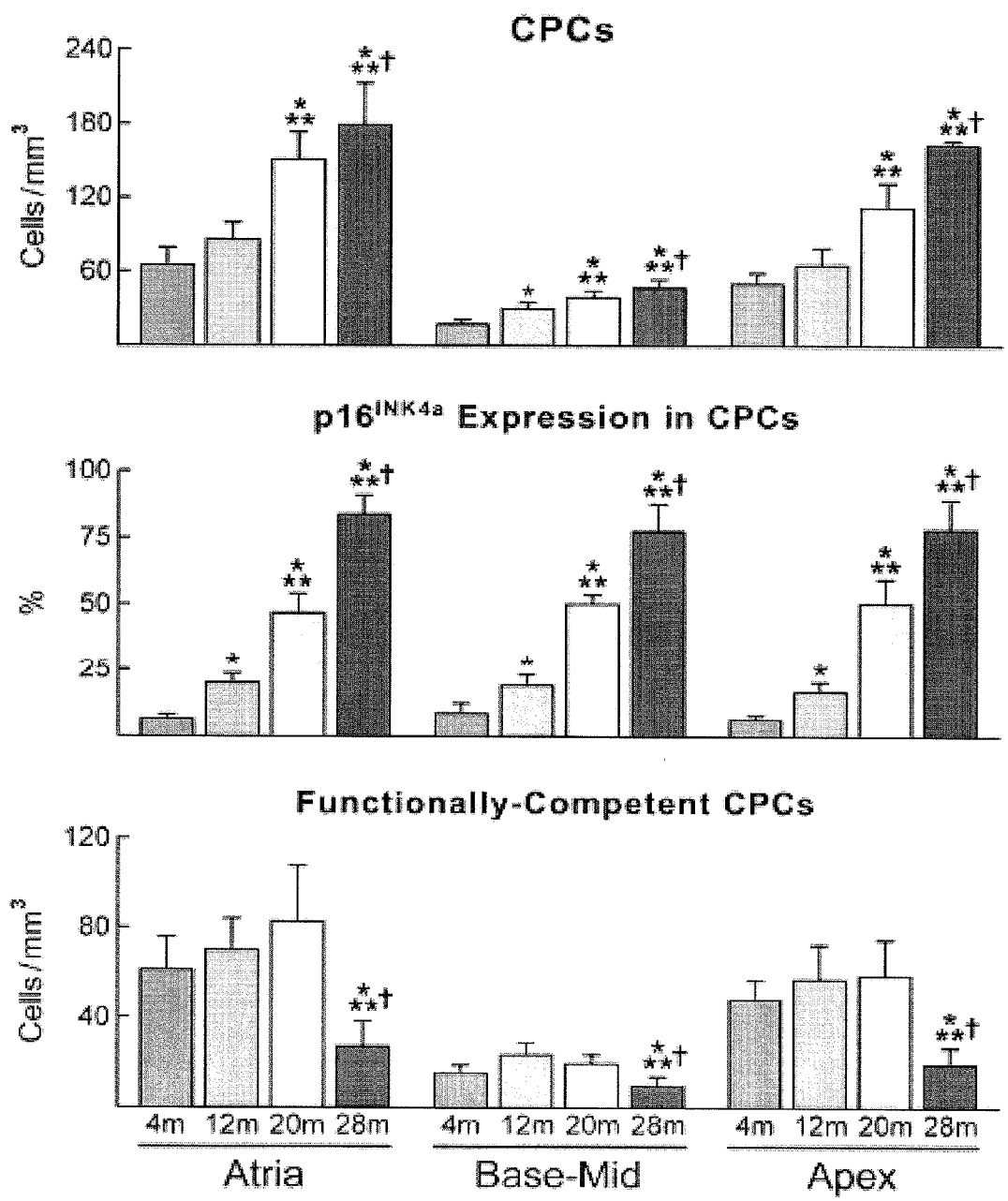
FIG. 2. CPCs/mm³ myocardium (upper panel), fraction of $p16^{INK4a}$-positive-CPCs (central panel) and functionally-competent CPCs/mm³ myocardium (lower panel). Values of $p16^{INK4a}$-CPCs include apoptotic CPCs (see FIG. 4).
Figure 3:
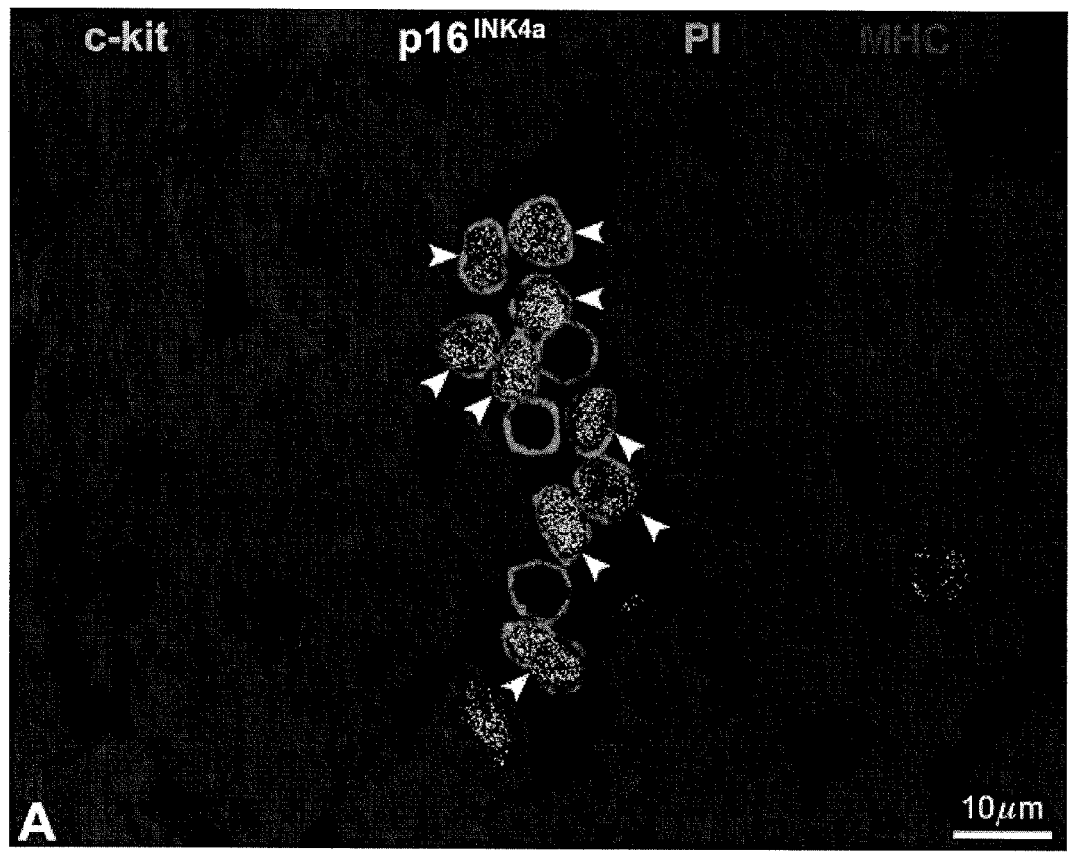
FIG. 3. Cluster of c-kit-positive CPCs (green) in the left ventricle (LV) at 20 months. Several CPCs express the senescence-associated protein $p16^{INK4a}$ (white; arrowheads). Myocytes, MHC (red). Propidium iodide (PI, blue).
Figure 4:
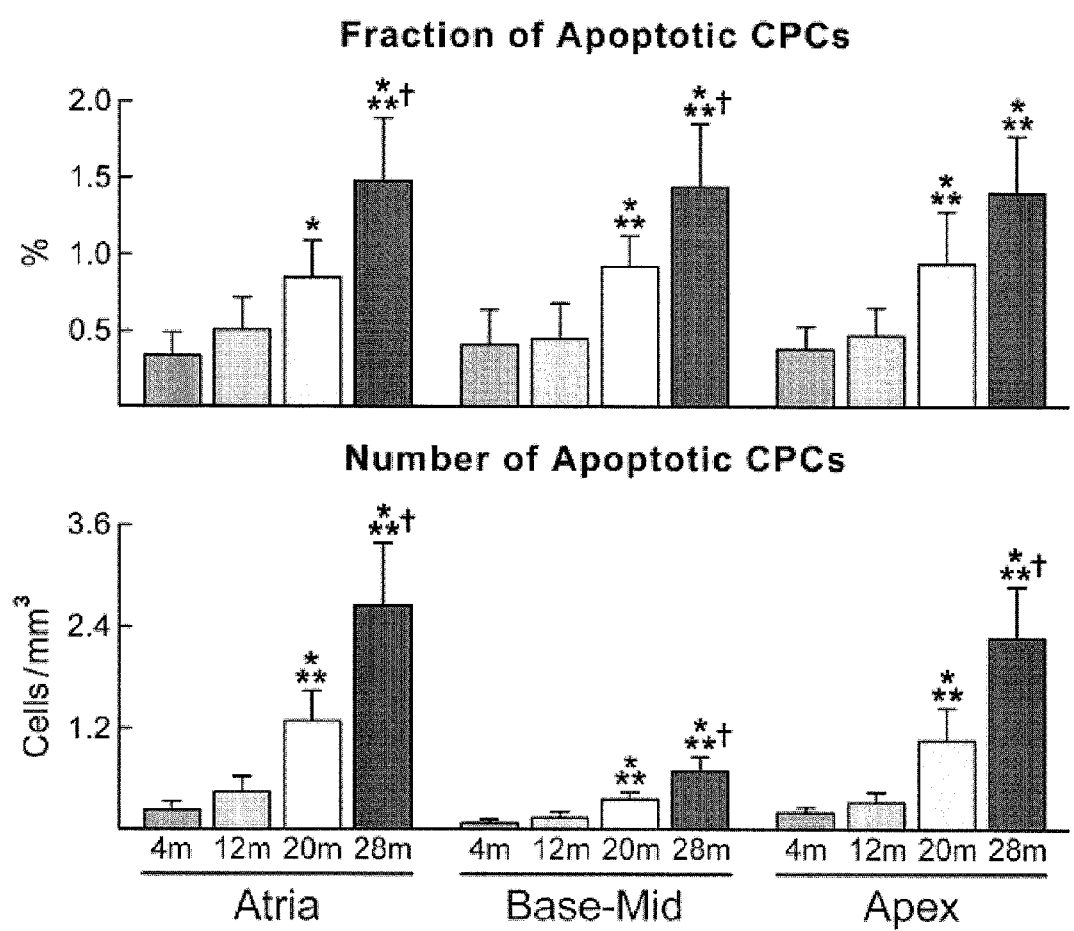
FIG. 4. Percentage (upper panel) and number/mm³ myocardium (lower panel) of apoptotic CPCs. *p<0.05 versus 4 months (4 m); **p<0.05 versus 12 months (12 m); †p<0.05 versus 20 months (20 m).

From 4 to 28 months, the number of CPCs in the heart increased ~2.9-fold (FIG. 2). However, $p16^{INK4a}$, which promotes permanent withdrawal of stem cells from the cell cycle in vivo (Janzen et al. (2006) Nature 443: 421-426; Molofsky et al. (2006) Nature 443: 448-452; Krishnamurthy et al. (2006) Nature 443: 453-457), was detected in a significant fraction of CPCs (see FIG. 3). The percentage of $p16^{INK4a}$-positive-CPCs increased from ~6% at 4 months to ~81% at 28 months (FIG. 2). Similarly, apoptosis increased dramatically with age and was restricted to $p16^{INK4a}$-positive-CPCs (FIG. 4). Because of these variables, the number of functional CPCs remained essentially constant up to 20 months but decreased sharply at 28 months (FIG. 2). Thus, the expansion of the CPC compartment with age is characterized by accumulation of old, non-replicating, dying $p16^{INK4a}$-positive-cells. These data are paralleled by a similar increase in the number of senescent, apoptotic $p16^{INK4a}$-positive-myocytes (Kajstura et al. (1996) Am. J. Physiol. 271: H1215-H1228; Kajstura et al. (2000) Am J. Pathol. 156: 813-819).

Figure 5:
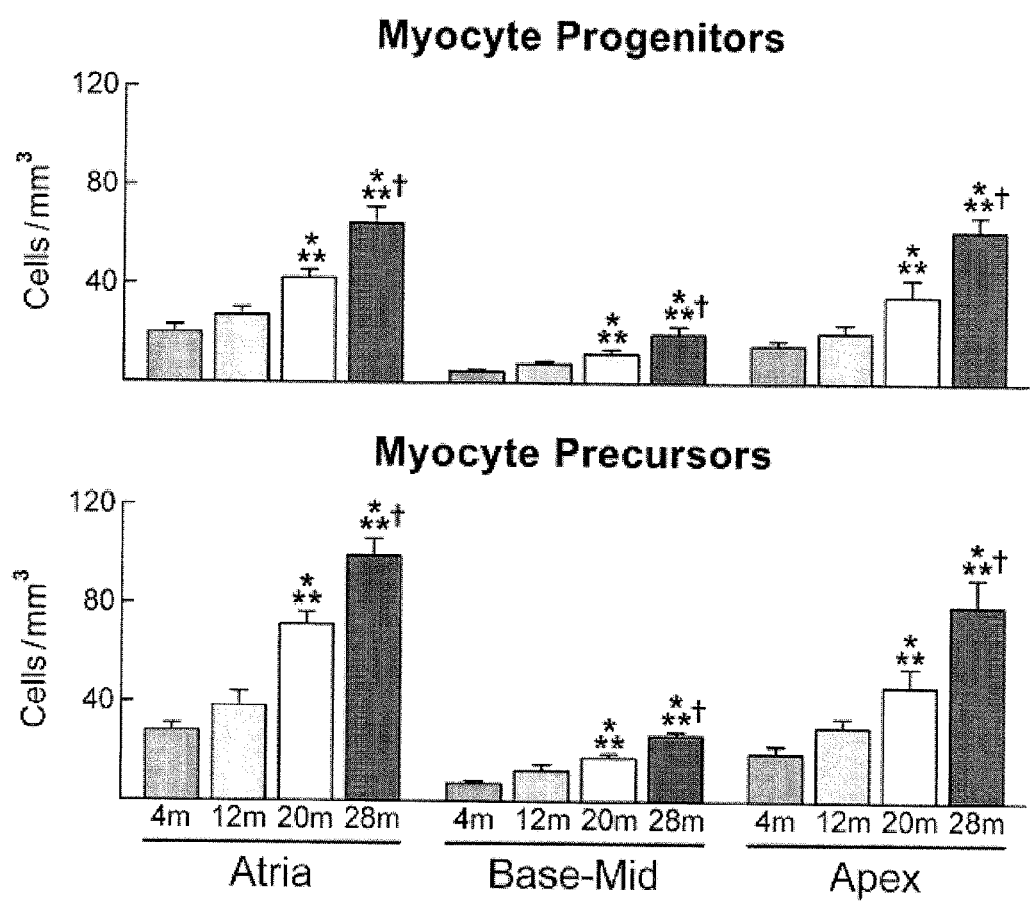
FIG. 5. Myocyte progenitors (c-kit-positive-MEF2C-positive-CPCs/mm³ myocardium) and precursors (c-kit-positive-MEF2C-positive-MHC-positive-CPCs/mm³ myocardium). *p<0.05 versus 4 months (4 m); **p<0.05 versus 12 months (12 m); †p<0.05 versus 20 months (20 m).

Myocyte progenitors-precursors correspond to differentiating CPCs that express c-kit together with transcription factors and cytoplasmic proteins specific of myocytes, indicating the linear relationship between CPCs and forming myocytes. CPCs positive for the myocyte transcription factor MEF2C, i.e., myocyte progenitors, or both MEF2C and the sarcomeric protein cardiac-myosin-heavy-chain (MHC), i.e., myocyte precursors, increased with age indicating that the generation of myocytes was enhanced in the old heart (FIG. 5).

A pulse-chase-BrdU-labeling-assay was performed (Urbanek et al. (2006) Proc. Natl. Acad. Sci. USA 103: 9226-9231) to assess the growth behavior of CPCs and extent of myocyte progeny formed by CPC differentiation. The objective was to answer the question whether the senescent heart contains a pool of functionally-competent CPCs which may be activated to promote a differentiated progeny. Therefore, rats at 4 and 27 months were exposed to BrdU for 7 days and BrdU positive CPCs and myocytes were measured at 7 days and after 12 weeks of chasing. Specifically, rats at 4 and 27 months were divided into two groups each. In the first case, rats at 4 and 27 months were exposed to BrdU in the drinking water for 7 days and subsequently sacrificed and studied. In the second case, rats at 4 and 27 months were exposed to BrdU in the drinking water for 7 days and studied after a chasing period of 12 weeks, at 7 and 30 months, respectively. Bright- and dim-BrdU-labeled-CPCs were discerned by fluorescence intensity to score long-term-label-retaining-CPCs, thus providing a functional identification of resident stem cells (Tumbar et al. (2004) Science 303: 359-363). Levels of fluorescence >4,000 and <2,000 units (pixel×average intensity) were considered representative of bright and dim cells, respectively (Urbanek et al. (2006) Proc. Natl. Acad. Sci. USA 103: 9226-9231). Bright- and dim-BrdU-labeled-myocytes at 7 days and 12 weeks were also determined. In addition, the myocyte mitotic index (Urbanek et al. (2005) Proc. Natl. Acad. Sci. USA 102: 8692-8697; Urbanek et al. (2006) Proc. Natl. Acad. Sci. USA 103: 9226-9231) was also measured by the expression of phospho-H3 in young and old hearts to have a quantitative estimate of the actual population of amplifying myocytes in the LV myocardium (Urbanek et al. (2005a) Cir. Res. 97:663-673; Anversa et al. (2006) Circulation 113: 1451-1463).

Figure 6:
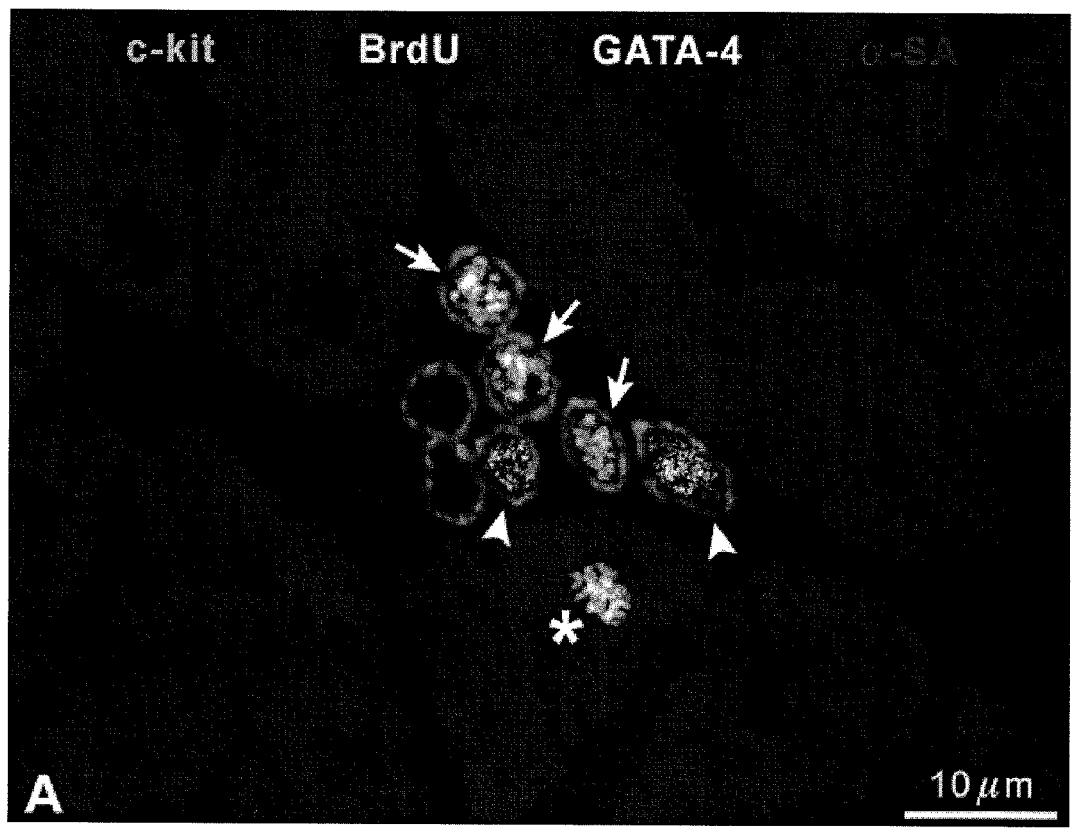
FIG. 6. Old heart after 7 days of BrdU labeling: atrial niche in which 3 of the 7 CPCs (c-kit, green) are BrdU-bright (yellow; arrows). BrdU-bright CPC are Lin$^{neg}$ (GATA-4-negative). A BrdU-bright myocyte is also present (asterisk).
Figure 7:
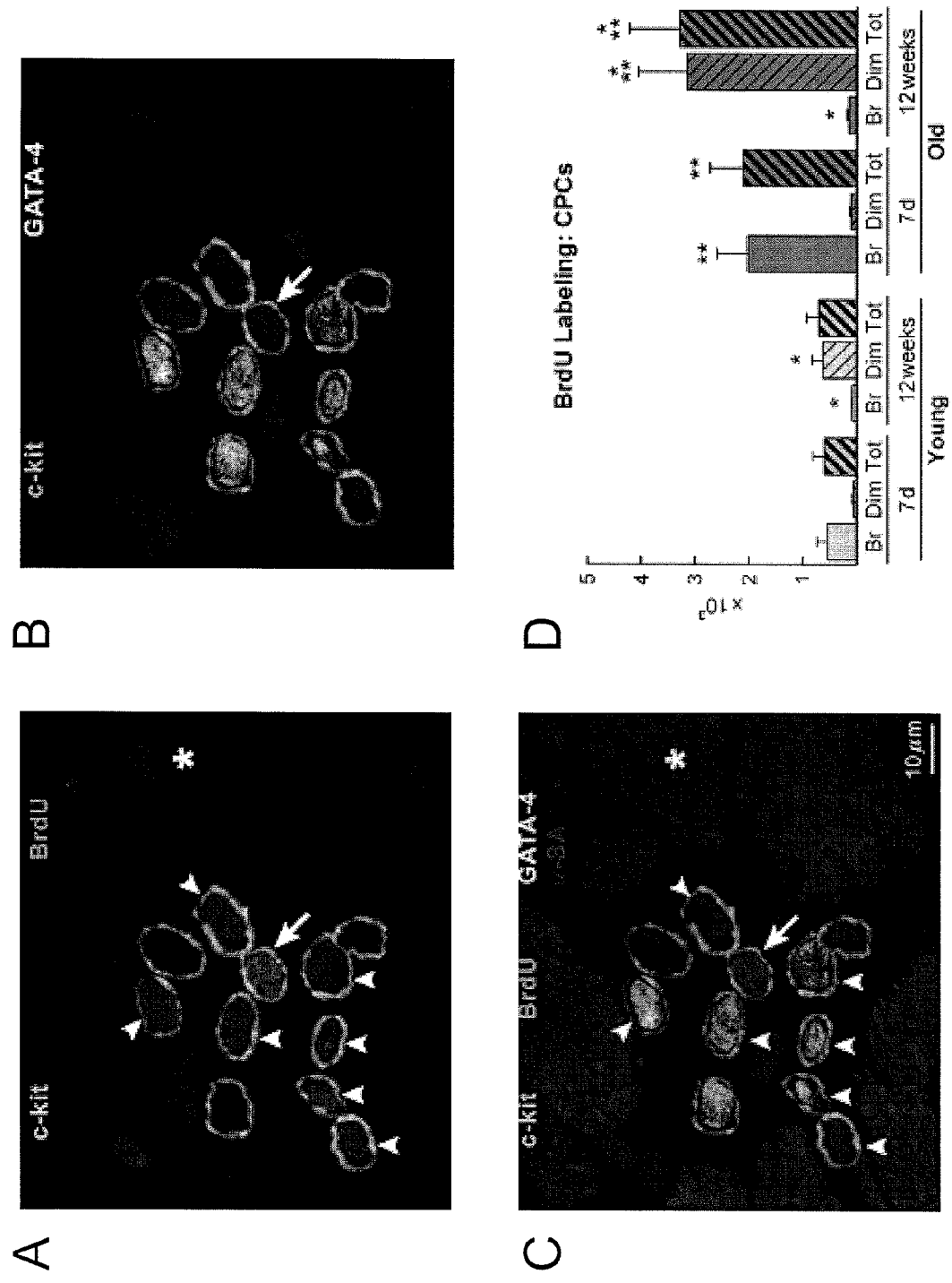
FIG. 7. (A) Old heart after 12 weeks of chasing: atrial niche in which 1 of the 11 CPCs (c-kit, green) is BrdU-bright (magenta; arrow) and 7 are BrdU-dim (arrowheads). (B) The BrdU-bright-CPC is Lin$^{neg}$ (GATA-4-negative). (C) One BrdU-dim myocyte is also visible (α-sarcomeric actin, α-SA, asterisk). Several non-myocyte nuclei are also labeled by BrdU. (D) BrdU-bright- and dim-CPCs at 7 days and 12 weeks.

The number of BrdU-bright-CPCs detected at 7 days (FIG. 6) decreased 86% and 93% after 12 weeks of chasing in young and old animals, respectively. At 7 days, 532 and 2,012 BrdU-bright-CPCs were found in young and old hearts, respectively. Corresponding values 12 weeks later were 73 and 140, which constituted the slow-cycling stem cell pool in the myocardium (FIG. 7). From 7 days to 12 weeks, BrdU-dim-CPCs increased 10-fold in young and 32-fold in old hearts. The aggregate number of BrdU-bright- and BrdU-dim-CPCs did not change in 12 weeks in young but increased significantly in old animals. Thus, the growth kinetics of CPCs preserves the pool of primitive cells in the young heart but expands this compartment in the old myocardium.

Figure 8:
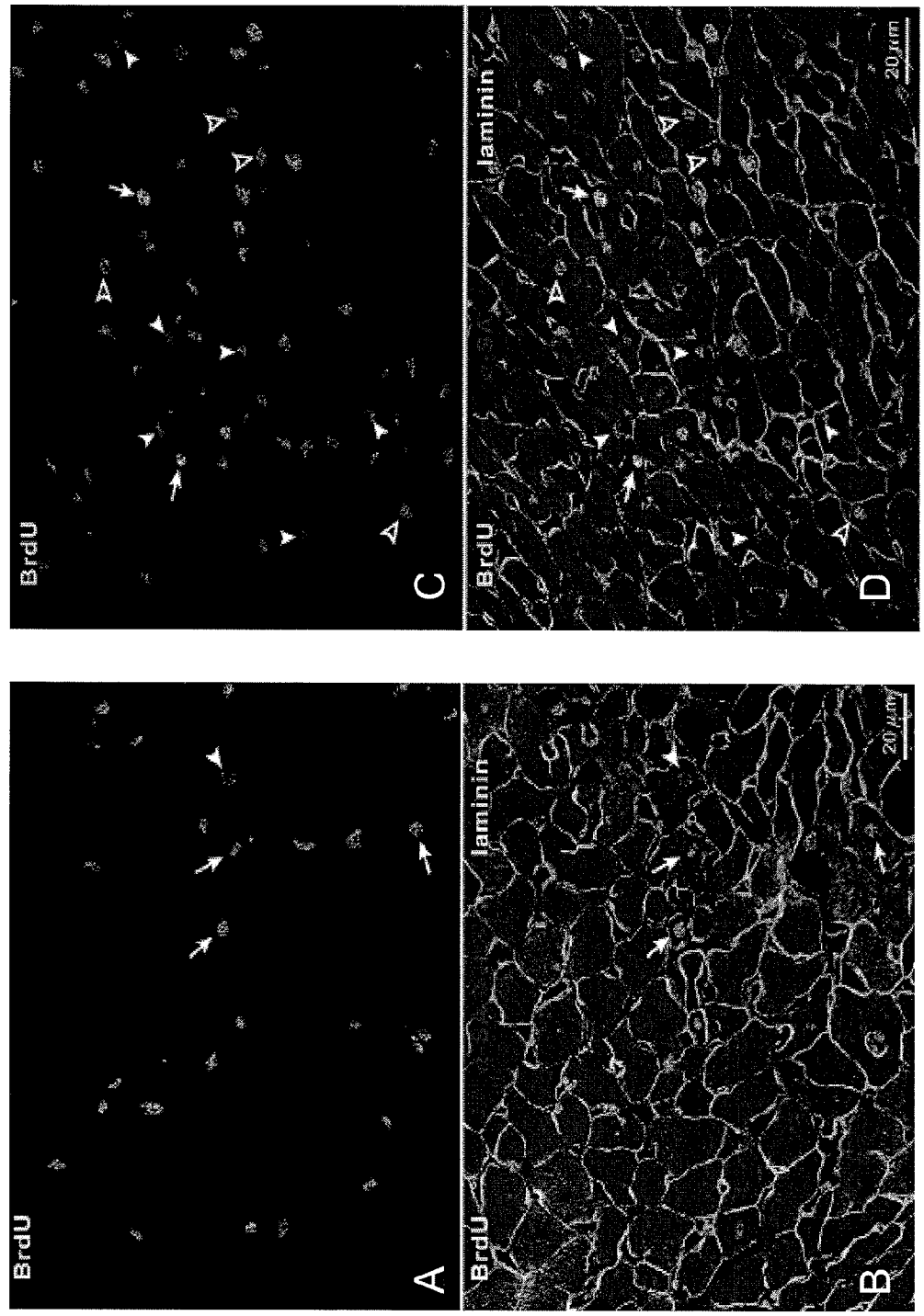
FIG. 8. (A and B) Old LV myocardium containing BrdU (yellow) bright-(arrows), and dim-(arrowhead) myocytes (α-SA, red) at 7 days. Several non-myocyte nuclei are also labeled by BrdU. Laminin, white. (C and D) Old LV myocardium containing BrdU (yellow) bright-(arrows), intermediate-(open-arrowheads) and dim-(arrowheads) myocytes (α-SA, red) at 12 weeks. Laminin, white.

Similarly, BrdU-positive-myocytes were measured at 7 days (FIGS. 8A and B) and 12 weeks (FIGS. 8C and D). BrdU-bright-myocytes at 12 weeks were cells that experienced a limited number of divisions while BrdU-dim-myocytes were considered the progeny of CPCs, which became BrdU-positive at the time of exposure and gave rise to a large number of committed cells. Cells with intermediate levels of BrdU (greater than 2,000 but less than 4,000 units of pixel× average intensity) were assumed to represent amplifying myocytes which incorporated BrdU at the time of exposure and continued to divide and differentiate.

Figure 9:
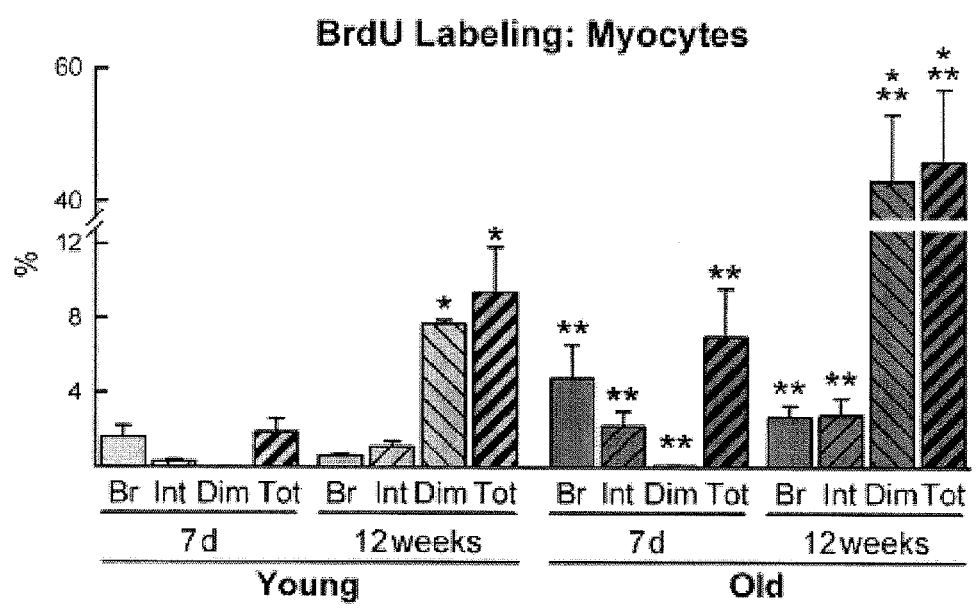
FIG. 9. BrdU-bright-, intermediate- and dim-myocytes at 7 days and 12 weeks. *p<0.05 versus 7 days (7 d); **p<0.05 versus young hearts.
Figure 10:
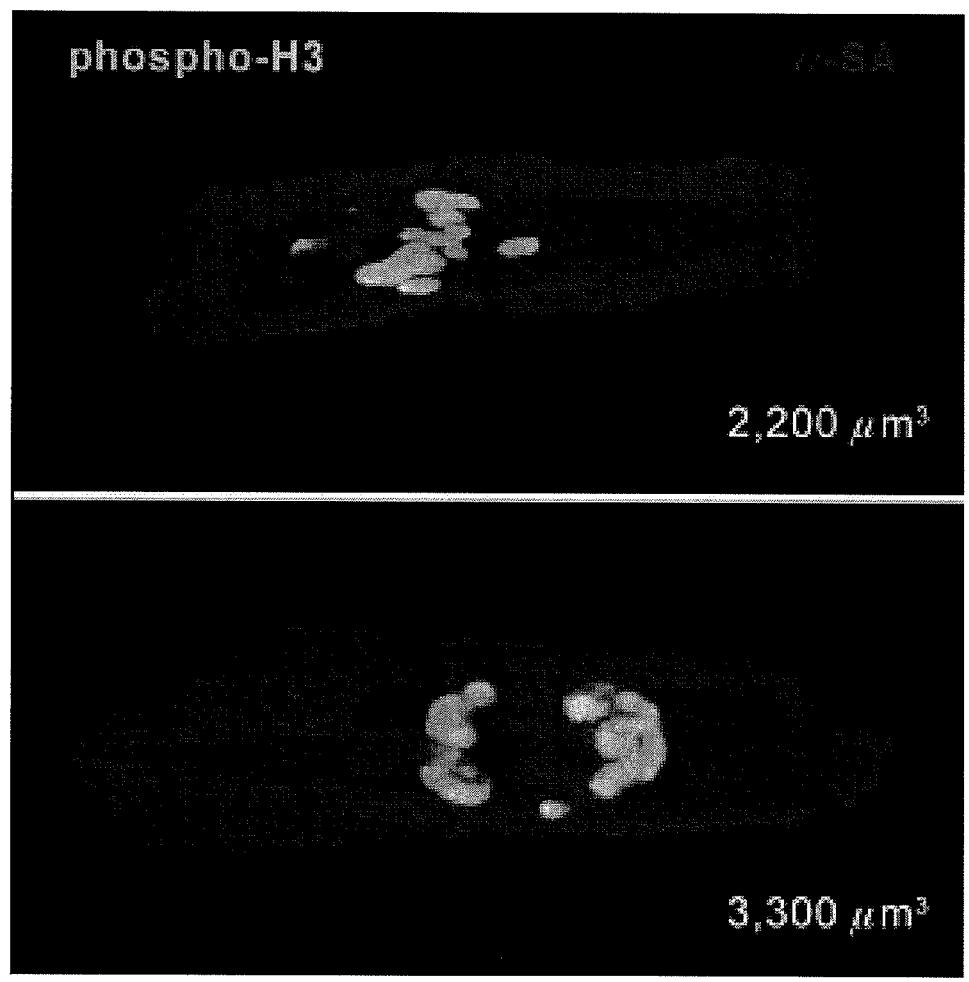
FIG. 10. Metaphase and anaphase chromosomes in dividing myocytes (α-SA, red) isolated from young (upper panel) and old (lower panel) hearts. Phospho-H3 (green) is present.
Figure 11:
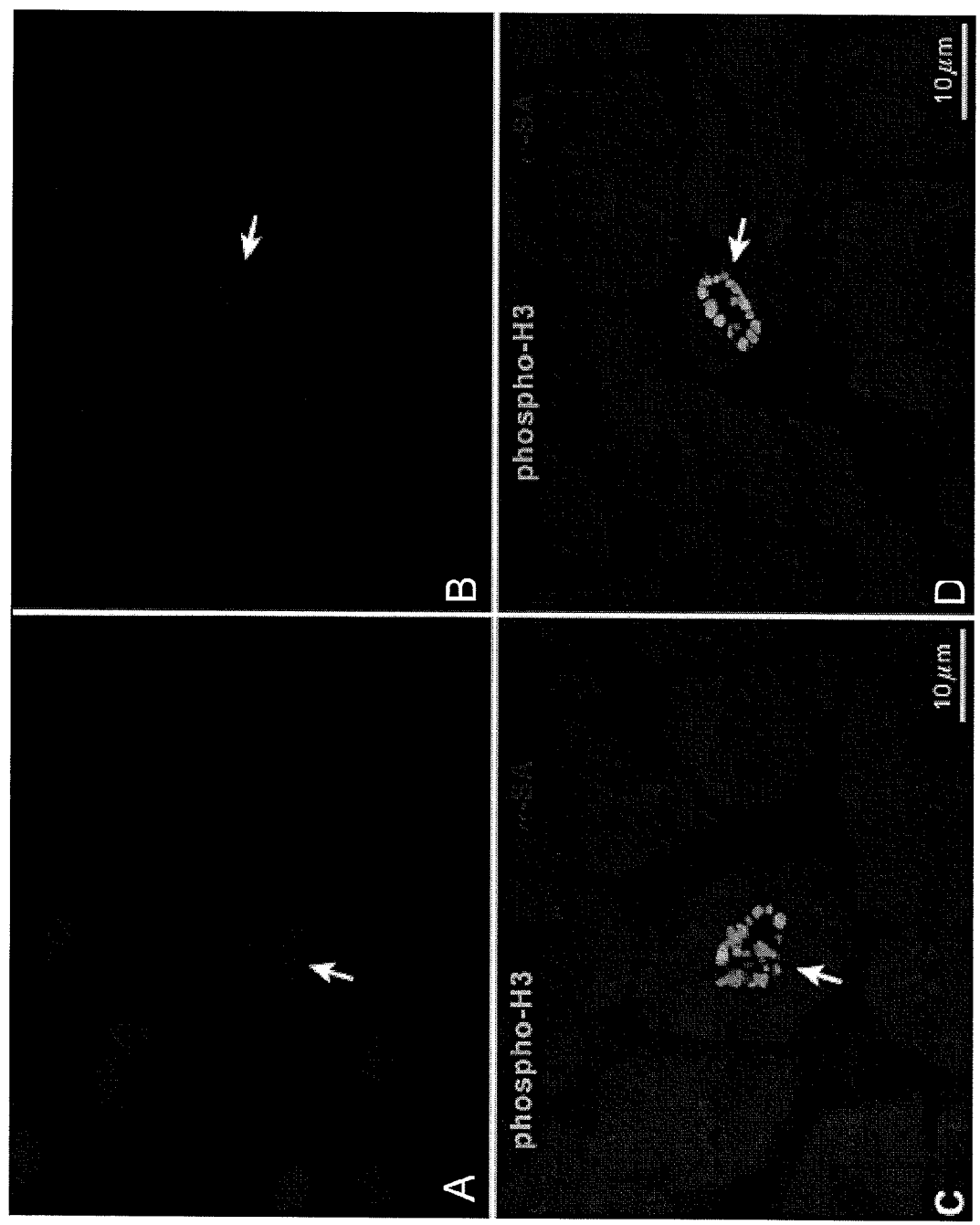
FIG. 11. Metaphase chromosomes (A and B: blue, PI; arrows) positive for phospho-H3 (C and D: green) are apparent in small dividing cardiomyocytes (α-SA, red) in LV myocardium of young (A and C) and old (B and D) hearts.
Figure 12:
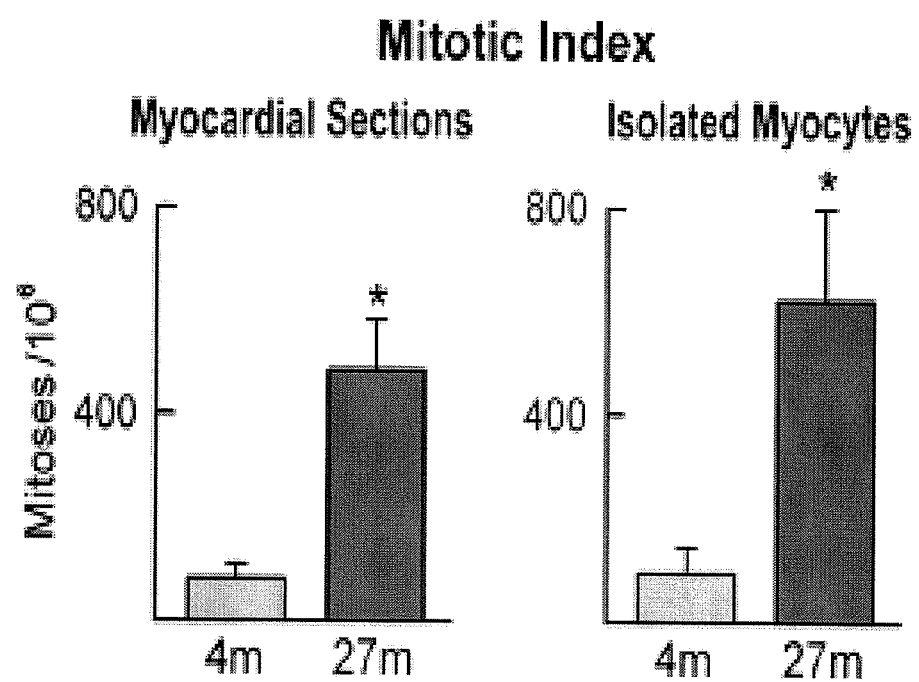
FIG. 12. Myocyte mitotic index in tissue sections (left panel) and isolated myocytes (right panel). *p<0.05 versus young hearts.

Scattered BrdU-positive myocytes were observed after 7 days of labeling in young and old animals. Following 12 weeks of chasing, clusters of BrdU-dim-myocytes together with BrdU-bright-myocytes were observed in both groups but predominantly in old animals. The percentage of BrdU-positive-myocytes was 5.3-fold higher in old than in young hearts (FIG. 9). In both cases, the number of BrdU-bright-myocytes detected at 7 days decreased markedly after 12 weeks. Conversely, BrdU-dim-myocytes increased. The higher level of myocyte formation in old hearts was confirmed by the myocyte mitotic index measured in situ and in isolated cells. Myocytes in various phases of mitosis (FIGS. 10 and 11) were identified and the mitotic index was calculated. Mitotic index was higher in old hearts compared to young hearts (FIG. 12). Thus, the senescent heart contains a pool of functionally-competent CPCs whose activation leads to intense myocyte regeneration.

B. Cardiac Stem Cells with Shortened Telomeres Give Rise to Senescent Myocytes

Figure 13:
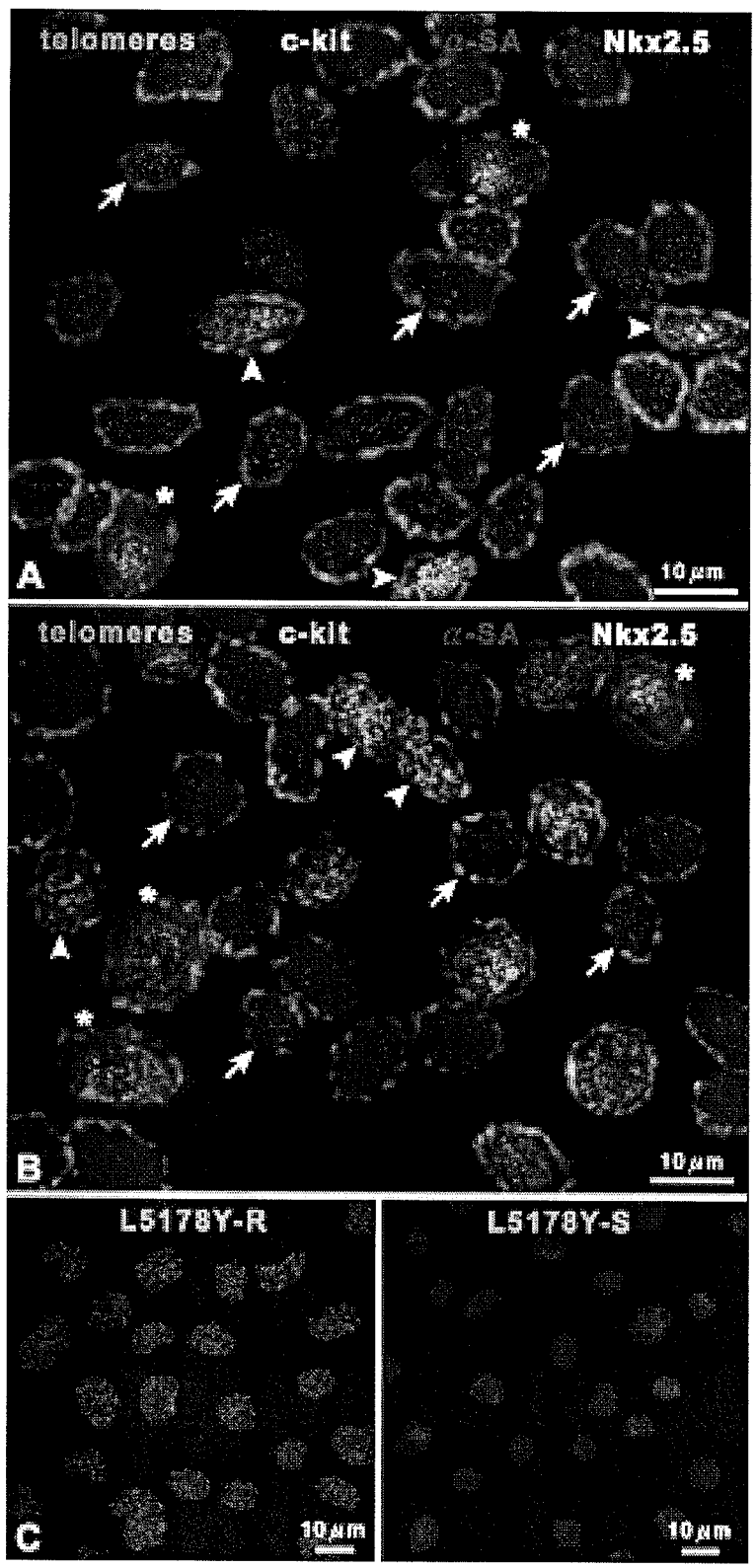
FIG. 13. Telomeres (Q-FISH, magenta) in cytospin preparations of freshly isolated CPCs from young (A) and old (B) hearts. Lin$^{neg}$-CPCs (c-kit, green; arrows), myocyte progenitors (Nkx2.5, white; arrowheads) and myocyte precursors (α-SA, red; asterisks) are present. (C) Lymphoma cells with long (L5178Y-R, 48 kbp) and short (L5178Y-S, 7 kbp) telomeres were used for comparison and reference point.
Figure 14:
FIG. 14. Young (A) and old (B) LV myocardium contains small cycling (Ki67, yellow; arrows) myocytes with long (A) and short (B) telomeres.

The increased myocyte regeneration in older hearts is at variance with the accumulation of p16$^{INK4a}$-positive-myocytes and the acquisition of the heart senescent phenotype with chronological age (Kajstura et al. (2000) Am. J. Pathol. 156: 813-819). Additionally, apoptosis of p16$^{INK4a}$-positive-myocytes is 6-fold higher in the old than young myocardium (Kajstura et al. (1996) Am. J. Physiol. 271: H1215-H1228) and myocyte progenitors-precursors and the myocyte mitotic index increase with age. These apparent contradictory results point to defects in the CPC compartment with aging. In the old heart, activation and differentiation of CPCs with relatively short telomeres may generate a myocyte progeny that rapidly reaches senescence. To test this hypothesis, telomere length was measured in cytospin preparations of c-kit-positive-cells collected from hearts at 3 and 27 months. Expanded (passage P7-P8) c-kit-positive-CPCs isolated from hearts from rats at 3 and 27 months of age were homogenized in CHAPS buffer and centrifuged at 4° C. Untreated and RNase-treated cell extracts were incubated with [γ-32P]ATP-end-labeled telomerase substrate (TS oligonucleotide: 5'-AATC-CGTCGA-GCAGAGTT-3', SEQ ID NO.: 1), Taq polymerase and anchored reverse primer (5'-GCGCGC-[CTAACC]3CTAACC-5', SEQ ID NO.: 2) for 45 min. Samples were exposed to 28 amplification cycles (Leri et al. (2001) Proc. Natl. Acad. Sci. USA 98: 8626-8631; Torella et al. (2004) Circ. Res. 94: 514-524; Urbanek et al. (2005) Proc. Natl. Acad. Sci. USA 102: 8692-8697). PCR products were separated on 12% polyacrylamide gels. Telomerase-induced reactions generated a ladder with a 6-bp periodicity. The optical density (OD) of the bands was normalized for PCR efficiency. Telomere length was evaluated in cytospins of freshly isolated c-kit-positive-cells from hearts at 3 and 27 months by quantitative fluorescence in situ hybridization (Q-FISH) and confocal microscopy (Chimenti et al. (2003) Cir. Res. 93: 604-613; Leri et al. (2003) EMBO J. 22: 131-139; Urbanek et al. (2005) Proc. Natl. Acad. Sci. USA 102: 8692-8697). Representative micrographs are shown in FIGS. 13A and B. Similarly, telomere length was evaluated in small developing myocytes in tissue sections of young and old hearts (FIGS. 14A and B). A fluorescein isothiocyanate-peptide nucleic acid (FITC-PNA) probe was used. The fluorescent signals measured in lymphoma cells with short (L5178Y-S, 7 kbp) and long (L5178Y-R, 48 kbp) telomeres (FIG. 13C) were used as a reference point (Leri et al. (2003) EMBO J. 22: 131-139; Chimenti et al. (2003) Cir. Res. 93: 604-613; Urbanek et al. (2005) Proc. Natl. Acad. Sci. USA 102: 8692-8697).

Figure 15:
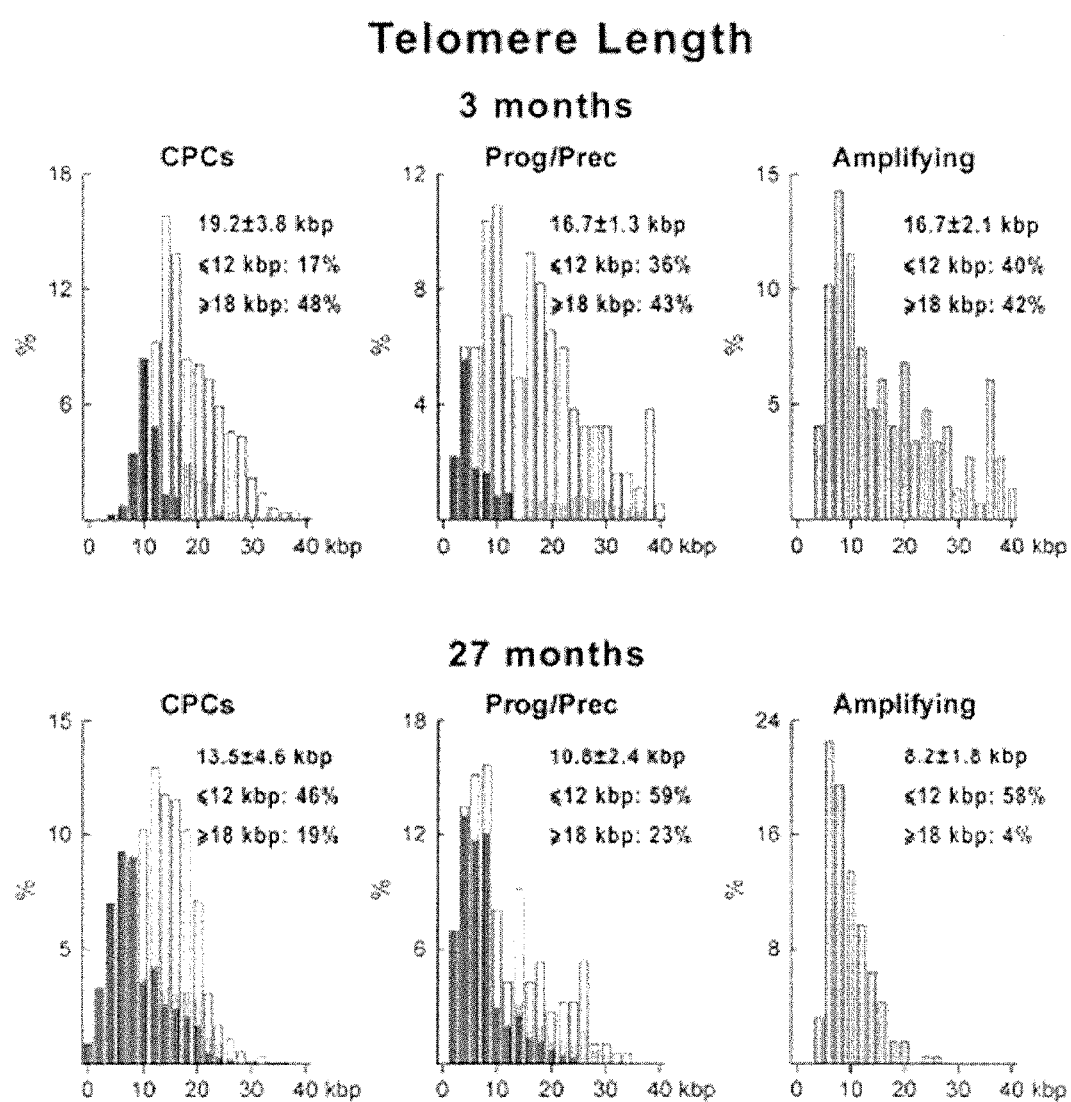
FIG. 15. Distribution of telomeric length in Lin$^{neg}$-CPCs, myocyte progenitors-precursors and amplifying myocytes in young (upper panels) and old (lower panels) hearts. In each cell class, average telomere length is listed together with the percentage of cells with telomeres ≦than 12 kbp and ≧than 18 kbp. For each cell category, the fraction of cycling cells (green solid bars) and senescent p16$^{INK4a}$-positive-cells (red solid bars) are shown.
Figure 16:
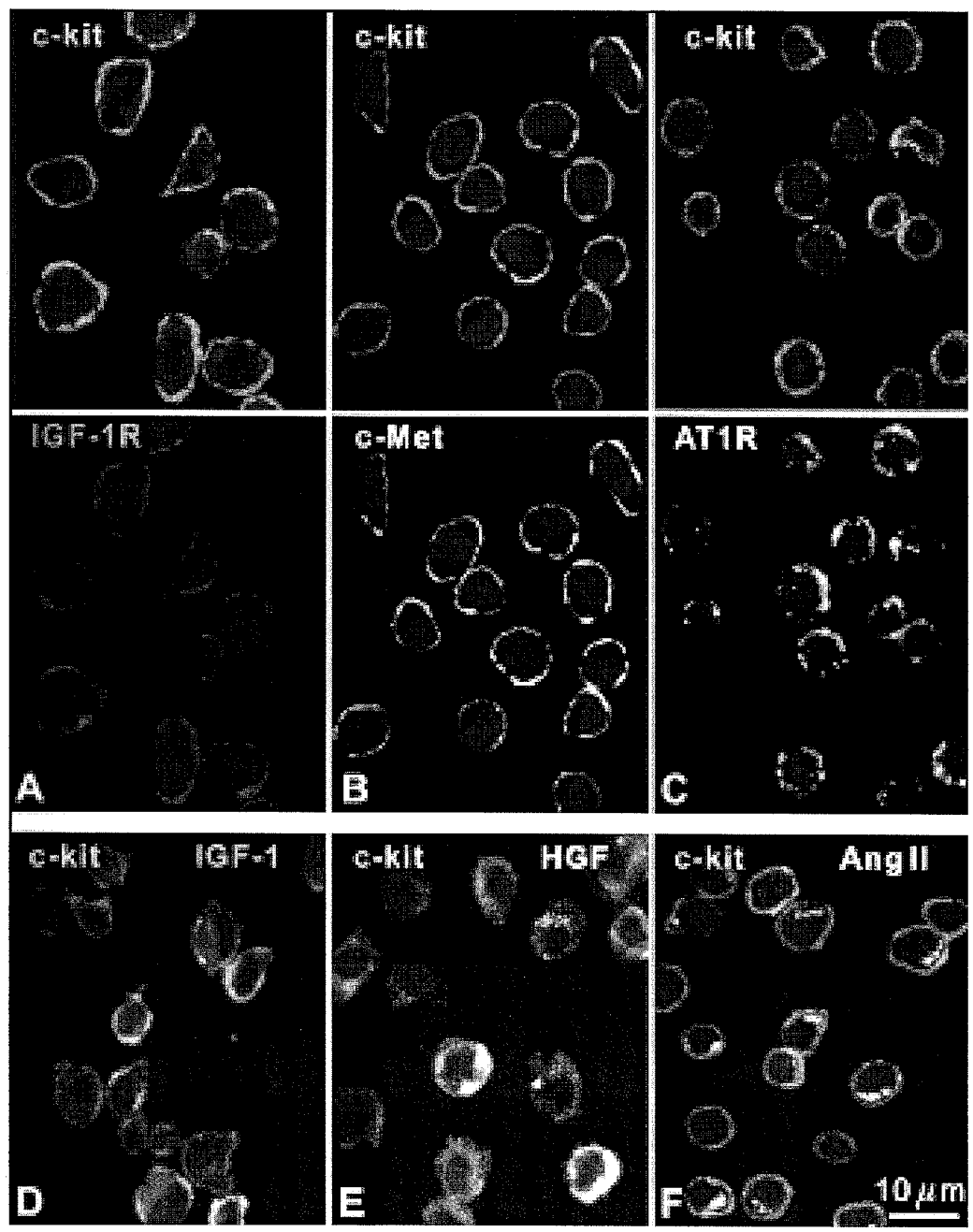
FIG. 16. Freshly isolated CPCs from young (A, B, D, E) and old (C, F) hearts express IGF-1R (A, magenta), c-Met (B, yellow) and AT1 receptors (C, white) on the membrane and IGF-1 (D, magenta), HGF (E, yellow) and Ang II (F, white) in the cytoplasm.

In old hearts, the distribution of telomere length in CPCs, myocyte progenitors-precursors and developing myocytes was shifted to the left towards shorter telomeres (FIG. 15). Average telomere length in CPCs, myocyte progenitors-precursors and developing myocytes was 30%, 35% and 51% shorter in old than young cells, respectively. Nearly 50% of old CPCs and ~15% of young CPCs had telomeres less than 12 kbp and were p16$^{INK4a}$-positive. However, ~20% of the old CPC pool had telomeres greater than 18 kbp pointing to a relevant growth reserve of the senescent myocardium. Thus, telomere attrition in CPCs with age leads to the generation of a myocyte progeny that rapidly acquires the senescent phenotype conditioning organ aging.

Example 2

The Balance of Growth Factor Receptor Systems is Shifted in Stem Cells of the Aging Heart A. Expression of IGF-1/IGF-1R, HGF/c-MET, and Ang II/AT1 R in Stem Cells from the Aging Heart The IGF-1/IGF-1R system preserves telomere length through attenuation of oxidative stress and phosphorylation of telomerase. Moreover, this system promotes CPC growth and survival via the Akt-PI3 kinase pathway (Torella et al. (2004) Circ. Res. 94: 514-524; Gude et al. (2006) Circ. Res. 99: 381-388). However, IGF/1-IGF-1R has no role in CPC migration and homing which are predominantly modulated by the HGF/c-Met receptor system (Linke et al. (2005) Proc. Natl. Acad. Sci. USA 102: 8966-8971; Urbanek et al. (2005) Circ. Res. 97: 663-673). The impact of IGF-1 on primitive cells is not restricted to the heart. IGF-1 induces proliferation and differentiation of satellite cells in skeletal muscle (Musaro et al. (2004) Proc. Natl. Acad. Sci. USA 101: 1206-1210) and prevents skeletal muscle atrophy with heart failure (Schulze et al. (2005) Circ. Res. 97: 418-426). Although the consequences of angiotensin II (Ang II) on CPCs are unknown, this growth factor induces senescence and decreases the number and function (Kobayashi et al. (2006) Hypertens. Res. 29: 449-455) of endothelial progenitor cells, triggers apoptosis (Leri et al. (1998) J. Clin. Invest. 101: 1326-1342) and is implicated in the progression of heart failure (McMurray et al. (2003) Lancet 362: 767-771). Therefore, we determined whether CPCs possess a local renin-angiotensin system (RAS) and whether aging affects RAS and the expression of IGF-1, IGF-1R, HGF and c-Met in CPCs.

The expression of these growth factors and their corresponding receptors in CPCs was assessed by similar methods as those described in Example 1. CPCs express IGF-1R, c-Met and AT1-receptors together with IGF-1, HGF and Ang II (FIG. 16A-F). The detection of Ang II, IGF-1 and HGF in freshly isolated CPCs and in tissue sections cannot discriminate whether the growth factors are formed within the cells or sequestered from the circulation. Therefore, transcripts for these growth factors and their corresponding receptors were detected by real-time RT-PCR in CPCs. Total RNA was extracted from c-kit-positive-CPCs obtained from hearts at 3, 12, 16 and 24 months with a commercial RNA isolation kit using Trizol (TRI REAGENT, Sigma) as described previously in detail (Ojaimi et al. (2005) Am J. Physiol. 289: H1399-H1407). cDNA was obtained from 500 ng total RNA in a 20 µl reaction containing first strand buffer, 0.4 mM each of dTTP, dATP, dGTP and dCTP together with 200U of Superscript III (Invitrogen), 10U of RNase inhibitor (RNasin Plus, Promega) and 500 ng of random hexamer (Promega). This mixture was incubated at 42° C. for 2 hours. Subsequently, real-time RT-PCR was performed with primers (see Table 2) designed using the Primer Express v2.0 analysis software (Applied Biosystems). The LightCycler PCR system (Roche Diagnostics) was employed for real-time RT-PCR that was done in duplicates. In each case, 5 ng cDNA were used with the exception of renin that required 15 ng. cDNA was combined with SYBR Green master mix (Light-Cycler Fast Start DNA Master SYBR Green I, Roche) and cycling conditions were as follows: 95° C. for 10 min followed by 45 cycles of amplification (95° C. denaturation for 10 sec, annealing for 5 sec and 72° C. extension for 20 sec). The annealing temperature used for each primer set is listed in Table 2 below. Quantified values were normalized against the input determined by the housekeeping gene β-actin.

TABLE 2

Primers and annealing temperatures used in the real-time RT-PCR

| Gene | Forward primer (5'→3') | Reverse primer (5'→3') | Annealing T (° C.) |
|---|---|---|---|
| IGF-1 (Igf1) | CGAACCTCCAATAAAGATACAC SEQ ID NO.: 3 | CAACACTCATCCACAATGCC SEQ ID NO.: 4 | 61 |
| IGF-1R (Igf1r) | CGAGCAAGTTCTTCGTTTCGT SEQ ID NO.: 5 | TGTACTGCCAGCACATGCG SEQ ID NO.: 6 | 61 |
| HGF (Hgf) | TGCCCTATTTCCCGTTGTG SEQ ID NO.: 7 | AATGCCATTTACAACTCGCAGTT SEQ ID NO.: 8 | 61 |
| c-Met (Met) | ACAACAAAACGGGTGCGAAA SEQ ID NO.: 9 | TCATGAGCTCCCAGAGAAGCA SEQ ID NO.: 10 | 61 |
| Renin (Ren1) | CCTGGGAGTCAAAGAGAAGAG SEQ ID NO.: 11 | GTATAGAACTTGCGGATGAAGG SEQ ID NO.: 12 | 62 |
| Aogen (Agt) | ATCAACAGGTTTGTGCAGGC SEQ ID NO.: 13 | GTTGTCCACCCAGAACTCATGG SEQ ID NO.: 14 | 66 |
| AT1 receptor (Agtr1) | GTCCTCTCAGCTCTGCCACATT SEQ ID NO.: 15 | CACTTGACCTTTACCTGGTGATCA SEQ ID NO.: 16 | 64 |
| B-actin (Actb) | ACCCTGTGCTGCTCACCGAG SEQ ID NO.: 17 | CCAGTGGTACGACCAGAGGC SEQ ID NO.: 18 | Same as target gene |

Figure 17:
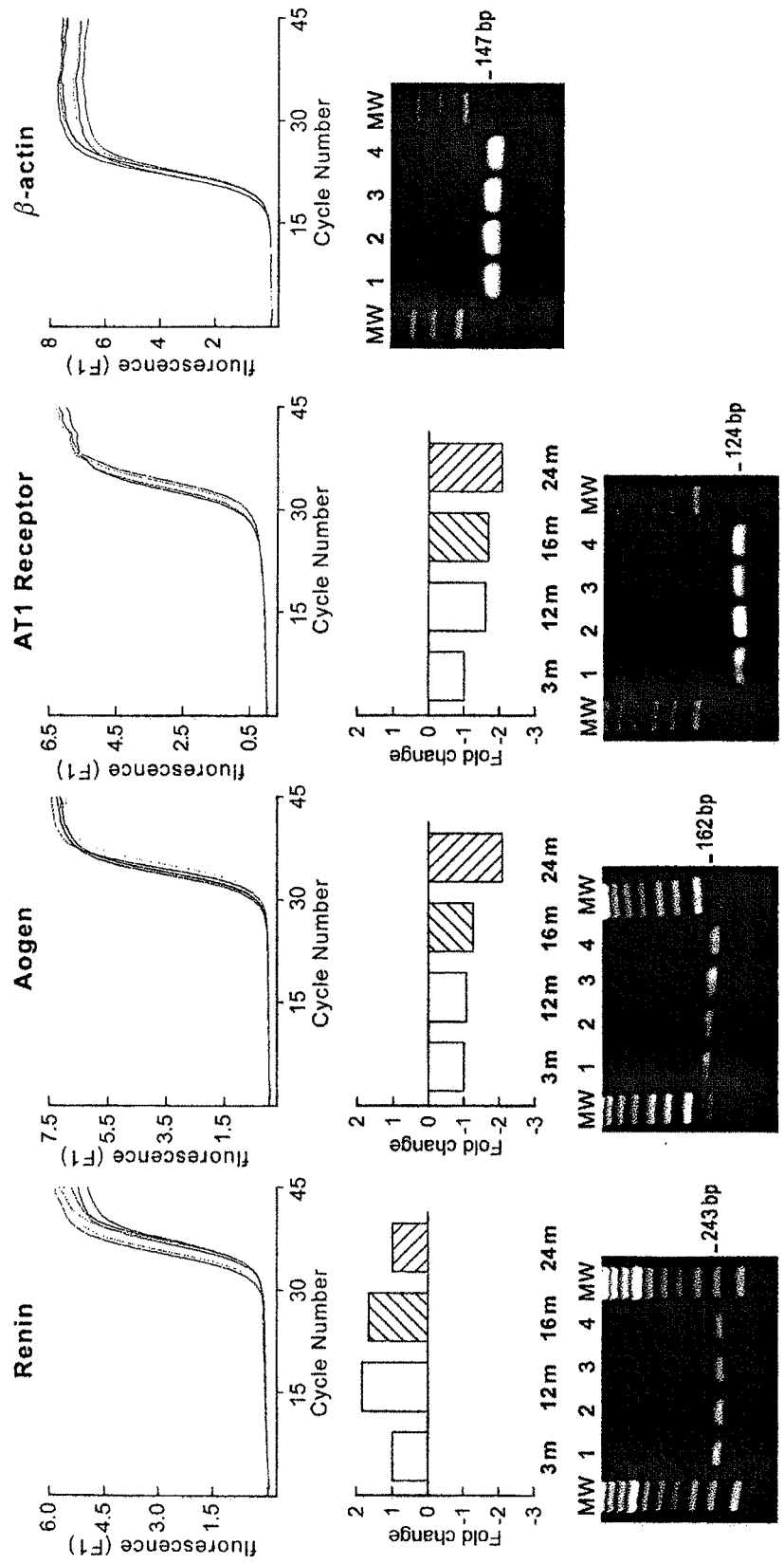
FIG. 17. Renin, Aogen and AT1 receptor mRNAs in CPCs as a function of age. β-actin was employed for normalization. RT-PCR products had the expected molecular weights and sequences. Fold-changes in mRNAs are shown with respect to values in young CPCs at 3 months.
Figure 18:
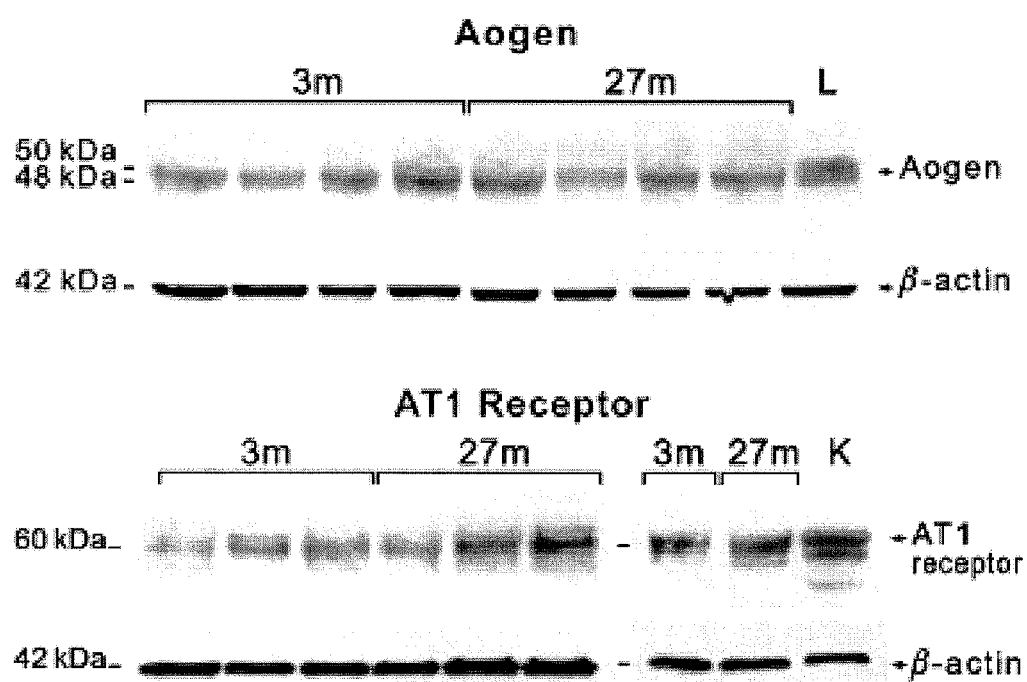
FIG. 18. Protein levels of Aogen and AT1 receptors in young (3 months) and old (27 months) CPCs. Lung (L) and kidney (K) tissue lysates were employed as positive controls.

CPC aging resulted in a consistent downregulation of angiotensinogen (Aogen) and AT1 receptors while renin mRNA increased at 12 and 16 months returning to baseline at 24 months (FIG. 17). Although changes in mRNAs occurred with age, the protein levels (assessed by standard Western blotting techniques) of Aogen and AT1 receptors did not vary (FIG. 18) suggesting that RAS function remained intact in old CPCs.

Figure 19:
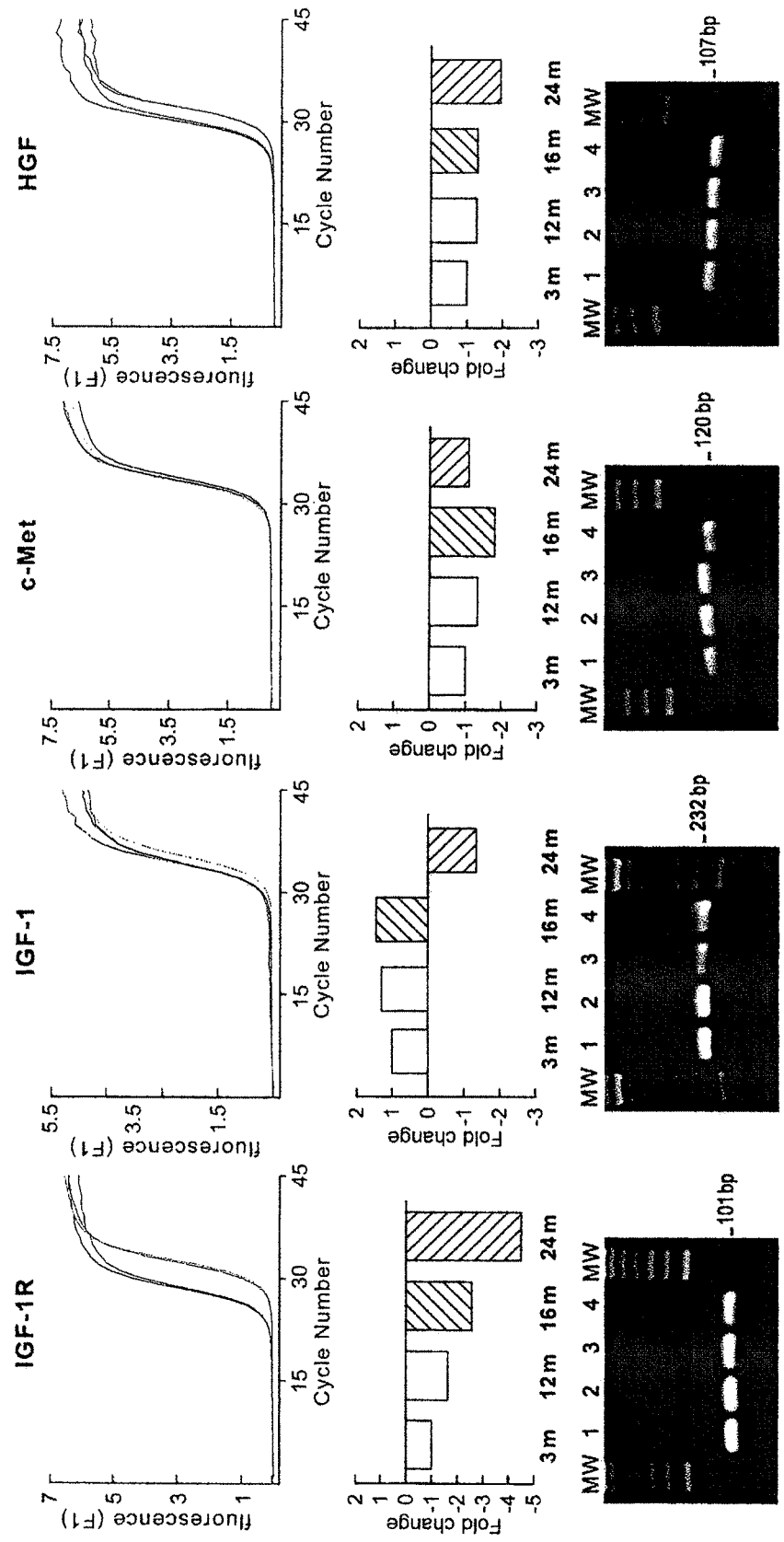
FIG. 19. IGF-1R, IGF-1, c-Met and HGF mRNAs in CPCs as a function of age. β-actin was employed for normalization. RT-PCR products had the expected molecular weights and sequences. Fold-changes in mRNAs are shown with respect to values in young CPCs at 3 months.

The CPC IGF-1/IGF-1R system was characterized by a significant decrease in IGF-1R mRNA with aging while IGF-1 expression was variable and tended to be reduced only at 24 months. c-Met transcripts were modestly affected in aging CPCs but HGF mRNA was attenuated at 24 months (FIG. 19).

To characterize further the effects of age on primitive cells, the ability of CPCs at 3 and 27 months to synthesize and secrete IGF-1, HGF and Ang II was measured. Expanded c-kit-positive-CPCs from hearts at 3 and 27 months (P5-P6) were cultured in SFM and exposed to IGF-1 (150 ng/mL), HGF (200 ng/mL) or Ang II (10-11M) for a period of 24 hours. Media containing growth factors were removed and cells were washed twice and fresh SFM was added. The SFM contained antibodies against IGF-1R (Abcam) and c-Met (R&D Systems) or the AT1 receptor antagonist telmisartan (10- 7M; Sigma) and the AT2 receptor blocker PD123319 (10-7M, Sigma). The blockers were employed to avoid ligand binding. Media were collected after 3 and 9 hours for IGF-1, HGF and Ang II. Growth factor quantities were determined by ELISA (IGF-1, R&D Systems; HGF, B-Bridge International; Ang II, Peninsula Laboratories) and normalized by the total quantity of CPC proteins and β-actin (Sigma) expression measured by Western blotting.

Figure 20:
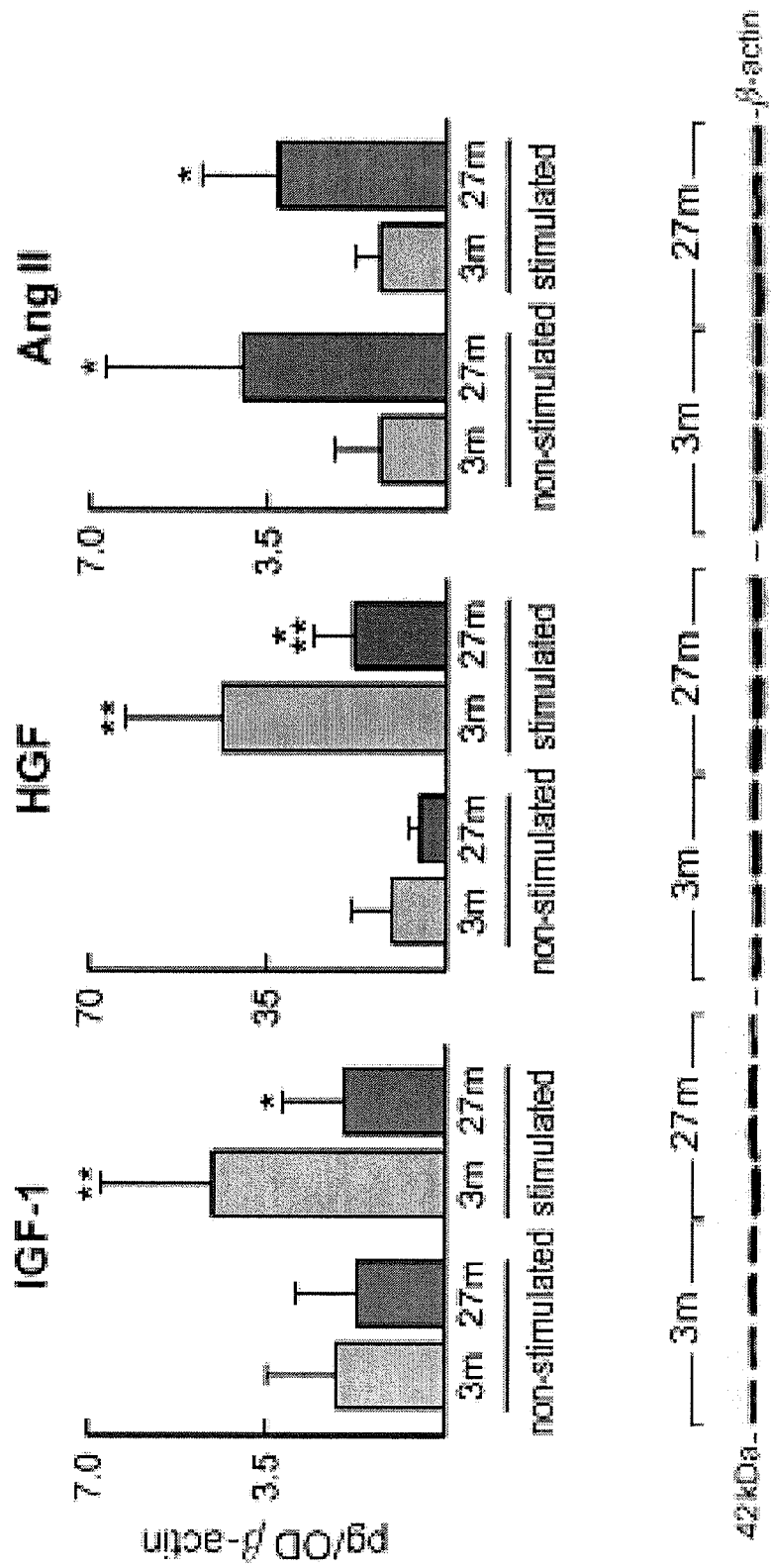
FIG. 20. Formation of IGF-1, HGF and Ang II in non-stimulated and ligand-stimulated CPCs for 24 hours. Values were normalized by total amount of CPC protein and β-actin expression. *p<0.05 versus 3 months (3 m); **p<0.05 versus non-stimulated CPCs.

Baseline values for IGF-1 were similar in young and old CPCs but HGF tended to be lower in old cells. Ang II levels, however, were 3-fold higher in old than in young CPCs (FIG. 20). Following stimulation with the ligands, the formation of IGF-1 was 8-fold higher in cells at 3 months than at 27 months while the synthesis of HGF increased 4-fold in young and 3.5-fold in old CPCs. Ang II stimulation of CPCs did not increase the rate of secretion of the octapeptide in either cell population. Thus, aging negatively affects regulatory systems involved in CPC growth, survival and migration potentiating the consequences of the local RAS on the cells. These phenotypic properties may have a critical role in CPC senescence and myocardial aging.

B. Effects of IGF-1, HGF, and Ang II on Cardiac Stem Cells Isolated from Young and Old Hearts To determine the functional consequences of the changes in expression of IGF-1/IGF-1R, HGF/c-Met and RAS on CPCs, c-kit-positive-CPCs from hearts at 3 and 27 months at P7-P8 were cultured in SFM and stimulated with IGF-1 (150 ng/mL), HGF (200 ng/mL), IGF-1 and HGF together (IGF-1-HGF) or Ang II ($10^{-9}$M) for 24 hours. BrdU was added to the medium at 8 hour intervals. Cells were fixed and BrdU incorporation was measured as previously described (Beltrami et al. (2003) Cell 114: 763-776; Linke et al. (2005) Proc. Natl. Acad. Sci. USA 102: 8966-8971; Urbanek et al. (2005) Circ. Res. 97: 663-673). In a similar manner, CPCs were stimulated with Ang II ($10^{-9}$M) alone or in the presence of IGF-1 (150 ng/mL), HGF (200 ng/mL) and IGF-1-HGF for 24 hours. Cells were fixed and apoptosis was determined by the TdT assay (Kajstura et al. (1996) Am. J. Physiol. 271: H1215-H1228; Rota et al. (2006) Circ. Res. 99: 42-52). The effect of Ang II ($10^{-9}$M) for 24 hours on the extent of oxidative stress in CPCs was measured by the presence of 8-OH-dG (Rota et al. (2006) Circ. Res. 99: 42-52). The intensity of the 8-OH-dG signal was measured with an ImagePro software (Kajstura et al. (2001) Diabetes 50: 1414-1424; Torella et al. (2004) Circ. Res. 94: 514-524) and normalized for the PI fluorescence.

The ability of IGF-1, HGF and IGF-1-HGF to induce CPC proliferation was attenuated but not abolished in old CPCs. Ang II had no growth promoting effects on young and old CPCs (FIG. 21A). Ang II stimulated apoptosis in young and old CPCs, and IGF-1 decreased the extent of Ang II-mediated CPC death. Conversely, HGF alone did not decrease apoptosis or enhance the effects of IGF-1 on CPC survival (FIG. 21B). Although the inhibitory role of IGF-1 in CPC apoptosis was higher in young than in old cells, a 40% reduction in apoptosis was measured in old CPCs.

Ang II leads to the generation of hydroxyl radical which in turn promotes deoxyguanosine (dG) oxidation, a phenomenon that may vary in young and old CPCs. In the presence of hydroxyl radical, the formation of 8-OH-dG lesions is 5-fold higher in telomeric than in non-telomeric DNA (Kawanishi and Oikawa (2004) Ann. NY Acad. Sci. 1019: 278-284). Oxidative stress induces telomeric shortening, growth arrest and apoptosis. 8-OH-dG was detected in a larger fraction of old than young CPCs (FIG. 21C-E) and Ang II further increased the population of 8-OH-dG-positive cells in old CPCs, providing a mechanism for Ang II-mediated DNA damage with age. Thus, the old heart contains a pool of functionally-competent CPCs which, however, are more sensitive to oxidative stress and its impact on DNA integrity.

Figure 22:
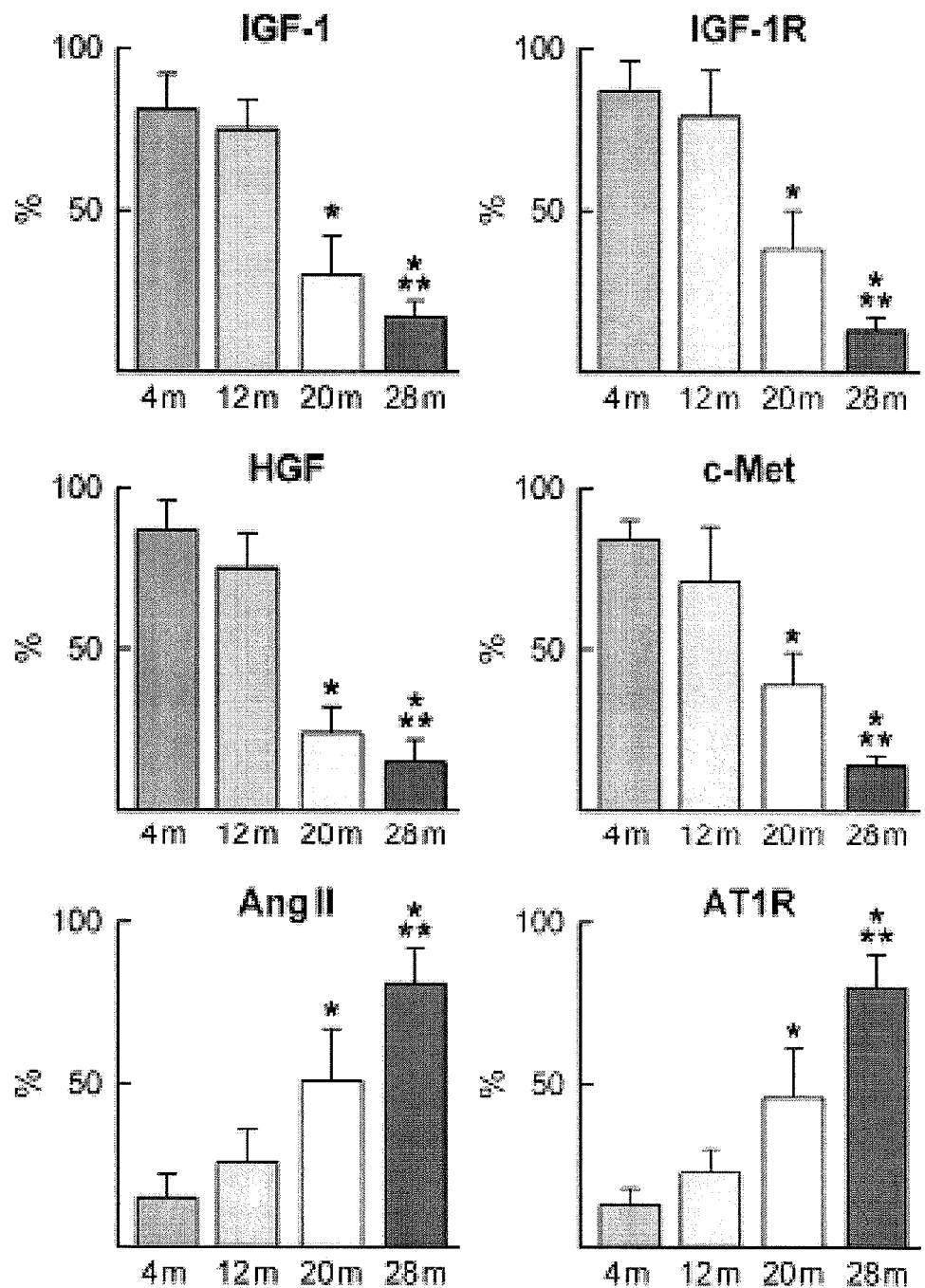
FIG. 22. CPCs positive for IGF-1, IGF-1R, HGF, c-Met, Ang 11 and AT1 receptors. *p<0.05 versus 4 m and 12 m; **p<0.05 versus 20 m.

Based on these results, we established whether these growth-factor receptor systems were uniformly affected in all CPCs as a function of age or aging progressively involved a larger number of CPCs leaving intact a subset of progenitor cells. The fraction of CPCs positive for IGF-1, IGF-1R, HGF and c-Met decreased from 3 to 28 months and the percentage of CPCs expressing Ang 11 and AT1 receptors increased (FIG. 22). CPCs expressing IGF-1/IGF-1R and HGF/c-Met were consistently negative for $p16^{INK4a}$ while $p16^{INK4a}$ was detected in CPCs positive for Ang 11 and AT1 receptors (not shown).

Figure 23:
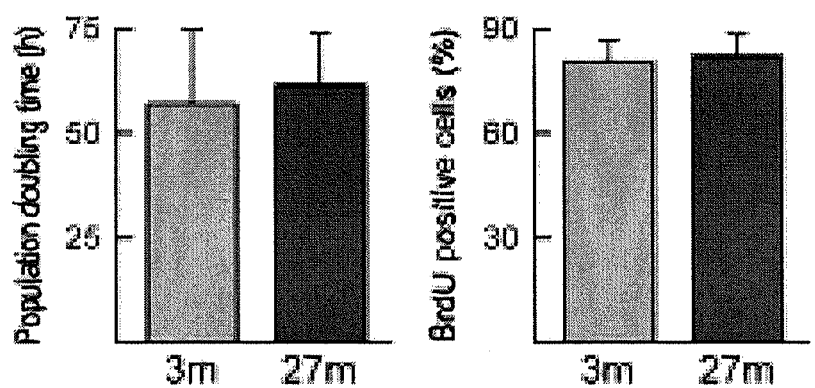
FIG. 23. Population doubling time and BrdU labeling of CPCs from young (3 m) and old (27 m) hearts.
Figure 24:
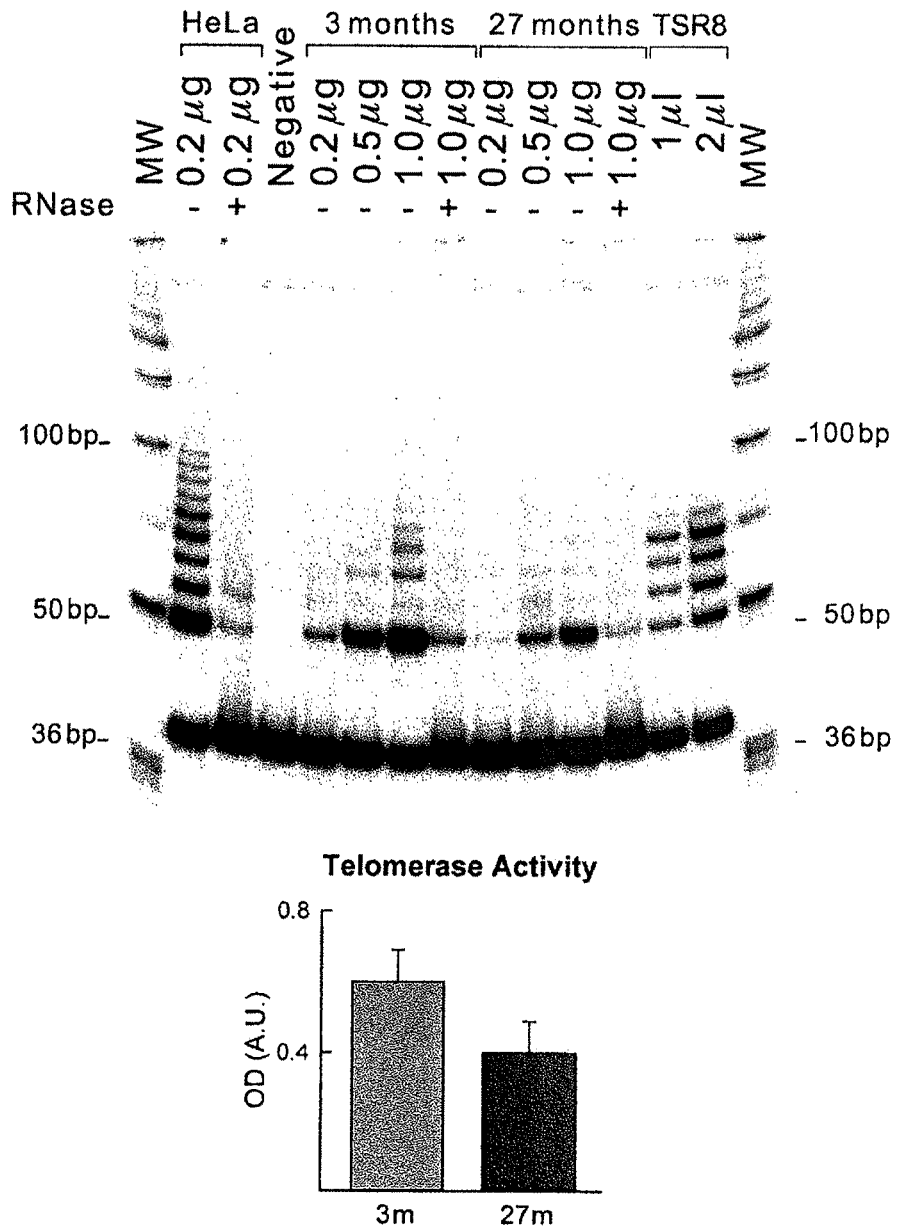
FIG. 24. Telomerase activity in young (3 m) and old (27 m) CPCs measured by TRAP assay. Telomerase activity starts at 50 bp and displays 6 bp periodicity. HeLa cells were used as positive control and samples treated with RNase as negative control. TSR8 was employed to confirm the position of the bands. Three protein concentrations were used to validate the specificity of the assay. The band at 36 bp is an internal control for PCR efficiency.

To test whether a small proportion of CPCs in the old heart possessed a growth potential similar to that in the young myocardium, CPCs at 3 and 27 months were serially passaged to reach 20 population doublings. Although the lag growth phase was longer in CPCs at 27 months, the exponential growth phase was similar in both groups of cells (FIG. 23). Similarly, BrdU-labeling for 5 days at P7-P8 resulted in comparable levels of BrdU-positive-CPCs at both ages. Importantly, telomerase activity at P7-P8 was decreased only by 33% in old CPCs (FIG. 24). Thus, myocardial aging does not deplete the pool of functionally-competent CPCs.

Example 3

Mobilization of Resident Cardiac Stem Cells by HGF in Young and Aged Hearts

Figure 25:
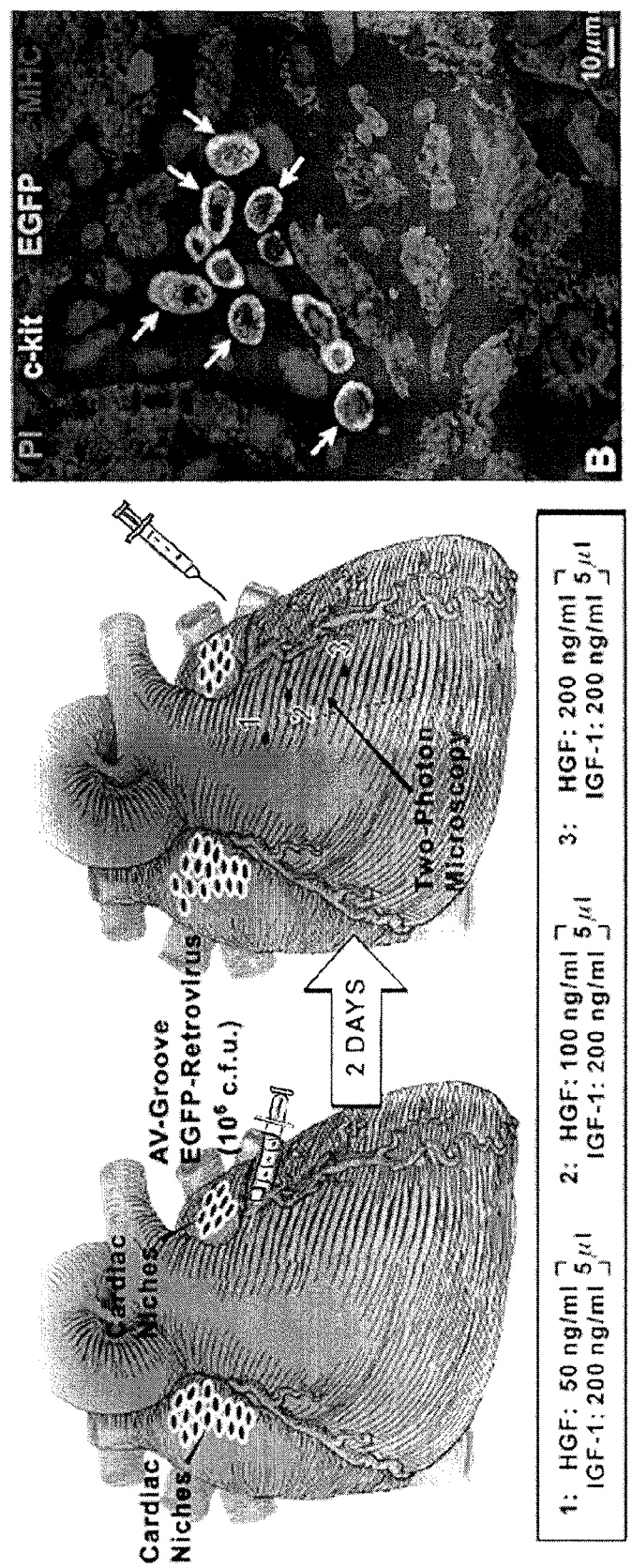
FIG. 25. (A) Schematically, clusters of CPCs are stored in the atria. This anatomical area was injected with EGFP-retrovirus to infect cycling CPCs. Two days after infection, increasing concentrations of HGF alone or together with IGF-1 were delivered intramyocardially from the atria to the LV mid-region to create a chemotactic gradient promoting the migration of CPCs-ECCs. (B) Section of atrial myocardium containing several CPCs (c-kit, white) some of which were infected by the EGFP-retrovirus (green; arrows). Myocytes (MHC, red).
Figure 26:
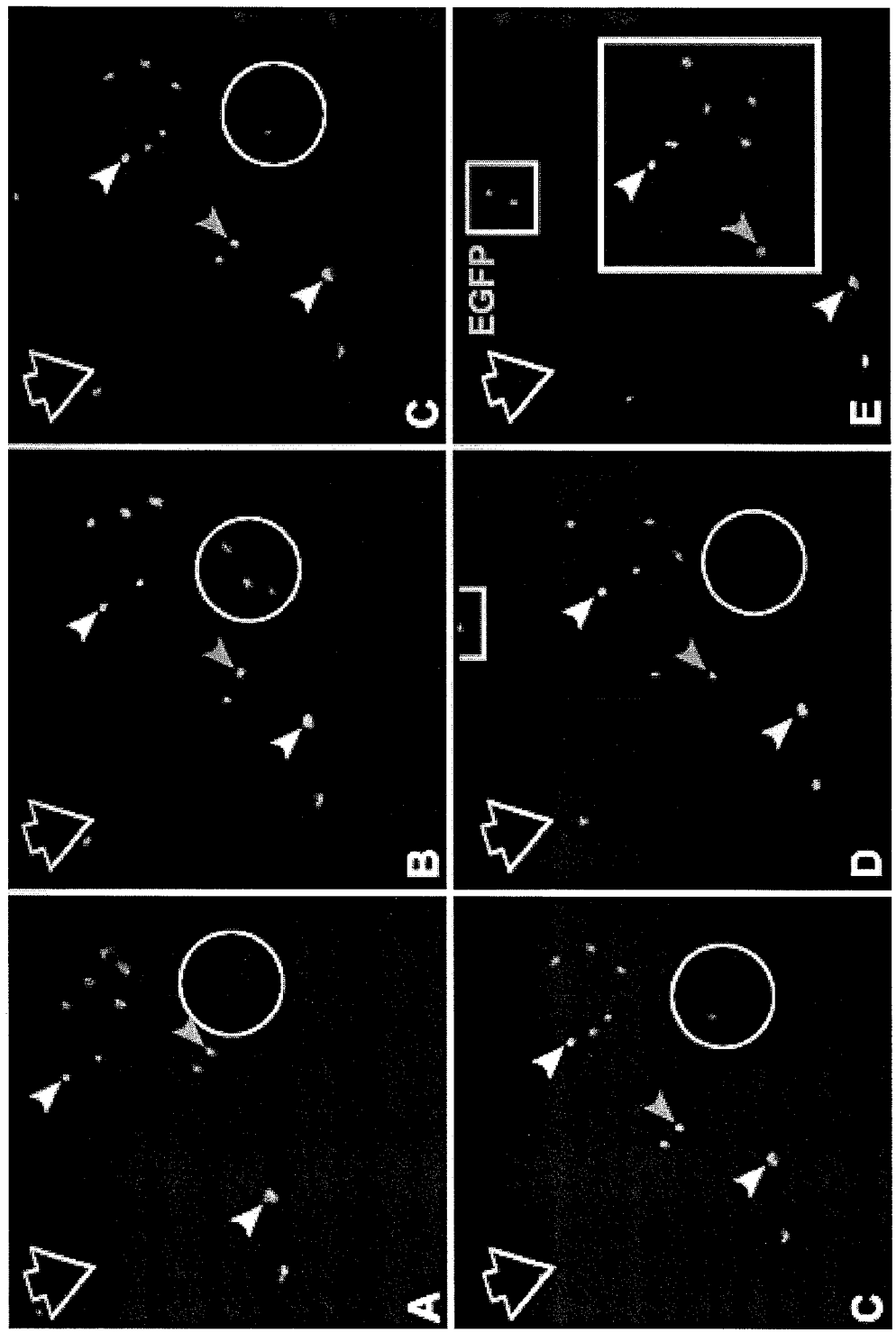
FIG. 26. Two days after the injection of the retrovirus, growth factors were administrated and the migration of EGFP-positive-cells was examined ex vivo in an oxygenated Tyrode solution preparation by two-photon microscopy. These images correspond to cell locomotion 10 hours after the administration of growth factors in a Fischer 344 rat at 4 months of age. These five panels (A-E), panel C is shown twice, illustrate the same field examined at intervals of 20 minutes each. Green fluorescence reflects EGFP-labeled-cells in vivo. Arrowheads of various colors point to cells moving in the direction of the large open arrows over a period of 80 minutes. The white circle shows cells that appeared in the field and then disappeared. The white small square in panel E shows two cells that began to appear in panel D.

A. Mobilized Cardiac Stem Cells have Long Telomeres and are $p16^{INK4A}$-Negative The presence of a compartment of non-senescent-CPCs in the aged heart raised the possibility that these cells may be activated and induced to translocate from their sites of storage in the atria and apex to the LV base-mid-region. A retroviral vector encoding EGFP was injected in the atrioventricular groove to label replicating cells in animals at 4 and 27 months (FIG. 25). In both cases, ~9-12% c-kit-positive-CPCs were infected with EGFP at the site of injection. This value was consistent with the fraction of Ki67-positive-CPCs in this region (data not shown). Two days after infection, hearts were excised and three increasing concentrations of HGF were administered from the site of CPC accumulation in proximity of the atrioventricular groove to the LV mid-region (FIG. 25). As previously done, this chemotactic gradient was introduced to favor the translocation of CPCs to the portion of the heart that sustains most of cardiac function (Linke et al. (2005) Proc. Natl. Acad. Sci. USA 102: 8966-8971; Urbanek et al. (2005) Circ. Res. 97: 663-673). Also, myocardial damage is predominantly located in this anatomical area (Kajstura et al. (1996) Am. J. Physiol. 271: H1215-H1228). Each heart was mounted on the stage of a two-photon microscope (Bio-Rad Radiance 2100 MP) and was continuously perfused retrogradely through the aorta and superfused at 37° C. with an oxygenated Tyrode solution in the absence or presence of rhodamine-labeled dextran. Dextran has a molecular weight of 70,000 and because of this size, dextran does not cross the endothelial barrier and remains confined to the coronary vasculature (Dawn et al. (2005) Proc. Natl. Acad. Sci. USA 102: 3766-3771; Urbanek et al. (2005) Circ. Res. 97: 663-673). EGFP and rhodamine were excited, respectively, at 960 and 840 nm with a mode-locked Ti:Sapphire femtosecond laser (Tsunami, Spectra-Physics). The corresponding images were acquired at emission wavelengths of 515 and 600 nm. By this approach, the translocation of EGFP-positive-cells and their localization with respect to the coronary vasculature was determined over time (Urbanek et al. (2005) Circ. Res. 97: 663-673). Images were collected up to 6 hours after HGF injection (FIGS. 26-29). Subsequently, hearts were fixed and analyzed by confocal microscopy.

Figure 27:
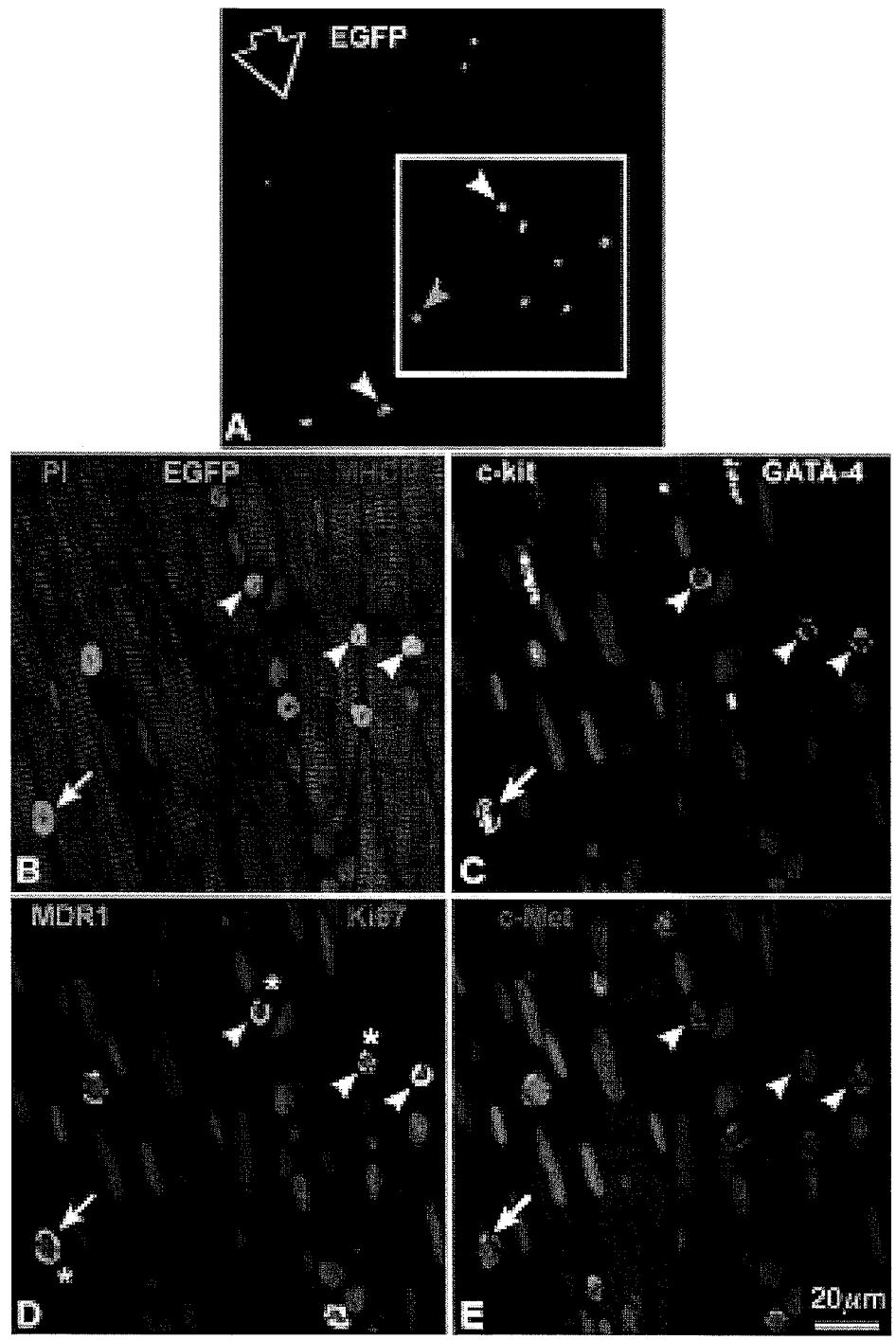
FIG. 27. Panel E from FIG. 26 is illustrated again here (A). The square defines the EGFP positive cells detected in the living tissue by two-photon microscopy and after fixation and staining of the same LV region by confocal microscopy (panel B). Green fluorescence in both panels identifies the same cells (A and B). EGFP-positive-cells express c-kit (C, green), MDR1 (D, yellow), GATA-4 (C, white) and c-Met (E, red). For example, 3 EGFP-positive-cells are Ki67-positive (D, magenta; asterisks) and express c-kit, MDR1 and c-Met (arrowheads) and 1 EGFP-positive-cell expresses all four proteins (arrow). Myocytes (MHC, red). Nuclei (PI, blue).
Figure 28:
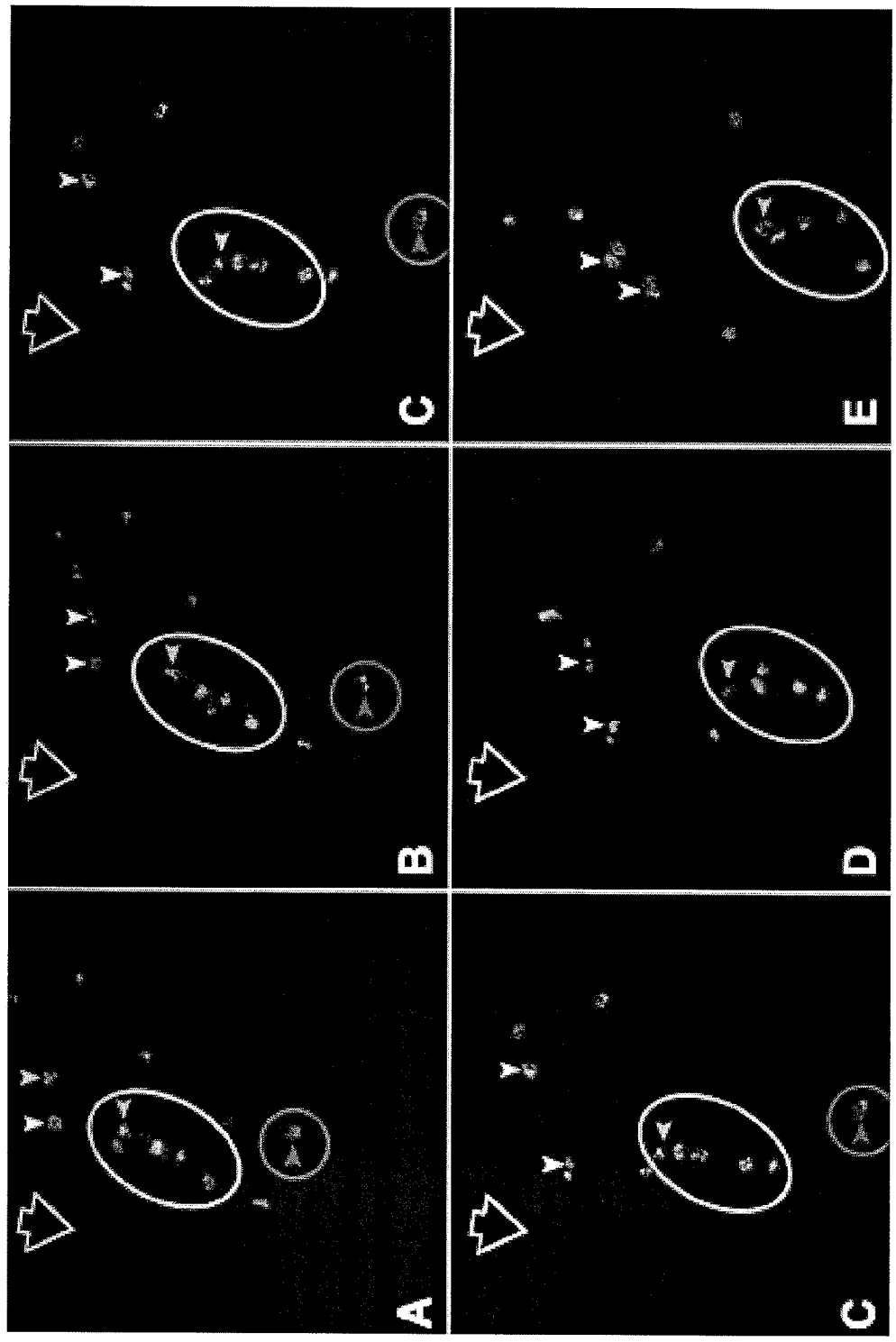
FIG. 28. These images correspond to cell locomotion 10 hours after the administration of growth factors in a Fischer 344 rat at 27 months of age. These five panels (A-E), panel C is shown twice, illustrate the same field examined at intervals of 15 minutes each. Green fluorescence reflects EGFP-labeled-cells in vivo. Arrowheads of various colors point to cells moving in the direction of the large open arrows over a period of 60 minutes. The red circle shows a cell that was in the field and then disappeared. The yellow oval surrounds cells that moved within the field throughout the period of observation.
Figure 29:
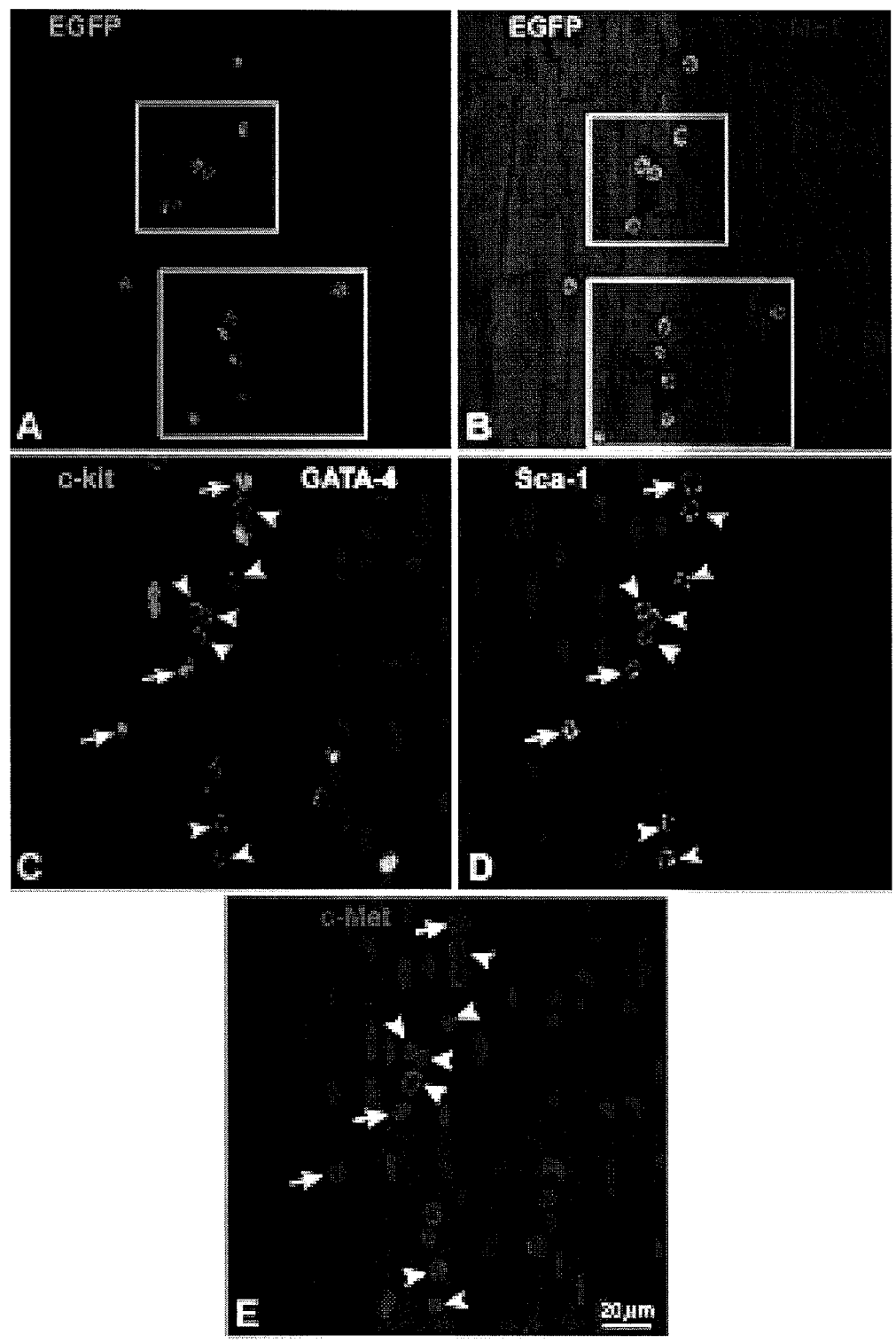
FIG. 29. Panel E from FIG. 28 is illustrated again here at higher magnification; new panel A. Squares and rectangles define the EGFP positive cells detected in the living tissue by two-photon microscopy and after fixation and staining of the same LV region by confocal microscopy (panel B). Green fluorescence in both panels identifies the same cells (A and B). EGFP-positive-cells express c-kit (C, green), Sca-1 (D, yellow), GATA-4 (C, white) and c-Met (E, red). For example, 7 EGFP-positive-cells express c-kit, Sca-1 and c-Met (arrowheads) and 3 EGFP-positive-cell express all four proteins (arrows). Myocytes (MHC, red). Nuclei (PI, blue).

At completion, the area of myocardium examined by two-photon microscopy was processed and analyzed for the identity of the migrated EGFP-positive-cells. Translocated EGFP-positive-cells expressed c-kit or the other stem cell antigens MDR1 and Sca-1 together with c-Met. Moreover, GATA-4 was detected in some of the migrated EGFP-positive-c-kit-positive-cells documenting their commitment to the myocyte lineage. Ki67 was present in a subset of these cells (FIGS. 27 and 29).

Figure 30:
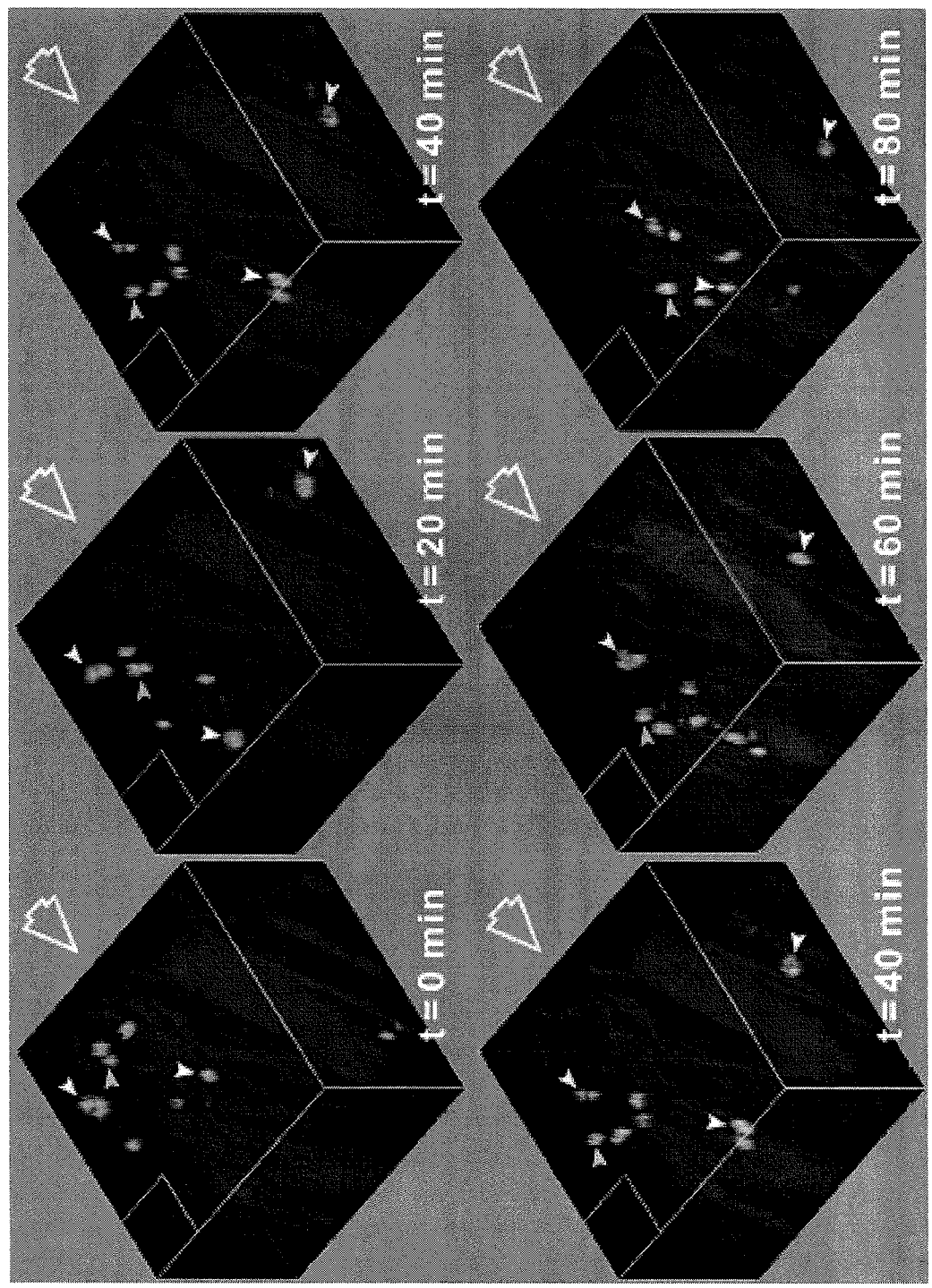
FIG. 30. Rat heart at 27 months. Colored arrowheads point to EGFP-positive-cells (green) moving in the direction of the yellow open-arrows. The coronary vasculature is visualized by rhodamine-labeled-dextran (red).
Figure 31:
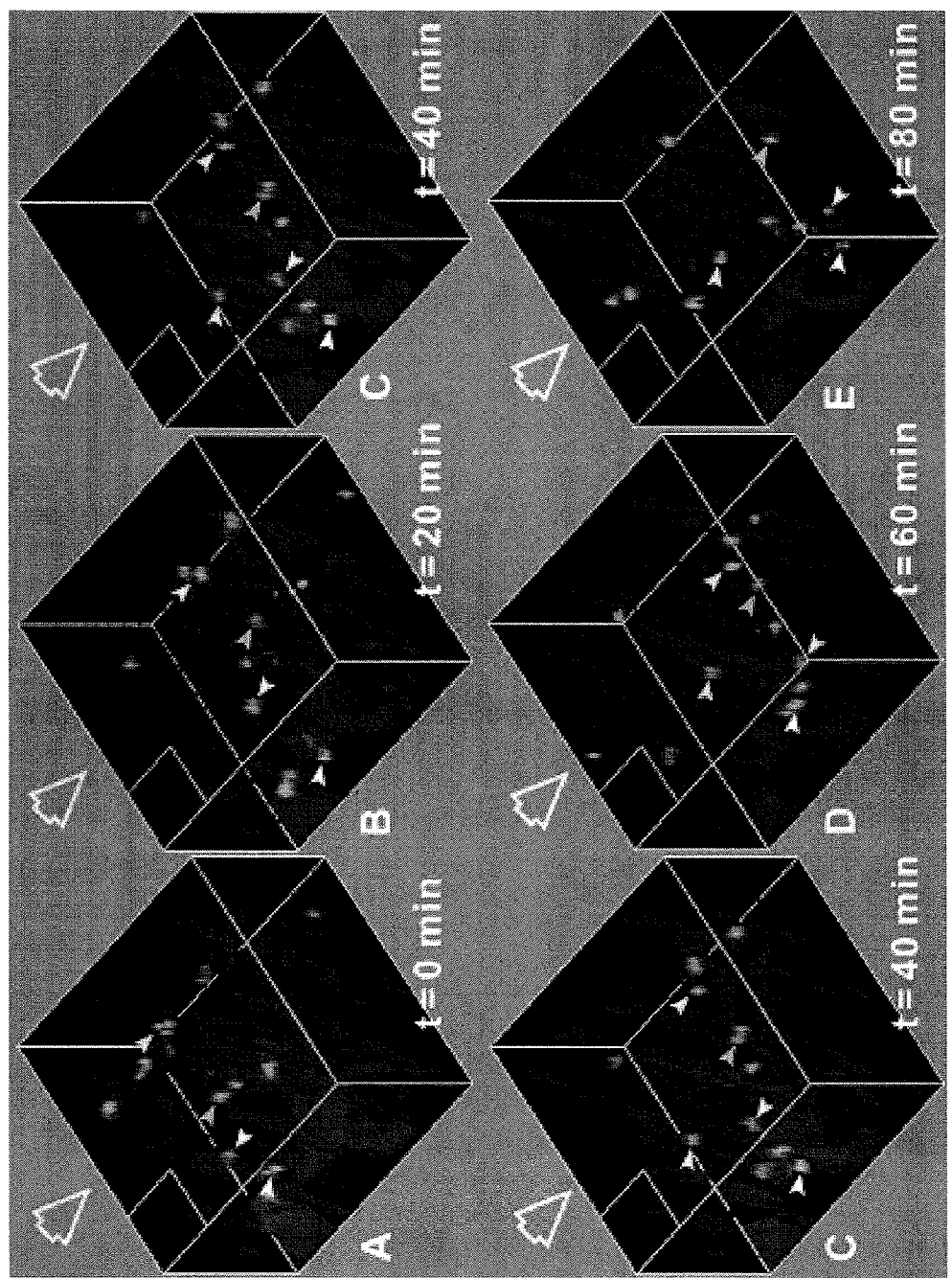
FIG. 31. These images were obtained in a Fischer 344 rat at 4 months of age. The coronary circulation was perfused with an oxygenated Tyrode solution containing rhodamine-labeled dextran and the growth factors were administrated at the time of observation. The first image was obtained within 15 minutes, which is the time required for the adjustment of the microscope on the epicardial surface of the heart. These five panels (A-E), panel C is shown twice, illustrate the same field examined at intervals of 20 minutes each. Red fluorescence corresponds to the distribution of the coronary vasculature and green fluorescence reflects EGFP-labeled cells in vivo. Arrowheads of various colors point to EGFP-positive cells moving in the direction of the large open arrows over a period of 80 minutes. In all panels, EGFP moving cells were outside of the coronary vessels, suggesting that the coronary circulation was not implicated in the migration of EGFP-positive cells (color arrowheads) within the myocardium.
Figure 32:
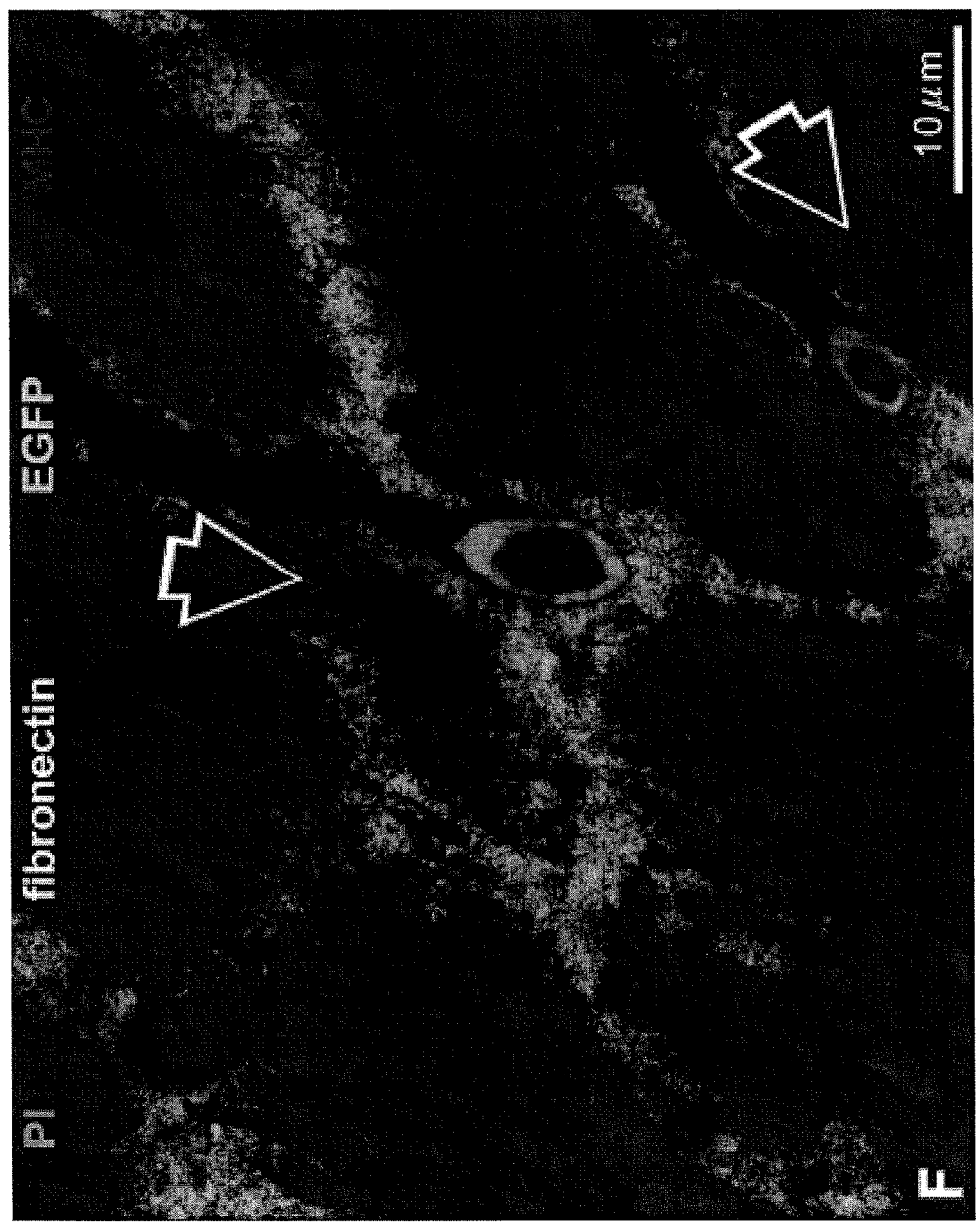
FIG. 32. Migrating EGFP-positive cells were located within tunnels defined by interstitial fibronectin (yellow). Large arrows point to the direction of migration of the EGFP-positive cells.

To determine whether the translocation of EGFP-positive-cells occurred through the coronary circulation, the myocardial interstitium or both, the coronary vasculature was perfused with rhodamine-labeled dextran and HGF was injected at the time of observation (Urbanek et al. (2005) Circ. Res. 97: 663-673). Over a period of 5-6 hours, none of the moving EGFP-positive-cells were found within the lumen of coronary vessels (FIGS. 30 and 31), suggesting that CPC migrated through the interstitium. In fact, EGFP-positive-cells were detected within tunnels defined by interstitial fibronectin (FIG. 32).

Figure 33:
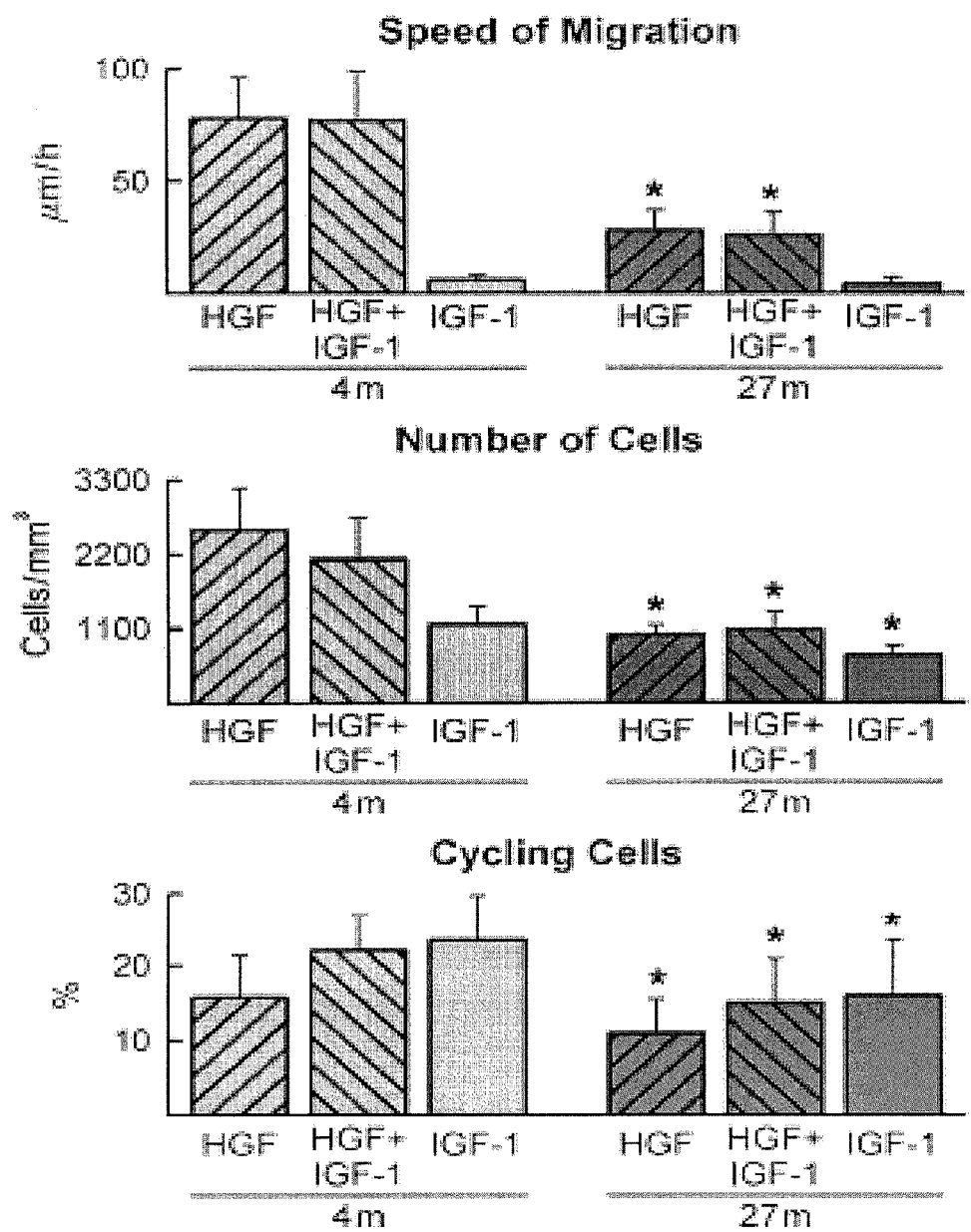
FIG. 33. Speed (upper panel), and number (central panel) of migrating and cycling (lower panel) EGFP-positive-cells in young (4 m) and old (27 m) hearts following growth factor administration. $*p<0.05$ versus 4 months.

HGF mobilized and translocated CPCs from the atrioventricular groove towards the LV mid-region. However, two aging effects were observed: the speed of migration and the number of migrating CPCs were significantly higher in young than in old hearts (FIG. 33). Because of the growth promoting effects of IGF-1 on CPCs (Linke et al. (2005) Proc. Natl. Acad. Sci. USA 102: 8966-8971; Urbanek et al. (2005) Circ. Res. 97: 663-673), IGF-1 was injected alone or in combination with HGF (FIG. 25) and the number and rate of migration of EGFP-positive-cells was determined together with the fraction of cycling EGFP-positive-cells. In young and old hearts, IGF-1 alone failed to stimulate the locomotion of CPCs (FIG. 33). Similarly, IGF-1 did not increase the migratory ability of HGF. However, IGF-1 resulted in a significant increase in the number of dividing CPCs in both young and old hearts (FIG. 33).

Figure 34:
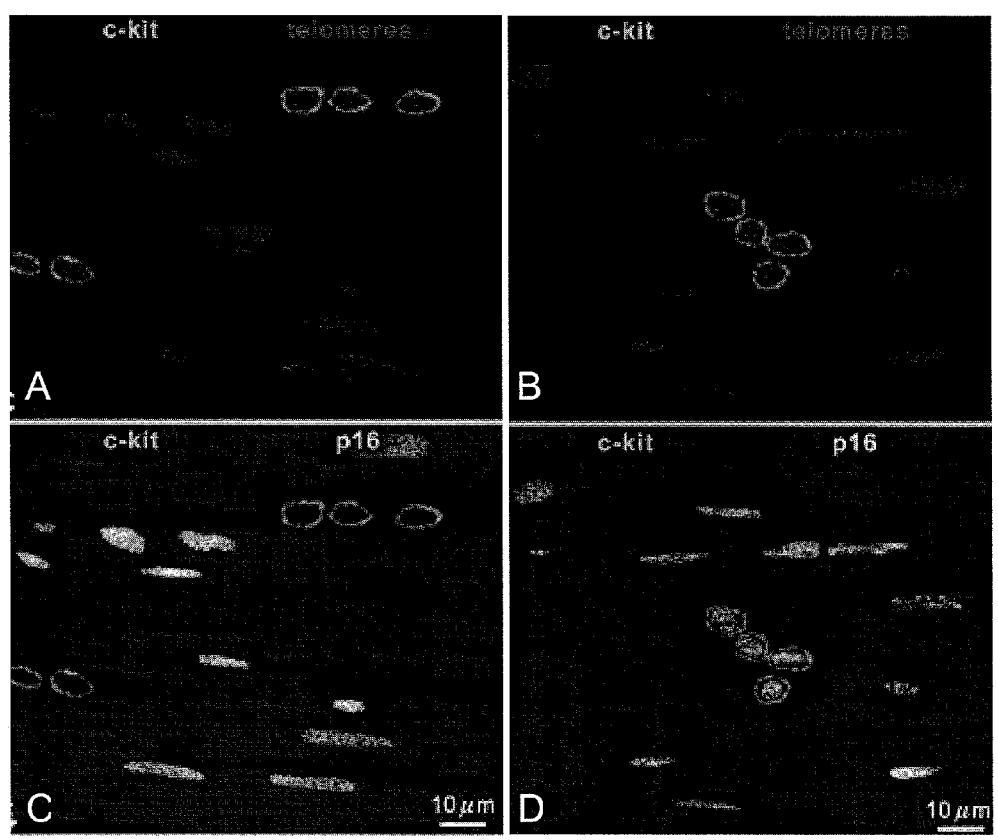
FIG. 34. Telomere length (A and B; magenta) in migrating CPCs (A, c-kit, green) and in non-migrating CPCs (B). (C) Migrating CPCs are $p16^{INK4a}$-negative. Non-migrating CPCs are mostly $p16^{INK4a}$-positive (D, yellow).

Migrating CPCs and their early committed progeny had long telomeres and were $p16^{INK4a}$-negative. This was in contrast with the properties of the non-translocated CPCs present in the mid-region of control hearts injected with vehicle. These cells had short telomeres and frequently expressed $p16^{INK4a}$ (FIG. 34). These results suggest that functionally-competent CPCs were stored in atrial niches while aging effects were more prominent in the mid-region of the LV myocardium. Thus, aging attenuates but does not abolish the growth and migratory properties of CPCs.

Figure 35:
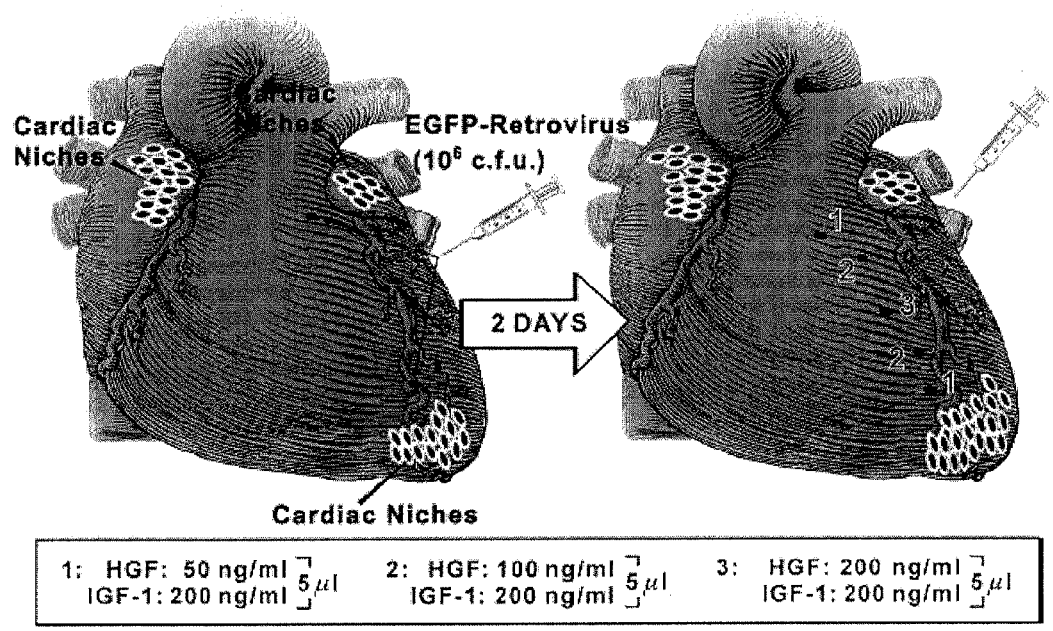
FIG. 35. Schematically, clusters of CPCs are stored in the atria and apex. These anatomical areas were injected with an EGFP-retrovirus to infect cycling CPCs and ECCs. Two days after infection, increasing concentrations of HGF together with IGF-1 were delivered intramyocardially from the atria and apex to the LV mid-region. The objective was to create a chemotactic gradient between stored CPCs and the damaged myocardium to promote translocation of functionally-competent primitive cells to the areas of tissue injury. Control animals were injected with vehicle. Treated and untreated animals were examined 45 days later.

B. Mobilized Cardiac Stem Cells Generate New Myocytes to Repair Age-Related Myocardial Damage Based on these observations, we tested whether the negative effects of aging on the heart could be reversed by activation of resident CPCs. HGF and IGF-1 were injected intramyocardially in rats at 15, 20 and 27 months of age. These ages were selected because organ damage becomes apparent at ~15 months and increases at 20 months although ventricular function is preserved (Kajstura et al. (1996) Am. J. Physiol. 271: H1215-1228). At 27 months, extensive tissue injury is present together with overt heart failure (Wei (1992) Am. J. Physiol. Renal. Physiol. 289: F1144-F1152; Kajstura et al. (1996) Am. J. Physiol. 271: H1215-1228). Since CPCs are distributed predominantly in the atria and apex, two chemotactic gradients from these areas towards the LV mid-region were created to enhance CPC translocation, growth and differentiation (FIG. 35). The animals were sacrificed 45 days later. Two days prior to growth factor administration, the atrioventricular groove and the apex were injected with the EGFP-retrovirus to label cycling CPCs. Only occasionally EGFP-positive-cells were not CPCs. However, these EGFP-positive-non-CPCs were not mobilized by HGF, IGF-1 or both. Therefore, the presence of EGFP-positive-cells in the LV mid-region, distant from the sites of infection, was indicative of CPC migration.

Figure 36:
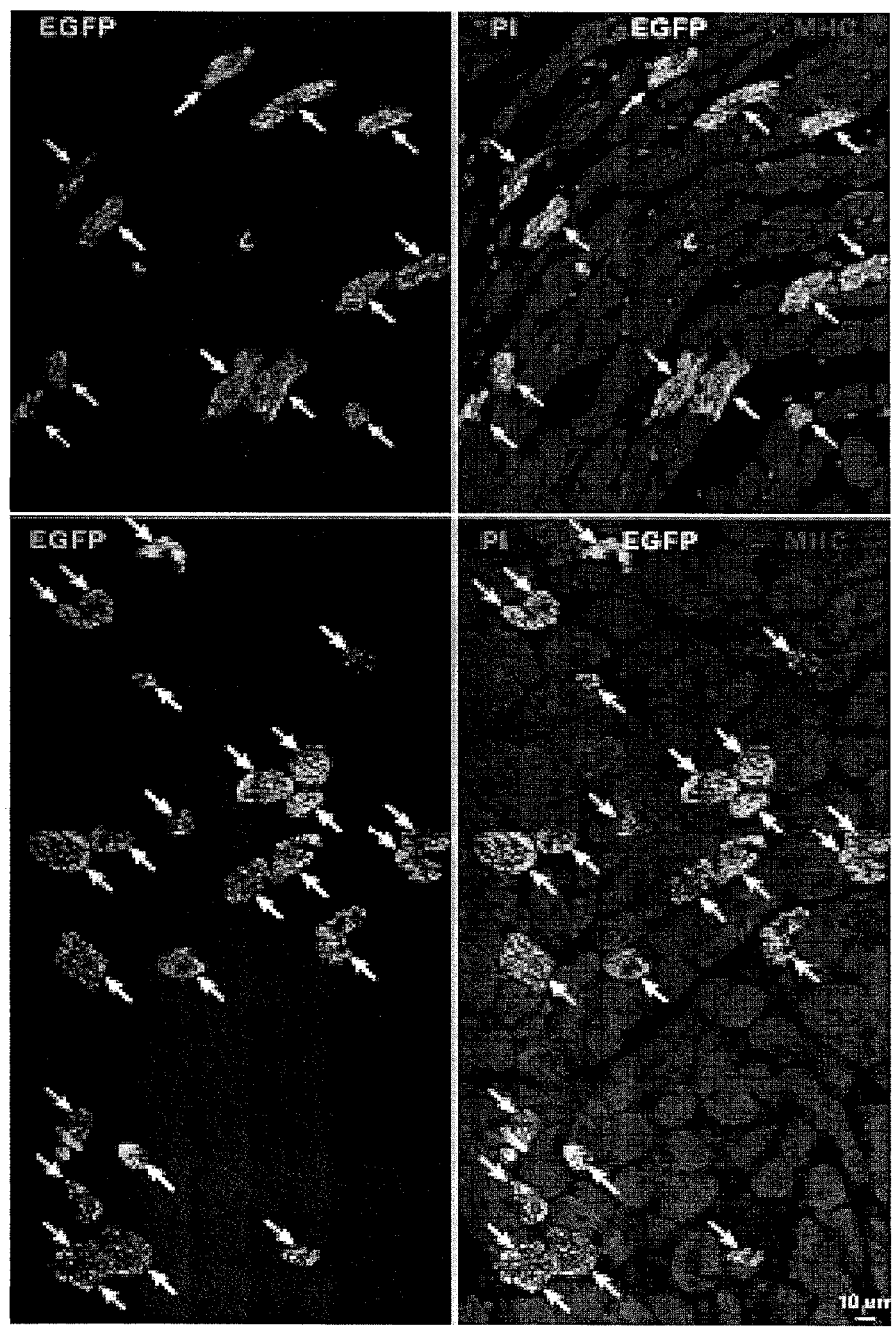
FIG. 36. Newly formed EGFP-positive cardiomyocytes (left panels: EGFP, green; right panels: MHC, red; arrows) in 28-29 months hearts treated with growth factors.
Figure 37:
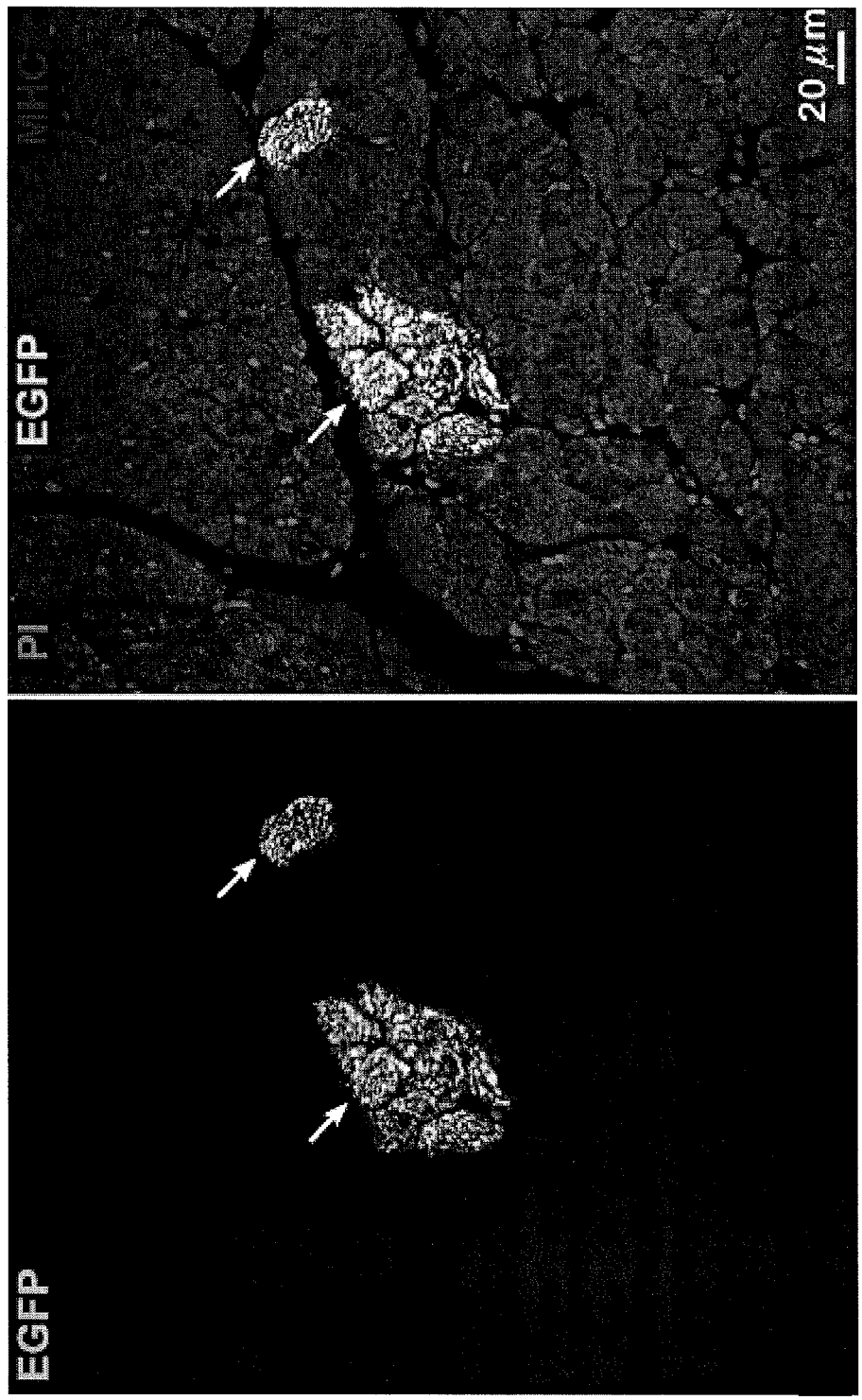
FIG. 37. Newly formed EGFP-positive-cardiomyocytes in treated hearts at 16-17 m (left panel: EGFP, green; right panel: MHC, red; arrows).
Figure 38:
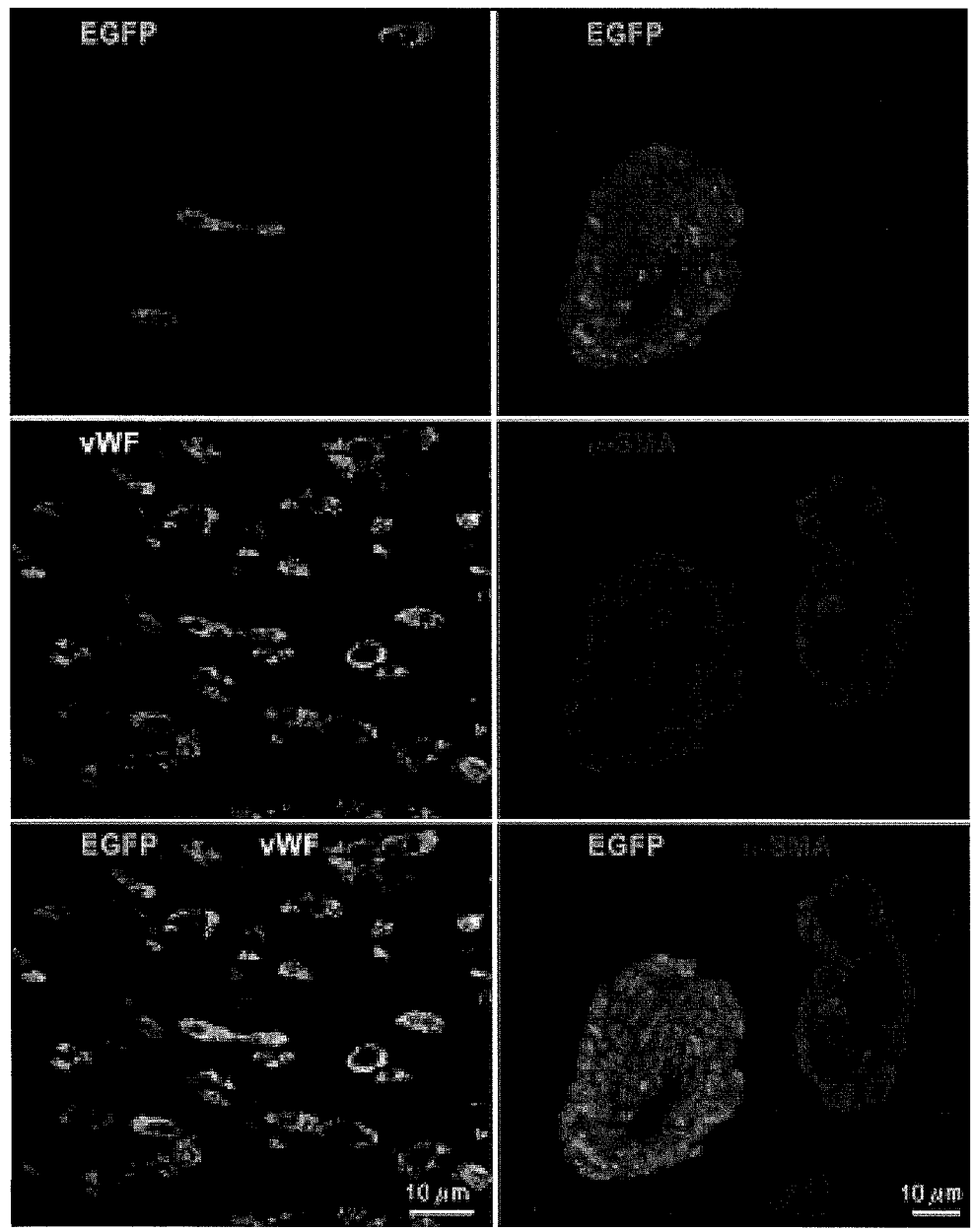
FIG. 38. Newly formed EGFP-positive capillaries in treated hearts at 21-22 m (left panel, upper panel: EGFP, green; central panel: vWF, white; lower panel: merge) and arterioles in treated hearts at 28-29 m (right panel, upper panel: EGFP, green; central panel: α-SMA, red; lower panel: merge).
Figure 39:
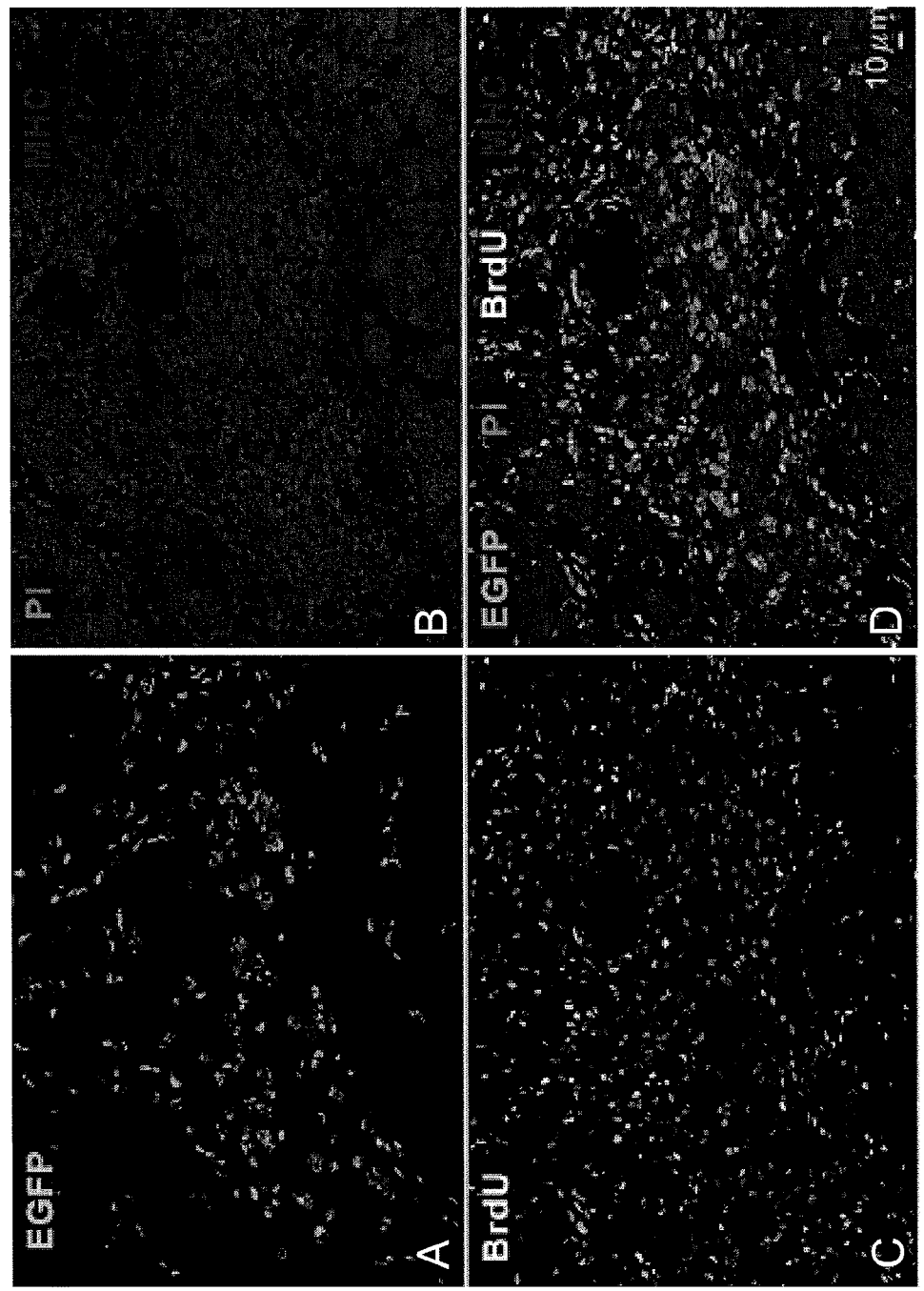
FIG. 39. Area of myocardial regeneration. EGFP, green (A); MHC, red (B); BrdU, white (C) and merge of A, B and C (D).
Figure 40:
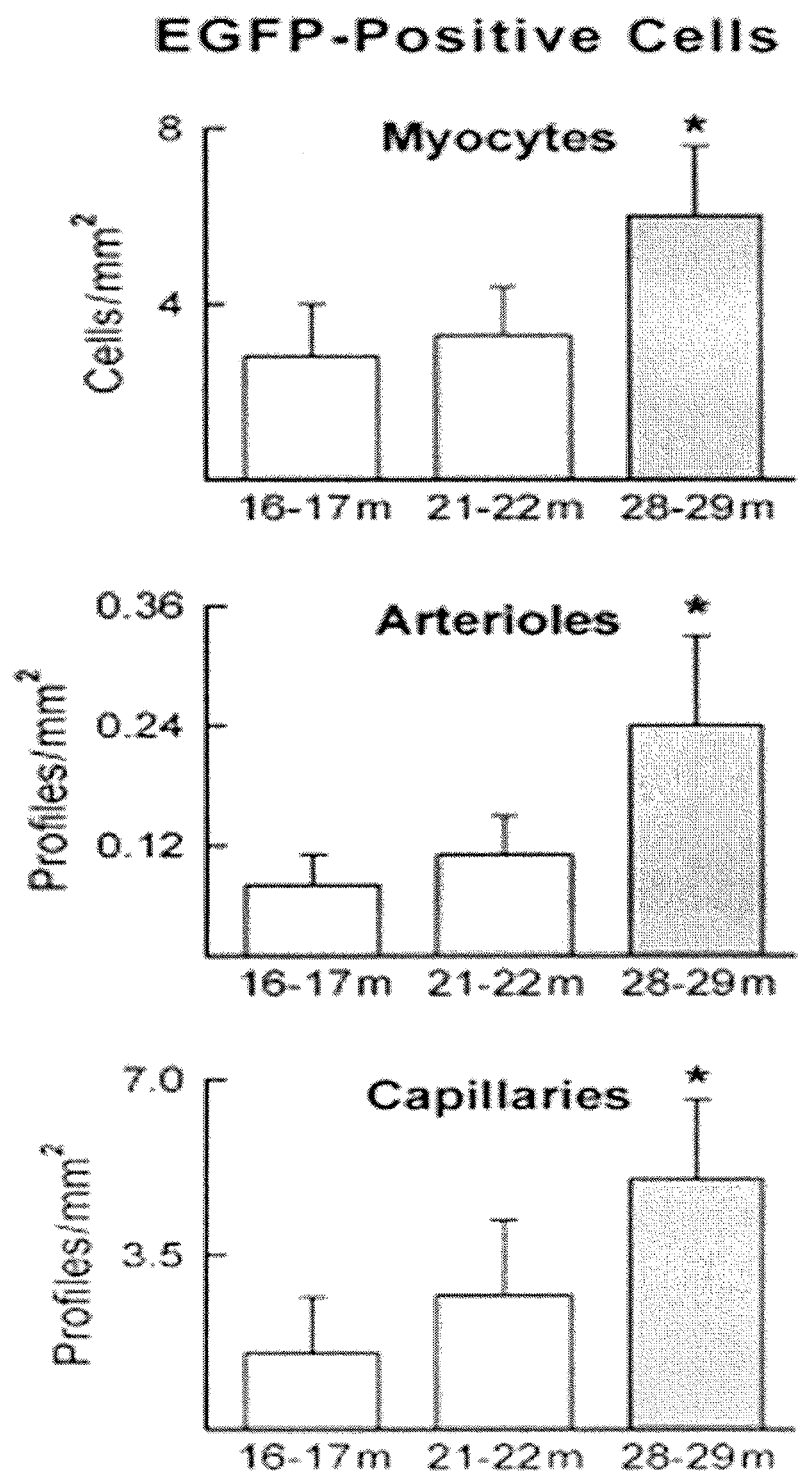
FIG. 40. Newly formed EGFP-positive-cardiomyocytes, capillaries, and arterioles in treated hearts at 16-17 m, 21-22 m, and 28-29 m, respectively. $*p<0.05$ versus 16-17 and 21-22 months.

EGFP-positive-differentiated-myocytes were identified together with coronary resistance arterioles and capillary structures in the mid-region of the LV in all treated rats (FIGS. 36-38). Conversely, EGFP-positive-myocytes and vessels were not detected in untreated animals. Newly formed myocytes were found in small clusters or scattered throughout the myocardium. Frequently, groups of regenerated developing myocytes replaced foci of myocardial damage (FIG. 39). Quantitatively, the number of EGFP-positive myocytes per mm$^2$ of myocardium was significantly higher in animals at 28-29 months of age than in animals at 16-17 and 21-22 months. A similar response was observed for coronary vessels (FIG. 40).

Figure 41:
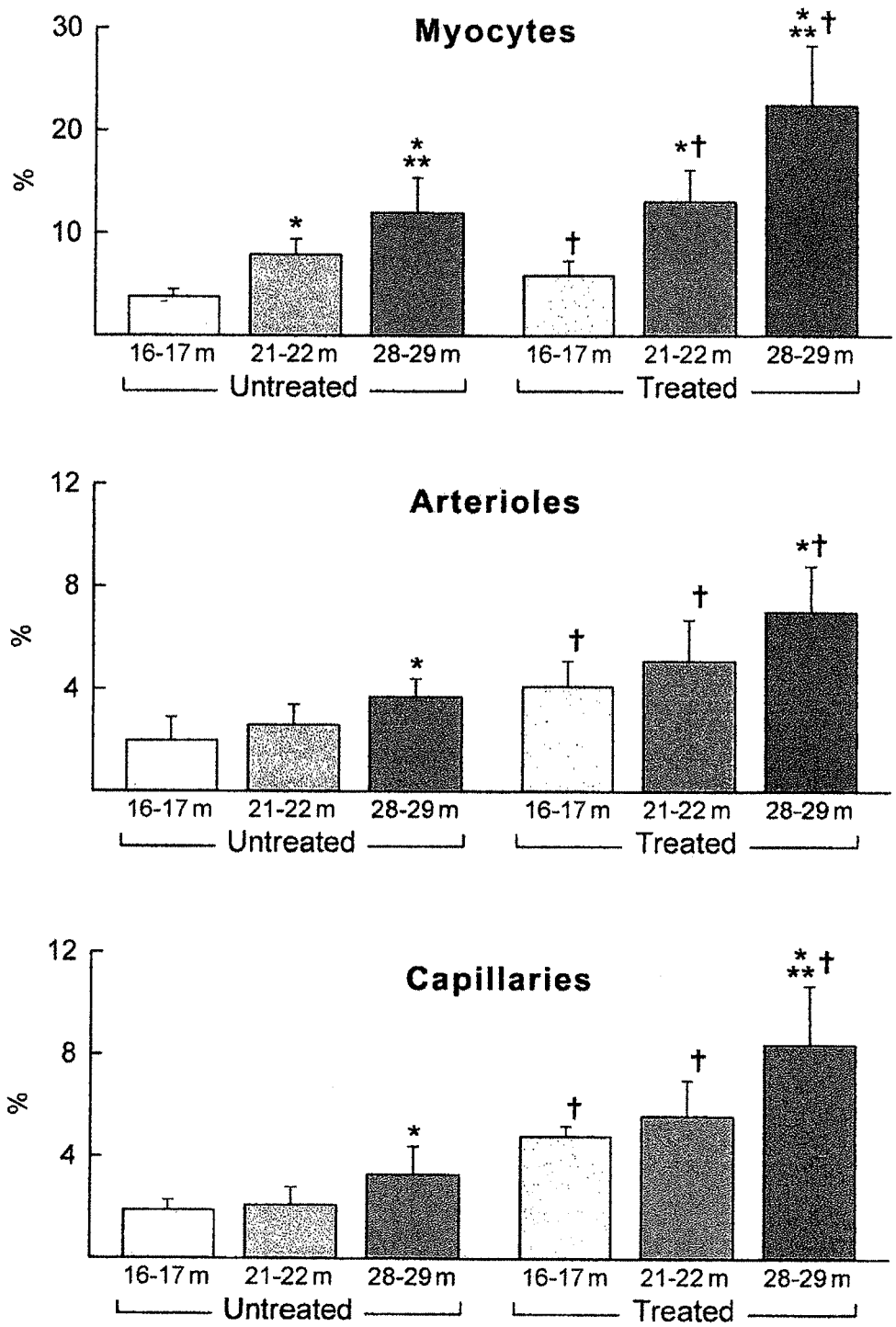
FIG. 41. BrdU-positive-myocytes (upper panel) and coronary arterioles (central panel) and capillaries (lower panel). $*p<0.05$ versus 16-17 months. $**p<0.05$ versus 21-22 months and $\p<0.05$ versus untreated animals.
Figure 42:
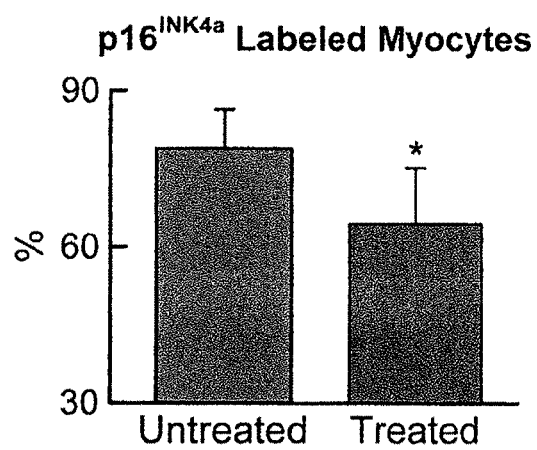
FIG. 42. $p16^{INK4a}$-positive myocytes. $*p<0.05$ versus untreated hearts at 28-29 months.

EGFP-labeled structures reflected only in part the extent of tissue regeneration since ~9-12% CPCs were infected by the EGFP-retrovirus. Thus, BrdU was given after the delivery of growth factors or vehicle and was continued throughout the experiment. With this approach, cumulative myocyte and vessel formation was determined with aging alone and together with growth factor therapy. In the absence of treatment, myocyte and vessel growth increased with age pointing to the ability of the old heart to react partly to tissue injury. Treatment with growth factors increased cardiomyocyte formation 55%, 66% and 88% at 16-17, 21-22 and 28-29 months, respectively (FIG. 41). Vessel regeneration also occurred but not to the same extent of myocytes. New myocytes in treated hearts at 28-29 months decreased by 20% the number of p16$^{INK4a}$-positive-cells (FIG. 42) and this change was reflected by the increase in BrdU-labeled-myocytes. Therefore, in the senescent myocardium functionally-competent CPCs can be coaxed to acquire the myocyte and vascular lineage impacting on the structure of the old heart.

C. Activation of Resident Cardiac Stem Cells Attenuates the Functional Effects of Aging on the Heart and Extends Lifespan Before sacrifice, hemodynamic parameters were obtained in rats non-injected, injected with vehicle (untreated) or with growth factors (treated). Animals were anesthetized with chloral hydrate (300 mg/kg b.w., i.p.), and the right carotid artery was cannulated with a microtip pressure transducer (SPR-612, Millar Instruments) connected to an A/D converter (iWorx 214) and a computer system. The catheter was advanced into the left ventricle (LV) chamber for the evaluation of LV end-diastolic pressure (LVEDP), systolic pressure (LVSP), developed pressure (LVDP) and +and−dP/dt in the closed-chest preparation (Kajstura et al. (1996) Am. J. Physiol. 271: H1215-1228; Leri et al. (1998) J. Clin. Invest. 101: 1326-1342; Beltrami et al. (2003) Cell 114:763-776; Urbanek et al. (2005) Circ. Res. 97: 663-673). Wall thickness measurements in combination with the radius of the LV chamber (see below) and LVEDP were employed to compute diastolic wall stress.

Following the collection of hemodynamic measurements, the abdominal aorta was cannulated with a polyethylene catheter filled with phosphate buffer (0.2 M, pH 7.4) and heparin (100 IU/ml). In rapid succession, the heart was arrested in diastole by injection of cadmium chloride (100 mM) through the aortic catheter and perfusion with phosphate buffer was conducted for ~3 minutes. The thorax was opened and the right atrium was cut to allow drainage of blood and perfusate. The heart was then fixed by perfusion with 10% phosphate-buffered formalin. Perfusion pressure was adjusted to mean arterial pressure. Throughout the procedure, the LV chamber was filled with fixative from a pressure reservoir set at a height equivalent to the in vivo measured end-diastolic pressure (Kajstura et al. (1996) Am. J. Physiol. 271: H1215-1228; Leri et al. (1998) J. Clin. Invest. 101: 1326-1342; Beltrami et al. (2003) Cell 114:763-776; Urbanek et al. (2005) Circ. Res. 97: 663-673). After fixation, the heart was dissected and the weights of the right ventricle and LV inclusive of the interventricular septum were recorded. The major longitudinal axis from the base to the apex of the heart was determined and the LV was serially sectioned into five rings perpendicular to this axis. The minimal and maximal cavitary diameters and wall thickness at the mid-region of the ventricle were obtained and, together with the longitudinal axis, were utilized to compute LV chamber volume (Dawn et al. (2005) Proc. Natl. Acad. Sci. USA 102: 3766-3771; Linke et al. (2005) Proc. Natl. Acad. Sci. USA 102: 8966-8971).

Figure 43:
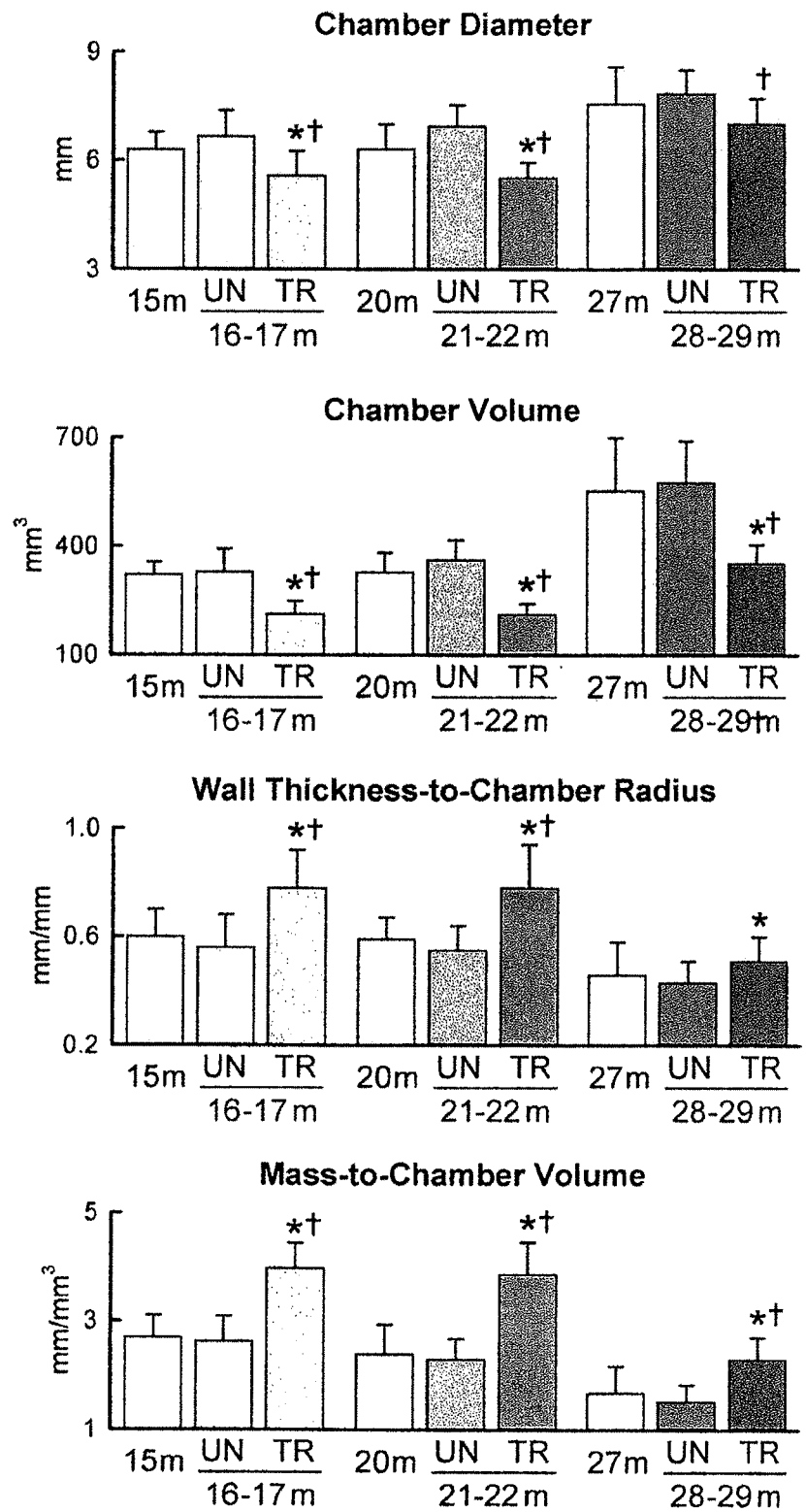
FIG. 43. LV anatomy at baseline (15, 20 and 27 months; white bars) and 45 days later in untreated (orange bars) and treated (blue bars) rats at 16-17, 21-22 and 28-29 months. $*p<0.05$ versus baseline and $\p<0.05$ versus untreated animals 45 days later.
Figure 44:
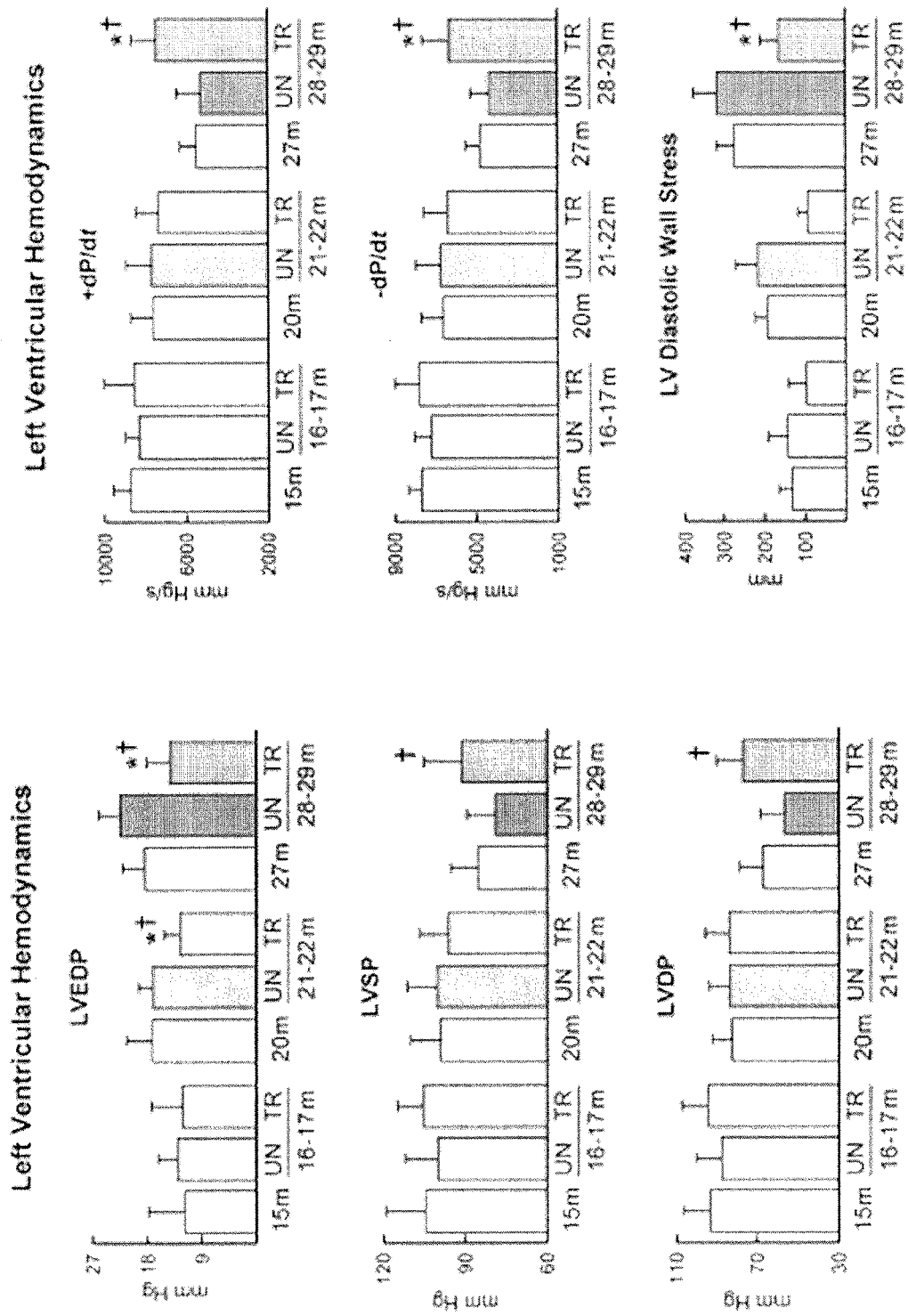
FIG. 44. LV hemodynamics at baseline (15, 20 and 27 months; white bars) and 45 days later in untreated (orange bars) and treated (blue bars) rats at 16-17, 21-22 and 28-29 months. $*p<0.05$ versus baseline and $\p<0.05$ versus untreated animals 45 days later.
Figure 45:
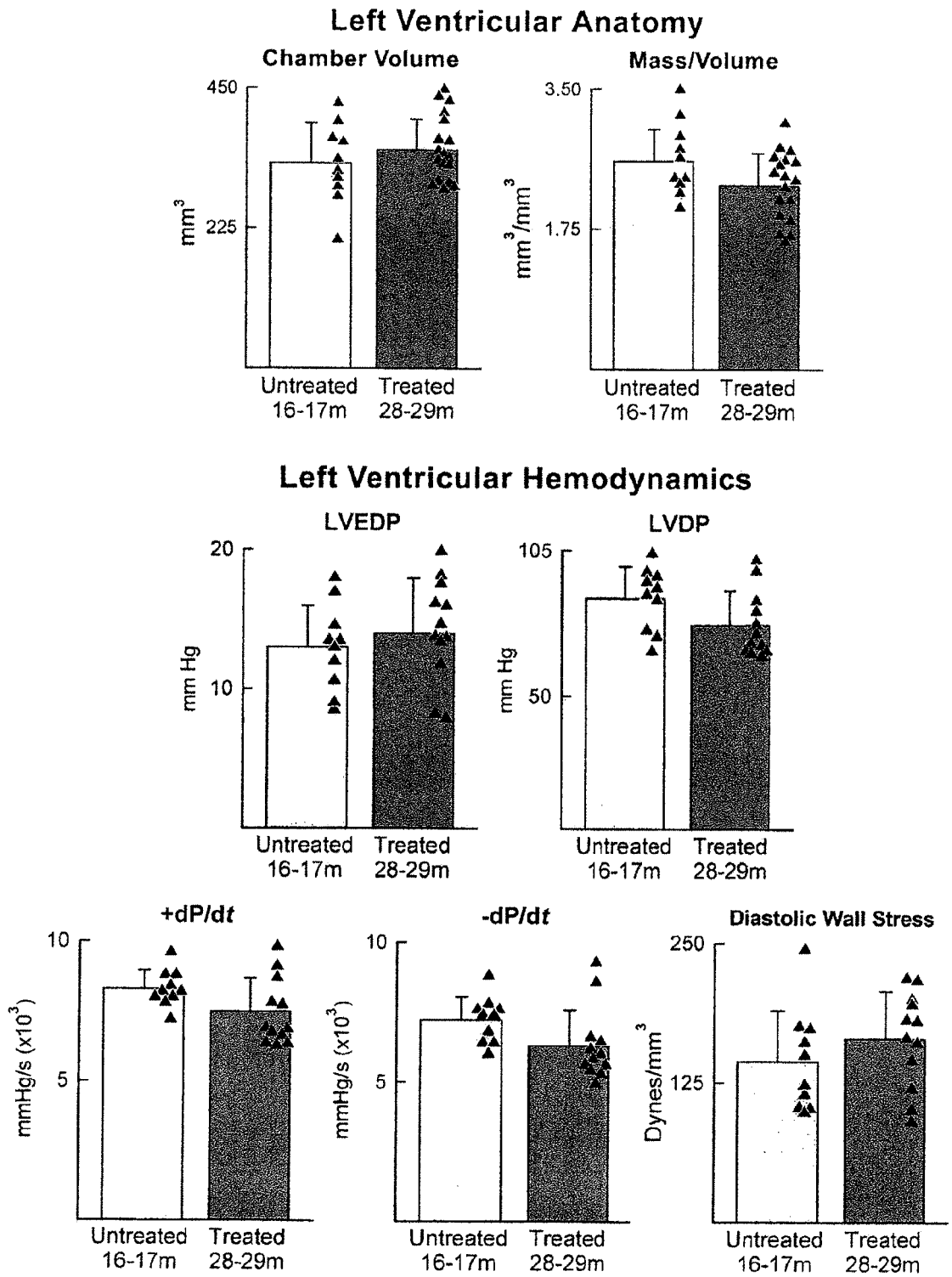
FIG. 45. Anatomy and hemodynamics of untreated hearts at 16-17 months and treated hearts at 28-29 months. Small triangles indicate individual values.

Myocardial regeneration mediated by CPC activation attenuated the aging effects on ventricular anatomy; LV chamber diameter and volume were reduced and wall thickness-to-chamber radius ratio and LV mass-to-chamber volume ratio increased at all ages (FIG. 43). These changes in cavitary dimension were accompanied by improvement in ventricular function of the senescent failing heart at 28-29 months. In the absence of treatment, heart failure at 27 months deteriorated further at 28-29 months. Conversely, following treatment, the alterations in LV end-diastolic pressure (LVEDP), systolic pressure (LVSP), developed pressure (LVDP), +dP/dt and −dP/dt and calculated diastolic wall stress found at 27 months were no longer apparent at 28-29 months (FIG. 44). Growth factor administration reversed the aging myopathy. The anatomy and function of treated hearts at 28-29 months became similar to the anatomy and function of untreated hearts one year younger, at 16-17 months (FIG. 45).

Invasive hemodynamics in rats can only be collected at sacrifice precluding multiple determinations. To strengthen the results above, echocardiograms were recorded in rats at 27 months, one day before treatment, and then 45 days later, prior to sacrifice, at 28-29 months. A group of rats injected with vehicle was similarly studied. Rats were anesthetized with ketamine (100 mg/kg b.w., i.p.), and echocardiographic parameters were collected utilizing an Acuson Sequoia 256c equipped with a 13-MHz linear transducer (Dawn et al. (2005) Proc. Natl. Acad. Sci. USA 102: 3766-3771; Linke et al. (2005) Proc. Natl. Acad. Sci. USA 102: 8966-8971). The anterior chest was shaved, and rats were placed in the left lateral decubitus position. A rectal temperature probe was placed, and the body temperature was carefully maintained between 37.0° C. and 37.5° C. with a heating pad throughout the study. The parasternal long-axis, parasternal short-axis, and apical four-chamber views were used to obtain 2D, M-mode. Systolic and diastolic anatomic parameters were obtained from M-mode tracings at the midpapillary level. Ejection fraction (EF) was calculated by the area-length method (Dawn et al. (2005) Proc. Natl. Acad. Sci. USA 102: 3766-3771; Linke et al. (2005) Proc. Natl. Acad. Sci. USA 102: 8966-8971).

Figure 46:
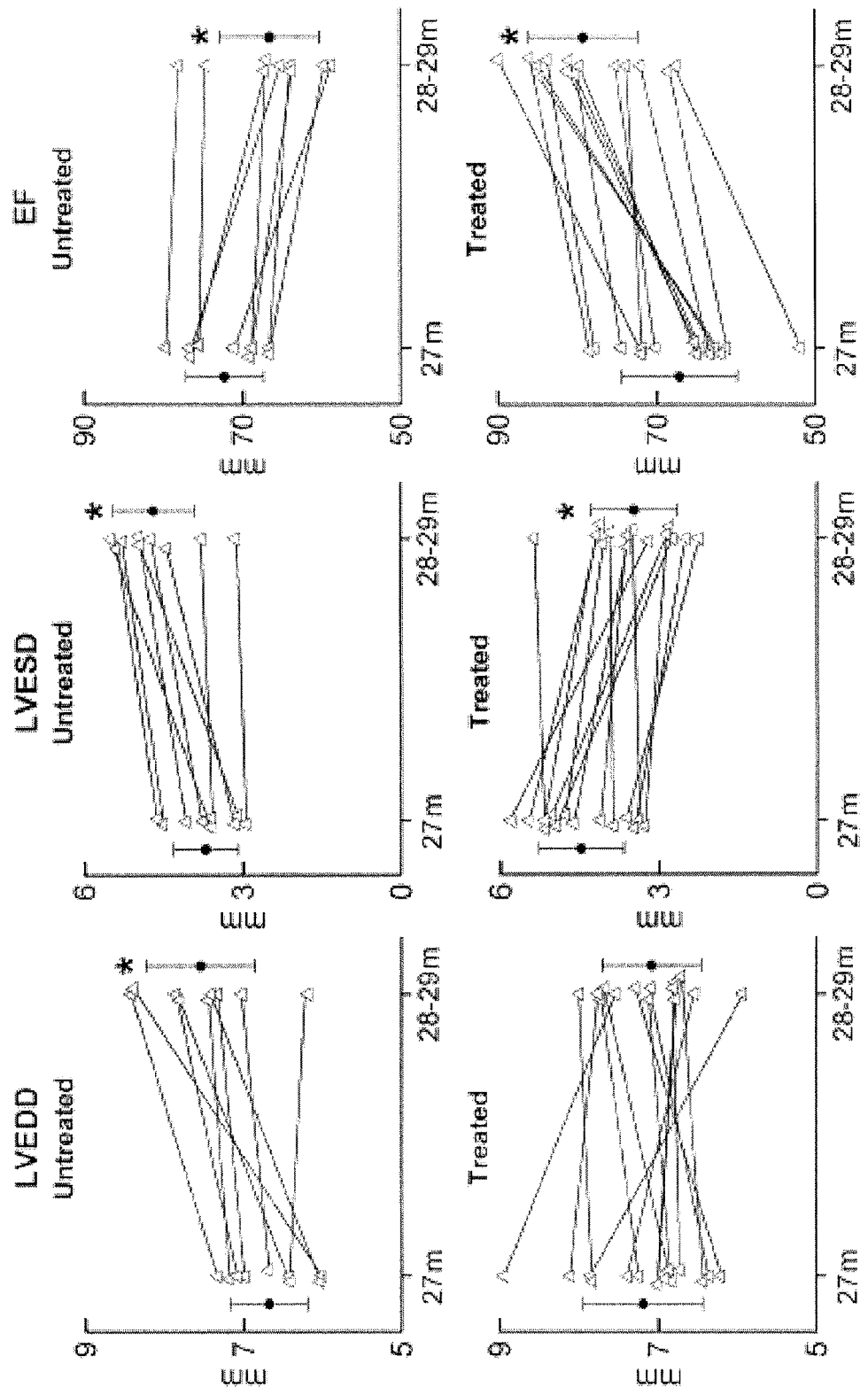
FIG. 46. Echocardiographic parameters at baseline in rats at 27 months and 45 days later in the absence and presence of treatment. $*p<0.05$ versus the same hearts at 27 months.
Figure 47:
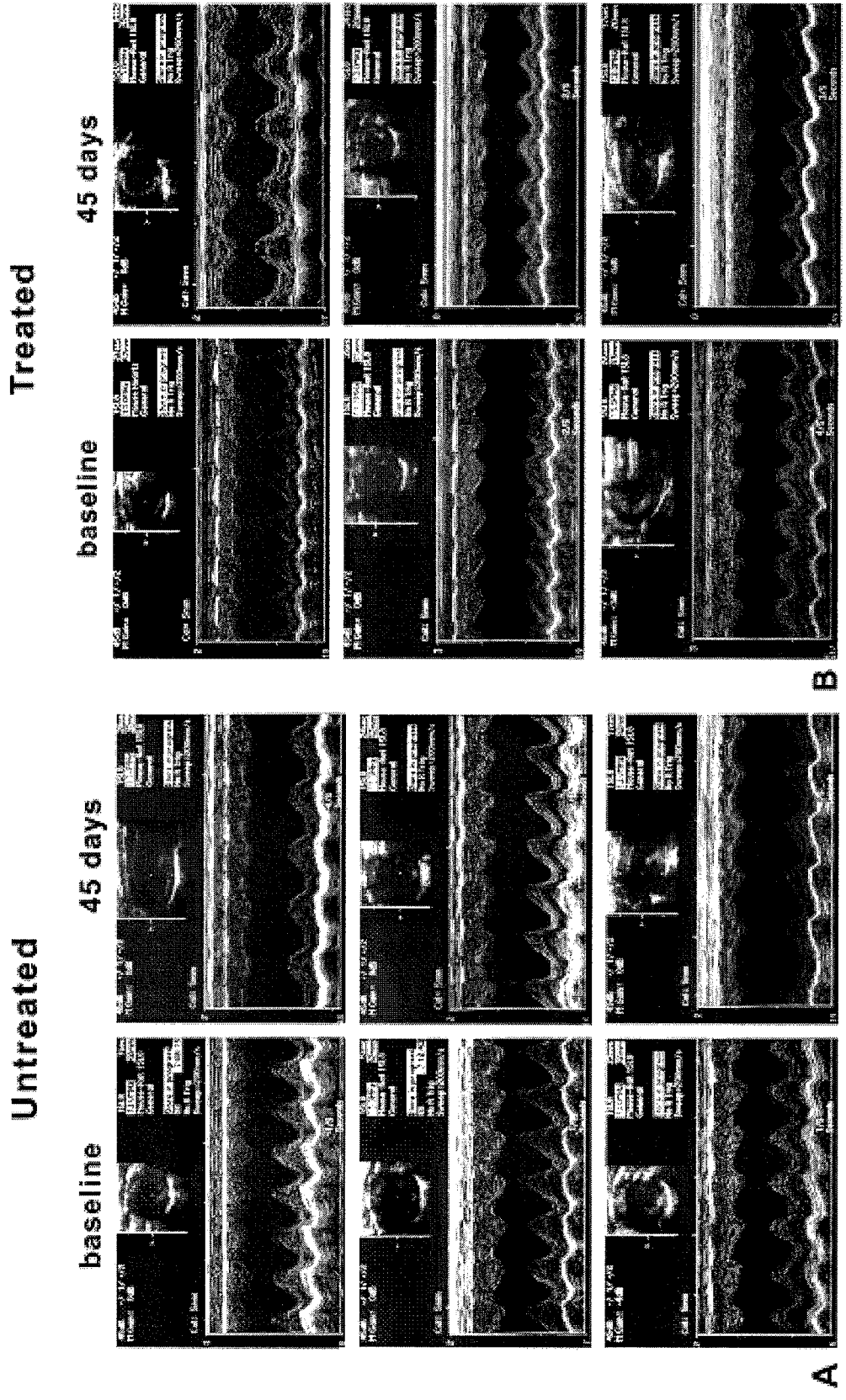
FIG. 47. M-mode echocardiography of rats at 27 months and 45 days later in the absence (A) and presence (B) of growth factor treatment. The improvement in cardiac performance with treatment is apparent.

Therapy significantly decreased end-diastolic and end-systolic LV diameters while ejection fraction increased 12 points, from 67±7% to 79±7%. In untreated rats, cardiac function deteriorated with time (FIG. 46). The improvement in cardiac performance with treatment was apparent when the early and late echocardiograms were compared (FIGS. 47A and B).

Figure 48:
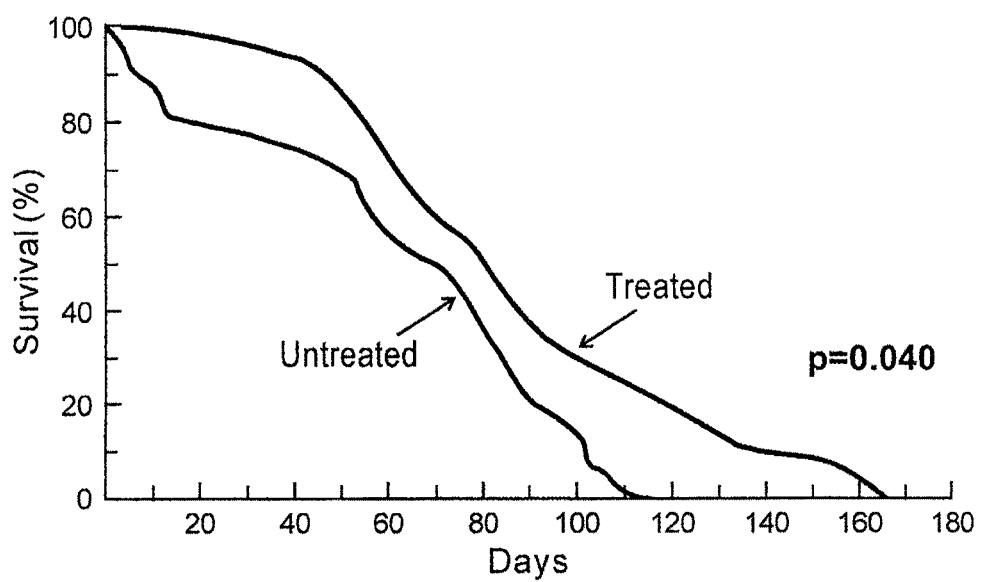
FIG. 48. Mortality in untreated and growth factor-treated animals at 27 months.

The final question was whether the improvement in cardiac function mediated by CPC activation and differentiation prolonged life in this model. For this purpose, a mortality study was conducted in a cohort of rats at 27 months. Together, 32 untreated and 48 treated rats were maintained under identical conditions and death was monitored over time. By 31 months, all untreated rats were dead. However, 28% of treated rats were alive at 31 months and the last animal died at 33 months (FIG. 48). Growth factor treatment increased life expectancy at 27 months by 44%, from 57 to 82 days. Thus, recovery from heart failure prolongs maximum lifespan in rats.

Example 4

Isolation of Non-Senescent Cardiac Stem Cells and their Use in Repair of Age-Related Cardiomyopathy Myocardial specimens are obtained from consenting patients who have undergone cardiac surgery. Samples are minced and seeded onto the surface of uncoated Petri dishes containing a medium supplemented with hepatocyte growth factor and insulin-like growth factor-1 at concentrations of 200 ng/ml. After ~2 weeks in cell culture, cells outgrown from the tissue are sorted for c-kit with immunobeads and cultured. Cell phenotype is defined by FACS and immunocytochemistry as described previously (Beltrami et al. (2003) Cell 114: 763-776; Orlic et al. (2001) Nature 410: 701-705; Urbanek et al. (2005) Proc. Natl. Acad. Sci. USA 102: 8692-8697). Individual human c-kit positive cells are seeded in single wells of Terasaki plates at a density of 0.25-0.5 cells/well (Beltrami et al. (2003) Cell 114: 763-776; Linke et al. (2005) Proc. Natl. Acad. Sci. USA 102: 8966-8971). Wells containing more than one cell are excluded. Clones generated from each of the wells seeded with individual c-kit positive cells are tested for telomere length and/or telomerase activity as described above in Example 1. Clones that have telomeres at least 5 kbp in length or telomerase activity that is at least 60% of the telomerase activity of control stem cells are selected (human non-senescent cardiac stem cells) and may be expanded in cell culture. Control cells for the comparison of telomerase activity may be freshly isolated c-kit positive cardiac cells from young (20-40 years) individuals. Preferably, the non-senescent cardiac stem cells are activated in vitro by exposure to one or more growth factors (e.g. hepatocyte growth factor and/or insulin-like growth factor-1) prior to administration.

Patients suffering from age-related cardiomyopathy or myocardial damage due to other causes, such as myocardial infarction, may receive at least one injection of non-senescent cardiac stem cells isolated as described above. C-kit positive-cells may be collected at P2 when ~200,000 c-kit positive-cells are obtained from each clone. The patient would receive at least one injection of the isolated non-senescent cardiac stem cells intramyocardially. Injections of growth factors, such as hepatocyte growth factor and insulin-like growth factor-1, may be administered simultaneously with the intramyocardial injection of the isolated stem cells. Alternatively, growth factors may be administered subsequent to the injection of the stem cells. The injected non-senescent stem cells would mobilize to areas of myocardial damage and differentiate into viable myocytes, endothelial cells, and smooth muscle cells to repair and/or regenerate the damaged tissue. The newly generated myocardium would be functional and contribute to the preservation of heart function and prevent organ failure.

Example 5

Mobilization of Implanted Non-Senescent Cardiac Stem Cells Complements Angiotensin II Blockade in the Infarcted Heart Two of the major complicating factors of myocardial infarction (MI) are the loss of muscle mass and cavitary dilation, which both contribute to negative left ventricular (LV) remodeling and to the depression in cardiac performance. To ameliorate these factors of MI, non-senescent cardiac stem cells (CSC) isolated as described in Example 4 are implanted intramyocardially into mice subsequent to the induction of myocardial infarction. The non-senescent CSCs may be activated by exposure to one or more cytokines, such as hepatocyte growth factor and/or insulin-like growth factor-1 prior to administration. An AT1 receptor antagonist, such as losartan, is administered to the mice at a dose of approximately 20 mg/kg body weight/day, to attenuate cellular hypertrophy, and, thereby, the expansion in chamber volume. MI is produced in mice and the animals are subdivided into four groups: 1. Sham-operated (SO); 2. MI only; 3. MI+AT1 receptor blocker; 4. MI+AT1 receptor blocker+non-senescent CSC. One month after MI, animals are sacrificed, and LV function, infarct dimension and cardiac remodeling are evaluated. Myocardial regeneration is also measured in mice treated with non-senescent CSC. The group receiving implantation of non-senescent CSC and the AT1 receptor blocker is expected to have a more favorable outcome of the damaged heart in teens of chamber diameter compared to animals that received the AT1 receptor blocker alone and animals that were not treated. For example, chamber diameter and chamber volume are reduced compared to untreated and AT1 receptor blocker-treated animals. The LV-mass-to-chamber volume ratio is higher in MI+AT1 receptor blocker+non-senescent CSC than in MI and MI+AT1 receptor blocker groups. In addition, tissue repair in the MI+AT1 receptor blocker+non-senescent CSC group is increased exhibiting new myocytes, arterioles, and capillaries, which act to reduce MI size. Echocardiographically, contractile function reappears in the infarcted region of the wall of mice treated with the AT1 receptor blocker and non-senescent CSCs. Hemodynamically, the MI+AT1 receptor blocker+non-senescent CSCs group has a lower LVEDP, and higher+ and −dP/dt. In conclusion, the positive impact of the AT1 receptor blocker on ventricular remodeling is enhanced by the process of cardiac repair mediated by translocation of implanted non-senescent CSCs to the infarcted area. Mobilized CSCs reduce infarct size and ventricular dilation and, thereby, ameliorate further the contractile behavior of the infarcted heart.

Example 6

Human Cardiac Stem Cells with Regenerative Capacity can be Isolated from the Aging and Failing Heart The objective of this example is to demonstrate that telomeric length is a critical variable of the growth behavior of human cardiac progenitor cells (hCPCs), also known as human cardiac stem cells. Progenitor cells with short telomeres may have little or no role in cardiac homeostasis and repair and therefore may have minimal or no therapeutic value for the management of human heart failure. hCPCs with short telomeres can be eliminated from the pool of cells to be implemented clinically to enhance the efficacy of cell therapy for the decompensated heart. The use of hCPC subsets with significant growth reserve would decrease dramatically the number of cells to be administered to achieve a positive clinical end-point. Additionally, this approach may help avoid the consequences of age, sex and type and duration of the cardiac disease on the pool of functionally-competent hCPCs.

Figure 49:
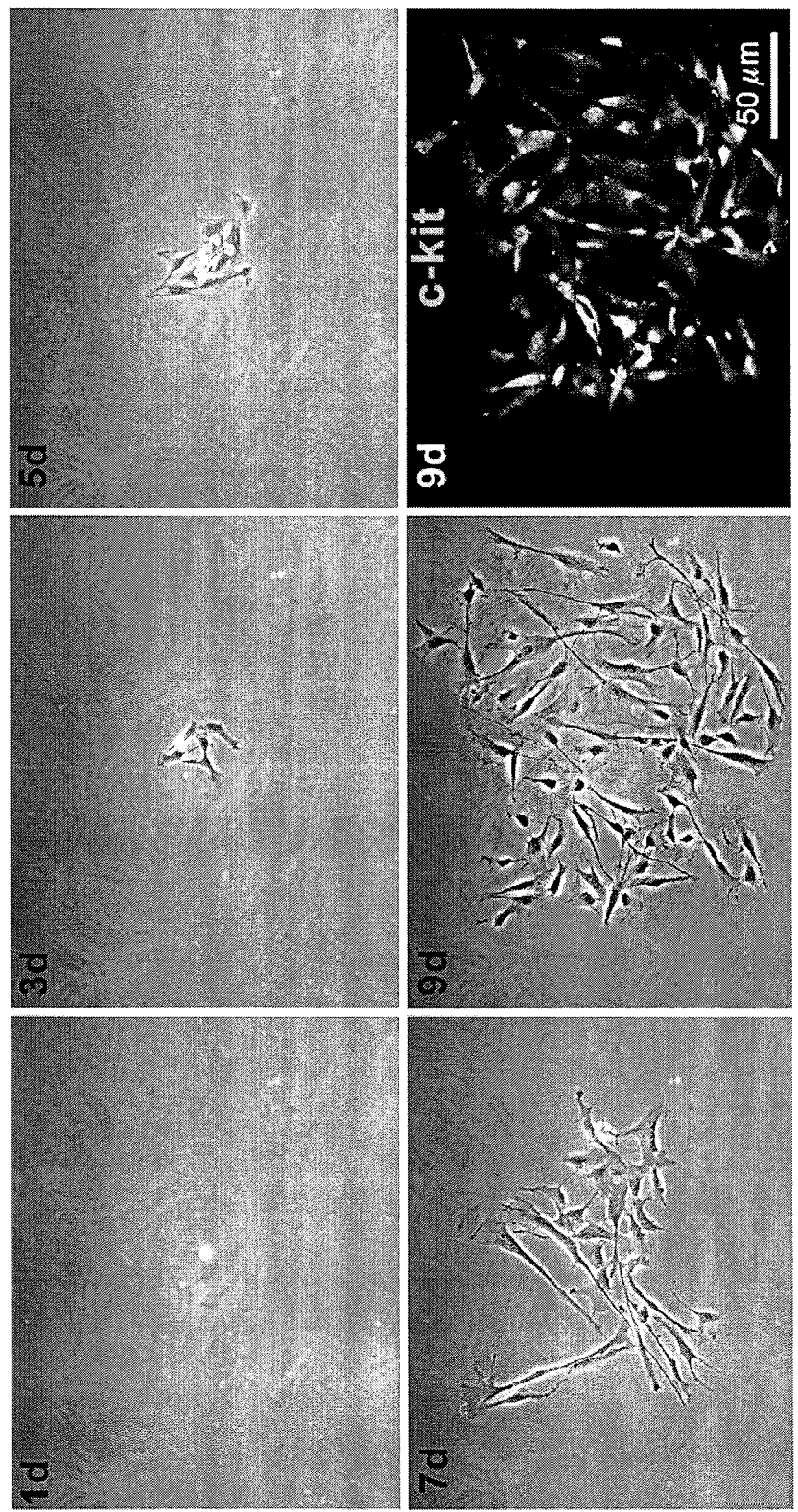
FIG. 49. Clones derived from single hCPCs isolated from myocardial samples. From a single hCPC, a multicellular clone was developed in 9 days; the hCPC clone is positive for c-kit (green).
Figure 50:
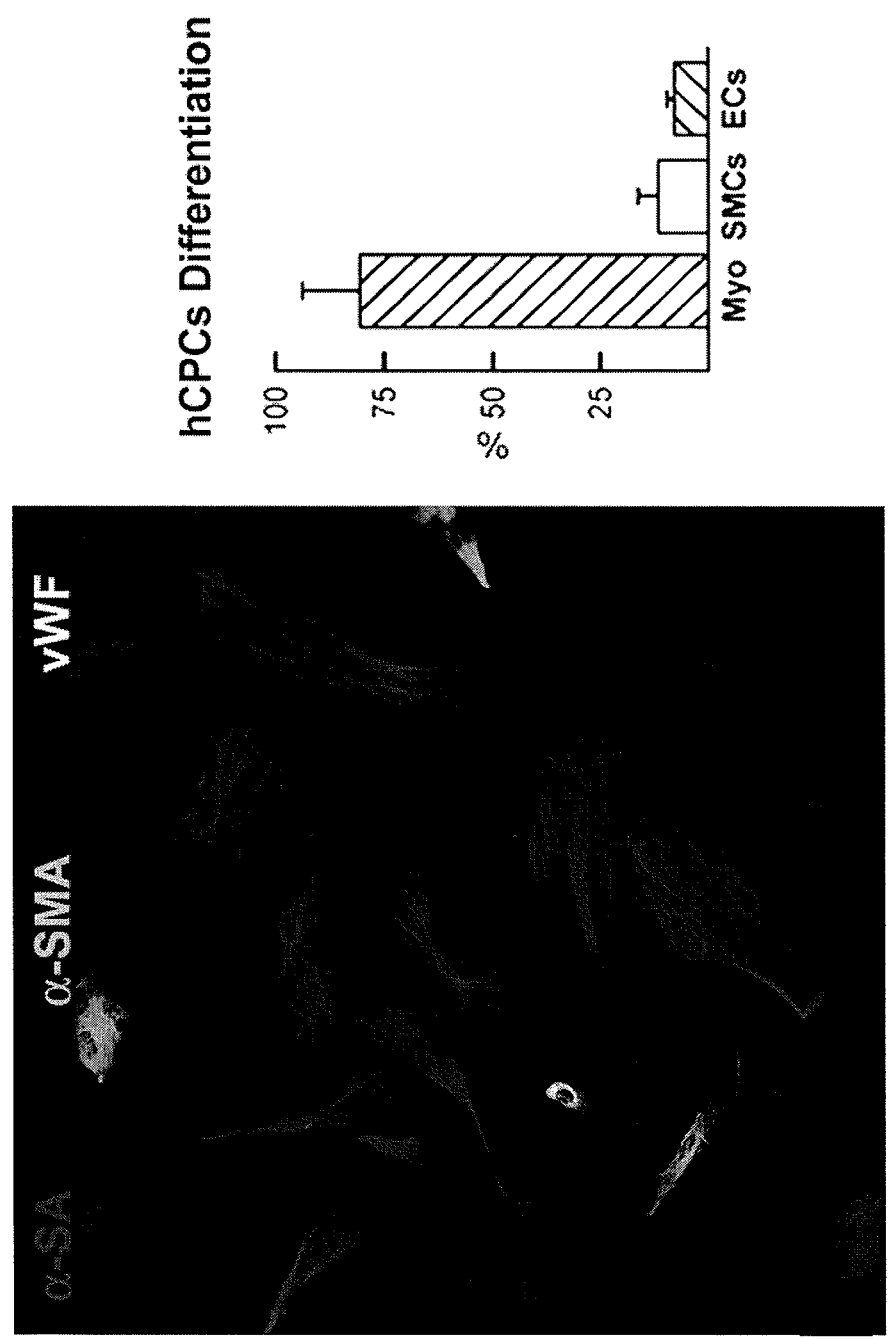
FIG. 50. Clonogenic hCPCs differentiate predominantly into myocytes (α-SA, red) but also into smooth muscle cells (SMCs; α-SMA, green) and endothelial cells (ECs; vWF, yellow).
Figure 51:
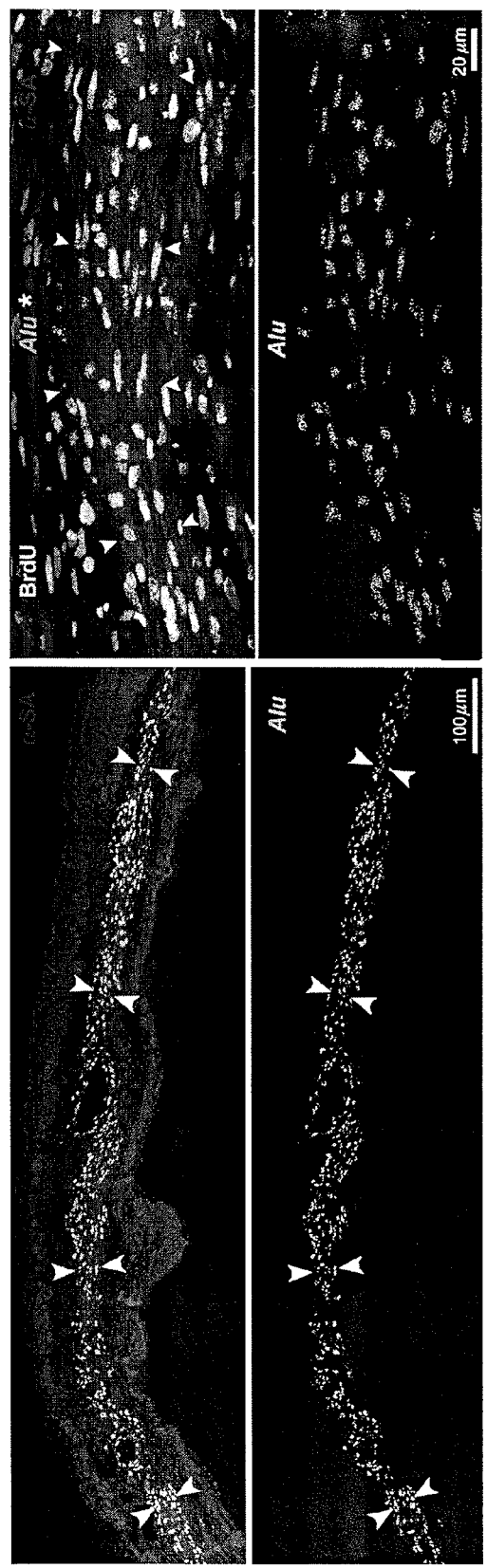
FIG. 51. Human myocardium (arrowheads) in an infarcted mouse 21 days after injection of hCPCs (left panel) and in an infarcted rat 14 days after injection of hCPCs (right panel). New myocytes are positive for α-SA (red). The human origin of the myocardium was confirmed by the detection of human DNA sequences for Alu in nuclei (green); BrdU was given to label newly formed myocytes (right upper panel, white).

A. Cardiac Stem Cells Isolated from Human Myocardial Tissue can be Expanded In Vitro and Used to Repair Damaged Myocardium Human cardiac progenitor cells (hCPCs) were isolated from small samples of myocardium obtained from patients undergoing cardiac surgery and extracorporeal circulation. The discarded samples, such as the atrial appendage, were utilized for this purpose. Following hCPC isolation from the myocardium, individual hCPCs, which were negative for lineage markers and positive for c-kit, were plated in a single well of a Terasaki culture plate and clonally expanded in vitro as described in Bearzi et al. (2007) Proc Natl Acad Sci USA., Vol. 104:14068-14073 (FIG. 49). These clonogenic hCPCs differentiated predominantly into myocytes, but also produced smooth muscle cells and endothelial cells (FIG. 50). To document that the in vitro expanded hCPCs were capable of differentiating, reaching functional competence and repairing the damaged myocardium, infarcts were produced in immunodeficient mice and immunosuppressed rats and the hCPCs were injected in the contracting myocardium bordering the infarct shortly after coronary artery ligation. As shown in FIG. 51, hCPCs regenerated the damaged myocardium with human myocytes and coronary vessels reducing the magnitude of ischemic injury and improving the performance of the infarcted heart.

B. Telomere Length and Telomerase Activity in Clonally Expanded Human Cardiac Stem Cells Proliferation of stem cells is regulated by telomerase activity and telomeric length (Morrison et al. (1996) Immunity, Vol. 5:207-216; Allsopp et al. (2003) Blood, Vol. 102:517-520; Lansdorp (2005) Ann N Y Acad. Sci., Vol. 1044:220-227; Armstrong et al. (2005) Stem Cells, Vol. 23:516-529; and von Zglinicki (2000) Ann N Y Acad. Sci., Vol. 908:99-110). During each division, the semi-conservative DNA replication has an intrinsic obstacle, consisting of the inability of conventional DNA polymerase to complete the synthesis of the lagging strand of the replication fork (Nugent and Lundblad V (1998) Genes Dev., Vol. 12:1073-1085). The end-replication problem would cause progressive shortening of DNA. In eukaryotic cells, chromosomes are preserved by protective caps called telomeres and telomerase is the enzyme capable of keeping intact the length of telomeres (Greider (1990) Bioessays, Vol. 12:363-369). Telomerase is a reverse transcriptase which extends the 3' chromosomal ends by utilizing its own RNA as a template (Blackburn (1992) Ann Rev Biochem, Vol. 61:113-129). Telomerase activity delays but cannot prevent completely the progressive erosion of chromosome termini, postponing growth arrest. In this regard, replicative senescence corresponds to G1 growth arrest triggered by shortening of telomeres beyond a critical length (Kim et al. (2002) Oncogene, Vol. 21:503-511; Campisi (2005) Cell, Vol. 120:513-522). Therefore, the telomere-telomerase system controls the mitotic clock and the power of hCPCs to form de novo myocardium. Defects in cardiomyogenesis (Leri et al. (2003) EMBO J, Vol. 22:131-139) are present in telomerase null mice but whether these rodent CPCs are not effective in promoting cardiac repair is not known. Alterations in telomerase activity and telomere length oppose lodging and migration of progenitor cells (Flores et al. (2005) Science, Vol. 309:1253-1256; Flores et al. (2006) Curr Opin Cell Biol, Vol. 18:254-260; Siegl-Cachedenier et al. (2007) J Cell Biol, Vol. 179:277-290) and the derived myocyte progeny could have a limited capacity to divide and form functionally competent contracting cells.

Telomere length in hCPCs has been measured in control, acutely infarcted hearts and in hearts explanted from patients undergoing cardiac transplantation for end-stage ischemic cardiomyopathy (Chimenti et al. (2003) Circ Res, Vol. 93:604-613). Additionally, telomere length has been obtained in myocytes from aging human hearts in the presence or absence of heart failure (Urbanek et al. (2005) Proc Natl Acad Sci USA, Vol. 102:8692-8697). From these data, severe telomeric shortening is apparent in hCPCs of failing hearts. Thus, telomere length can be employed to identify the hCPC pool that possesses the highest long-term repopulating capacity for the damaged heart. The length of telomeres is a good predictor of the regenerative potential of a cell (Weng et al. (1998) Immunity, Vol. 9:151-157; Yang et al. (2001) Mech Ageing Dev, Vol. 122:1685-1694; and Honda et al. (2001) Clin Immunol, Vol. 99:211-221). The growth behavior of transplanted bone marrow cells can be predicted by their telomere length. In fact, hematopoietic regeneration following bone marrow transplantation is less efficient if the repopulating cells have short telomeres (Lincz et al. (2004) Bone Marrow Transplant, Vol. 34:439-445). Cycling hCPCs express the telomerase protein and display telomerase activity (Chimenti et al. (2003) Circ Res, Vol. 93:604-613; Urbanek et al. (2005) Proc Natl Acad Sci USA, Vol. 102:8692-8697; and Urbanek et al. (2003) Proc Natl Acad Sci USA, Vol. 100:10440-10445).

Consistent with our observations obtained in the failing heart of senescent Fischer 344 rat (Example 3) and FVB mice (Torella et al. (2004) Circ Res, Vol. 94:514-524), the telomere-telomerase axis is expected to be impaired in hCPCs of old human beings. To assess the growth potential of hCPCs and establish the effects of culture conditions and population doublings on hCPC function, we have measured telomerase activity and telomere length in hCPCs. This analysis was performed to define whether hCPCs rapidly reach cellular senescence in culture or whether cells can be expanded to clinically relevant numbers before irreversible growth arrest is acquired. For this purpose, nuclei of hCPCs were obtained at P3-P4, P5-P6, and P8-P9 which correspond respectively to 9-12, 15-18, and 25-28 population doublings (PDs), respectively. Nuclei were stained with a peptide-nucleic-acid telomere probe conjugated with fluorescein-isothiocyanate; lymphoma cells with known short (L5178Y-S cells, 7 kbp) and long (L5178Y-R cells, 48 kbp) telomeres were employed for comparison and reference point (Bearzi et al. (2007) Proc Natl Acad Sci USA, Vol. 104:14068-14073; Urbanek et al. (2005) Proc Natl Acad Sci USA, Vol. 102:8692-8697; Chimenti et al. (2003) Circ Res, Vol. 93:604-613; and Leri et al. (2003) EMBO J, Vol. 22:131-139). From P3-P4 to P5-P6, average telomere length decreased 12%, from 9.3 to 8.2 kbp, and from P3-P4 to P8-P9 average telomere length decreased 26% from 9.3 to 6.9 kbp (FIGS. 52B and C). Importantly, average telomere length in human cells is approximately 9.0 kbp (Notaro et al. (1997) Proc Natl Acad Sci USA, Vol. 94:13782-13785). From P3 to P9 there were ~18 PDs with an average telomeric shortening of 130 bp per PD. This accounted for a total loss of 2.4 kbp. This rate of telomere attrition is comparable to that commonly found in human bone marrow hematopoietic stem cells (Van Ziffle et al. (2003) Stem Cells, Vol. 21:654-660).

Critical telomere length associated with cellular senescence and irreversible growth arrest of human hematopoietic stem cells and most likely of hCPCs varies from 2.0 to 1.5 kbp (Van Ziffle et al. (2003) Stem Cells, Vol. 21:654-660). Therefore, the fraction of hCPCs with critical telomeric shortening increased from 1% at P3-P4 to 2% at P5-P6 and 5% at P8-P9. However, following ~25-28 PDs at P8-P9, 69% hCPCs had telomere length ≧5.0 kbp. It can be predicted that cells at P8-P9 can undergo 23 additional PDs (5−2=3 kbp/0.13 kbp=23 PDs) before the occurrence of replicative senescence and irreversible growth arrest. Thus, ~50 PDs can result in the formation of $1 \times 10^{15}$ hCPCs before replicative senescence is reached.

Telomerase activity was measured by the TRAP assay in hCPCs obtained at different passages at P3-P4, P5-P6, and P8-P9 (FIG. 52A). Products of telomerase activity start at 50 by and display a 6-bp periodicity. Samples treated with RNase were used as negative controls, and HeLa cells were used as positive controls. Two protein concentrations were employed to validate the specificity of the reaction. The band at 36 bp corresponds to an internal control for PCR efficiency. Although telomerase activity decreased ~50% from P3-P4 to P8-P9, telomerase activity was still present at these late passages, pointing to a significant growth reserve of hCPCs. Therefore, hCPCs with long telomeres can be extensively grown in vitro and implanted in vivo prior to a major loss in their expansion potential.

Example 7

Expression of Growth Factor Receptor Systems Correlates with Human Cardiac Stem Cell Regenerative Capacity Human cardiac progenitor cells (hCPCs) possess two growth factor receptor systems which can have distinct effects on progenitor cell behavior: the renin-angiotensin system (RAS) and the insulin-like growth factor-1/insulin-like growth factor-1 receptor (IGF-1-IGF-1R) system. The transcripts of each of the components of the RAS and IGF-1-IGF-1R growth factor systems were detected in expanded hCPCs (P5-P6) by real-time RT-PCR (FIG. 53, panels A-C,H,K,L). In each case, 5 ng cDNA was used with the exception of renin that required 15 ng. cDNA was combined with SYBR Green master mix (LightCycler Fast Start DNA Master SYBR Green I, Roche) and cycling conditions were as follows: 95° C. for 10 min followed by 45 cycles of amplification (95° C. denaturation for 10 sec, annealing for 5 sec and 72° C. extension for 20 sec). To avoid the influence of genomic contamination, forward and reverse primers for each gene were located in different exons. Reactions containing cDNA generated without reverse transcriptase and reactions with primers alone were also included. PCR efficiency was evaluated using a standard curve of four serial dilution points. Quantified values were normalized against the input determined by the housekeeping gene β-actin. The expected molecular weight of RT-PCR products was confirmed by gel electrophoresis. In addition, as shown in FIG. 53 (panels D-G,I,J,M,N), the cellular distribution of the components of the RAS and IGF-1-IGF-1R systems was evaluated by immunostaining and confocal microscopy as previously described (Bearzi et al. (2007) Proc Natl Acad Sci USA, Vol. 104:14068-14073; Gonzalez et al. (2008) Circ Res, Vol. 102:597-606). Similar observations have been made in rodent (See Example 2; Urbanek et al. (2005) Circ Res, Vol. 97:663-673) and canine (Linke et al. (2005) Proc Natl Acad Sci USA, Vol. 102:8966-8971) CPCs, strengthening the relevance of the cellular RAS and IGF-1-IGF-1R in the modulation of progenitor cell function.

A. The IGF-1-IGF-1R Growth Factor System

It is likely that the local IGF-1-IGF-1R system plays a critical role in protecting the growth and survival of hCPCs, since a series of studies have shown that IGF-1 exerts powerful growth promoting and anti-apoptotic effects on cardiac and skeletal muscle progenitor cells. In transgenic mice, locally acting IGF-1 targeted to skeletal muscle enhances muscle growth and differentiation, prevents age-related muscle atrophy, and potentiates regeneration following injury (Musaro et al. (2004) Proc Natl Acad Sci USA, Vol. 101: 1206-1210; Schulze et al. (2005) Circ Res, Vol. 97:418-426). Similarly, cardiac restricted expression of IGF-1 increases the formation of ventricular myocytes, improves cell mechanical behavior, attenuates myocyte death, and delays the development of an aging myopathy (Torella et al. (2004) Circ Res, Vol. 94:514-524; Reiss et al. (1996) Proc Natl Acad Sci USA, Vol. 93:8630-8635; Redaelli et al. (1998) Circ Res, Vol. 82:594-603). IGF-1 induces division of CPCs, upregulates telomerase activity, hinders replicative senescence, and preserves the pool of functionally-competent CPCs in transgenic mice (Linke et al. (2005) Proc Natl Acad Sci USA, Vol. 102:8966-8971; Torella et al. (2004) Circ Res, Vol. 94:514-524; Urbanek et al. (2005) Circ Res, Vol. 97:663-673). Following skeletal muscle injury, IGF-1 promotes the activation, mobilization, and differentiation of satellite cells which contribute to muscle regeneration (Musaro et al. (2004) Proc Natl Acad Sci USA, Vol. 101:1206-1210). Heart failure leads to a catabolic state with loss of skeletal muscle mass (Levine et al. (1990) N Engl J Med, Vol. 323:236-241; Anker et al. (1997) Circulation, Vol. 96:526-534) and IGF-1 counteracts this process (Schulze et al. (2005) Circ Res, Vol. 97:418-426). Similarly, cardiac overexpression of IGF-1 attenuates the effects of myocardial infarction (Li et al. (1997) J Clin Invest, Vol. 100:1991-1999; Nagoshi et al. (2005) J Clin Invest, Vol. 115: 2128-2138), coronary constriction (Li et al. (1999) Circ Res, Vol. 84:1007-1019), dilated cardiomyopathy (Welsh et al. (2002) Circ Res, Vol. 90:641-648), and diabetes (Kajstura et al. (2001) Diabetes, Vol. 50:1414-1424; Norby et al. (2004) J Endocrinol, Vol. 180:175-182). IGF-1 decreases cell death and enhances cell regeneration, which act to attenuate the extent of injury and determine the degree of structural and functional recovery.

The short lifespan in lower organisms such as *C. elegans* and *Drosophila* is linked to the loss of regenerative capacity of somatic tissues in adulthood (Maier et al. (2004) Genes Dev, Vol. 18:306-319). Dying cells cannot be replaced and this results in a rapid and progressive decline in organ function. Conversely, cell turnover by activation and commitment of resident progenitor cells remains active in mammals, and old damaged cells that accumulate with time can be replaced by new, younger, better functioning cells. IGF-1 potentiates cell turnover and regeneration in susceptible cells including CPCs (See Example 2; Linke et al. (2005) Proc Natl Acad Sci USA, Vol. 102:8966-8971; Torella et al. (2004) Circ Res, Vol. 94:514-524; Urbanek et al. (2005) Circ Res, Vol. 97:663-673). Myocardial regeneration mediated by IGF-1 activation and growth of CPCs delays the onset of heart failure and its complications in mammals (See Example 3; Linke et al. (2005) Proc Natl Acad Sci USA, Vol. 102:8966-8971; Torella et al. (2004) Circ Res, Vol. 94:514-524; 2, 49, 50). In fact, restoration of IGF-1 level in elderly individuals has health benefits (Carter et al. (2002) Trends Genet, Vol. 18:295-301).

One possible effect of the IGF-1-IGF-1R growth factor system on hCPCs is the attenuation of free radicals that lead to oxidative stress and cellular aging. To test this possibility, we measured the generation of superoxide anion (Redox-Senso Red CC-1) by two-photon microscopy in freshly isolated mouse CPCs cultured in serum-free medium alone or with IGF-1 (100 ng/ml). Mitochondria were simultaneously recognized by MitoTracker Green and two-photon images confirmed the mitochondrial localization of superoxide anion. IGF-1 decreased dramatically the formation of superoxide anion. Mitochondrial superoxide anion was decreased approximately 64% in mouse CPCs exposed to IGF-1 compared to mouse CPCs in serum-free medium.

We also measured the baseline formation and hydrogen peroxide (100 μM)-induced formation of hydroxyl radicals in freshly isolated mouse CPCs in the absence and in the presence of IGF-1. IGF-1 significantly reduced both the baseline formation and hydrogen peroxide-induced formation of hydroxyl radicals. The results of these experiments suggest that the IGF-1-IGF-1R system plays an important role in the prevention of cellular senescence.

Collectively, these findings suggest that the expression of IGF-1R is critical for the preservation of the proliferative capacity of hCPCs. Importantly, the presence of IGF-1R can be employed to sort hCPCs from the pool of senescent cells and evaluate their respective growth and differentiation potential in vitro and in vivo. In support of this notion, we isolated hCPCs that were either positive or negative for IGF-1R expression from both young and old patients and measured their growth and differentiation ability in vitro.

From each hCPC preparation, c-kit-positive hCPCs at P1 were sorted according to the expression of IGF-1R using a FACSAria cell sorter (Becton Dickinson). Subsequently, telomere length was determined by Q-FISH as described in Example 1B to establish a direct relationship between the IGF-1R epitope and the length of telomeres in these hCPC subsets. Several parameters, including percentage of cycling cells, population doubling time (PDT), timing of the cell cycle, accumulation of senescent cells and telomere shortening with serial divisions, and changes in telomerase activity with replication, were analyzed to determine the ability of hCPC classes to divide and differentiate in vitro. To measure the fraction of cycling and non-cycling cells, IGF-1R-positive hCPCs and IGF-1R-negative hCPCs were plated at a low density (100 cells per cm$^2$), and BrdU (1 μg/ml) was added to the medium three times a day for one week. Cells were fixed and BrdU incorporation was determined by immunocytochemistry as previously described (Example 1; Urbanek et al. (2005) Circ Res, Vol. 97:663-673). In view of the long labeling period, BrdU positive and negative cells were considered cycling and non-cycling hCPCs, respectively.

As shown in FIG. 54, hCPCs strongly positive for IGF-1R appear to have a significantly greater rate of division as measured by BrdU incorporation than hCPCs negative for this receptor. In the cases analyzed, there was no actual difference in the growth behavior of IGF-1R-positive hCPCs obtained from young and old failing hearts. Although the compartment of senescent hCPCs was larger in failing than in non-failing hearts (Urbanek et al. (2005) Proc Natl Acad Sci USA, Vol. 102:8692-8697), a population of young c-kit-positive IGF-1R-positive hCPCs was isolated from decompensated hearts and found to possess a remarkable growth reserve.

Figure 55:
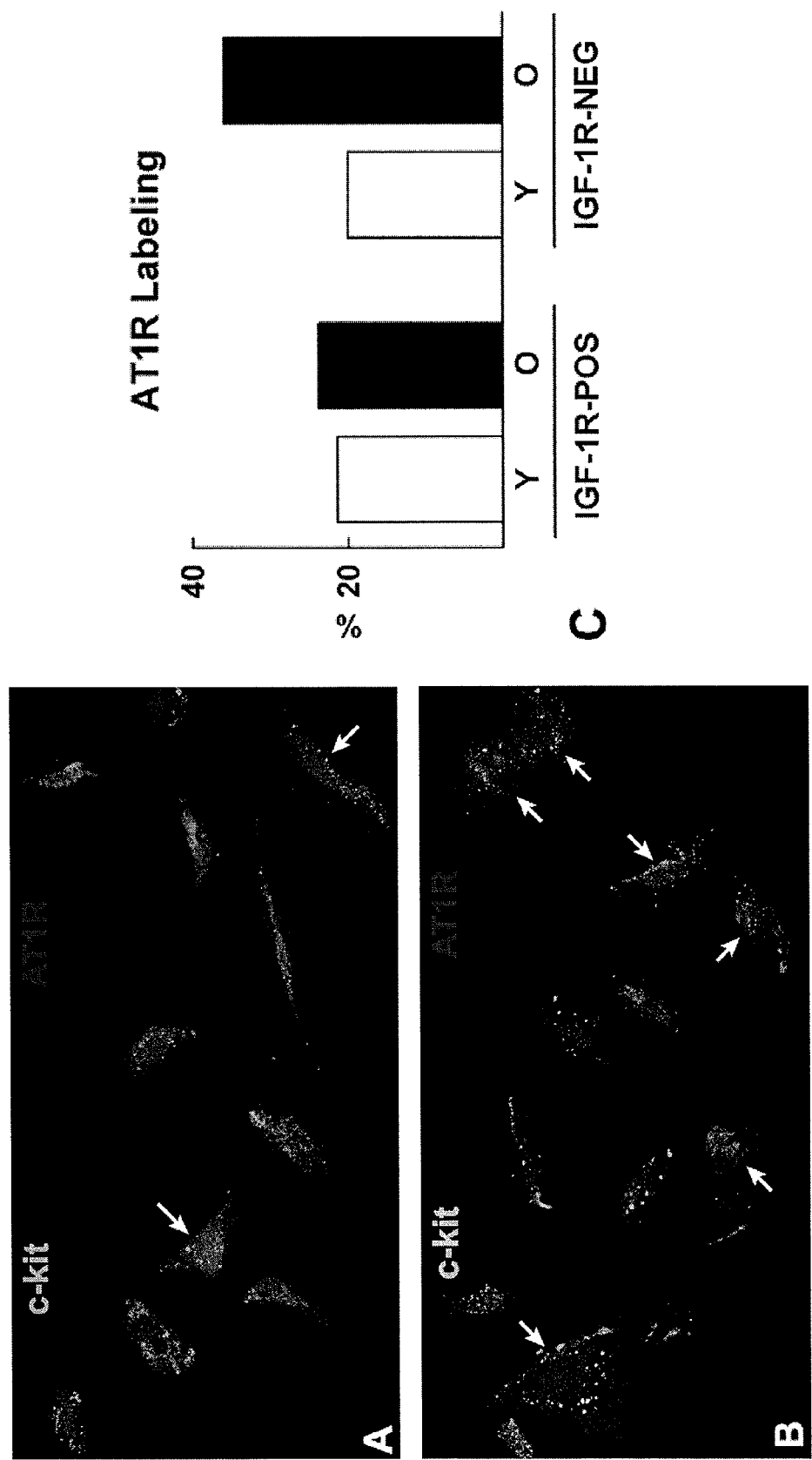
FIG. 55. Localization of AT1 receptors (AT1R; red, arrows) in IGF-1R-positive (A) and IGF-1R-negative (B) hCPCs isolated from an old patient. Green: c-kit. C: Distribution of AT1 receptor in IGF-1R-positive and IGF-1R-negative hCPCs obtained from young (Y) and old (O) patients.

The intact ability of IGF-1R-positive hCPCs to divide was contrasted by the low level of proliferation of IGF-1R-negative hCPCs, which was typically accompanied by upregulation of the expression of angiotensin 1 (AT1) receptors (FIG. 55). These data suggest that RAS may play a role in hCPC senescence and death. RAS has been implicated in senescence of rodent CPCs (see Example 2) in which chronological age is characterized by enhanced expression of the various components of the RAS together with the formation of Ang II in old cells providing evidence in favor of the role of this octapeptide in CPC growth arrest and apoptosis. Ang II may be a significant contributor of the age-dependent accumulation of oxidative damage in the heart (Kajstura et al. (2001) Diabetes, Vol. 50:1414-1424). Inhibition of Ang II positively interferes with heart failure and prolongs life in humans (O'Meara et al. (2007) Circulation, Vol. 115:3111-3120). Ang II generates reactive oxygen species (ROS) and sustained oxidative stress may exceed the cell DNA repair process. The most prominent form of DNA damage induced by free radicals is 8-OH-dG which was demonstrated in CPCs exposed to Ang II (Example 2) or in the chronically failing heart (Chimenti et al. (2003) Circ Res, Vol. 93:604-613). The oxidized nucleotide, 8-OH-dG, increases significantly with Ang II and more in old than in young CPCs; 8-OH-dG tends to accumulate at the GGG triplets of telomeres resulting in telomeric shortening and uncapping (Kawanishi and Oikawa (2004) Ann NY Acad Sci, Vol. 1019:278-284), and loss of telomere integrity is the major determinant of cellular senescence and death. Conversely, IGF-1 interferes with the generation of ROS (Kajstura et al. (2001) Diabetes, Vol. 50:1414-1424), decreases oxidative stress in the aging myocardium (Torella et al. (2004) Circ Res, Vol. 94:514-524), and repairs oxidative DNA damage by homologous recombination (Yang et al. (2005) Am J Physiol, Vol. 289:F1144-F1152).

B. Repair of Damaged Myocardium with Igf-1R Positive Human Cardiac Stem Cells

The objective of these studies is to determine the therapeutic efficacy of IGF-1R-positive long-telomere hCPC subsets in vivo acutely after infarction in immunodeficient rats (condition 1). Similarly, the therapeutic efficacy of IGF-1R-negative short-telomere hCPC subsets in vivo acutely after infarction is also tested (condition 2). The results of these experiments will establish a correlation between IGF-1R expression and regenerative capacity of hCPCs.

Human CPCs are isolated from human myocardial tissue samples from patients undergoing cardiac surgery. C-kit positive hCPCs are further characterized by expression of IGF-1R as described in part A above. Subsets of hCPCs will be selected based on their growth characteristics in vitro. For example, hCPCs that are positive for IGF-1R and exhibit optimal growth rates are selected for administration to infarcted animals in condition 1. hCPCs that are negative for IGF-1R and exhibit low proliferative rates are selected for administration to infarcted animals in condition 2. Prior to administration, the selected subsets of hCPCs are labeled with EGFP by lentiviral infection as previously described (Bearzi et al. (2007) Proc Natl Acad Sci USA, Vol. 104: 14068-14073).

Myocardial infarction is induced in anesthetized female immunodeficient rats. Shortly after coronary occlusion, two injections of ~15,000 EGFP-labeled hCPCs each are made at the opposite sites of the border zone. Animals are exposed to BrdU and sacrificed one month after infarction and cell implantation.

Animals are followed by echocardiography biweekly. Echocardiography is performed in slightly anesthetized rats (ketamine) using a Philips Sonos 5500 equipped with a linear transducer (15-6L). The anterior chest area is shaved and two-dimensional (2D) images and M-mode tracings are recorded from the parasternal short axis view at the level of the papillary muscles. From M-mode tracings, anatomical parameters in diastole and systole and fractional shortening of the posterior wall are determined. Ejection fraction (EF) is derived from left ventricle (LV) cross-sectional area in 2D short axis view: EF=[(LVDA-LVSA)/LVDA]*100 where LVDA and LVSA correspond to LV areas in diastole and systole.

One month after myocardial infarction and cell implantation, animals are studied hemodynamically and morphologically. Under anesthesia (chloral hydrate, 300 mg/kg b.w., i.p.), the right carotid artery is cannulated with a microtip pressure transducer (SPR-612, Millar Instruments) connected to an A/D converter (iWorx 214) and a computer system. The catheter is advanced into the left ventricle for the evaluation of the left ventricular pressures and + and − dP/dt. After the collection of hemodynamic data, in animals to be studied morphologically, the heart is arrested in diastole with the intravenous injection of $CdCl_2$ and the myocardium fixed by perfusion of the coronary vasculature with formalin. The LV chamber is kept at a pressure equal to the in vivo measured left ventricular end-diastolic pressure. This procedure is important for the acquisition of anatomical data.

Infarct dimension is obtained by the morphometric analysis of the number of myocytes remaining and lost from the left ventricle inclusive of the interventricular septum. The number of newly generated myocytes and their volume distribution is measured. Moreover, the hypertrophic response in the surviving myocytes is determined. A similar analysis is conducted for the assessment of the newly formed arterioles and capillaries. The vascularization of the spared myocardium is also determined.

Myocytes, endothelial cells and smooth muscle cells are identified by confocal microscopy and labeling of nuclear, cytoplasmic and membrane proteins (Bearzi et al. (2007) Proc Natl Acad Sci USA, Vol. 104:14068-14073). Collagen is detected by collagen type I and type III antibodies. The extent of myocardial reconstitution in terms of number and size of myocytes and degree of vessel formation within the regenerated tissue is determined quantitatively (Linke et al. (2005) Proc Natl Acad Sci USA, Vol. 102:8966-8971; Bearzi et al. (2007) Proc Natl Acad Sci USA, Vol. 104:14068-14073; Urbanek et al. (2005) Circ Res, Vol. 97:663-673). The morphological counterpart of the physiological integration of new myocytes within the injured ventricle is documented by the expression of connexin 43 and N-cadherin. The possibility that cell fusion contributes to myocardial regeneration is also evaluated. Thus, the validity of the in vitro protocols for the selection of the most appropriate subset of cardiac stem cells to be used clinically is established.

C. Role of p53 in Human Cardiac Stem Cell Senescence

Figure 52:
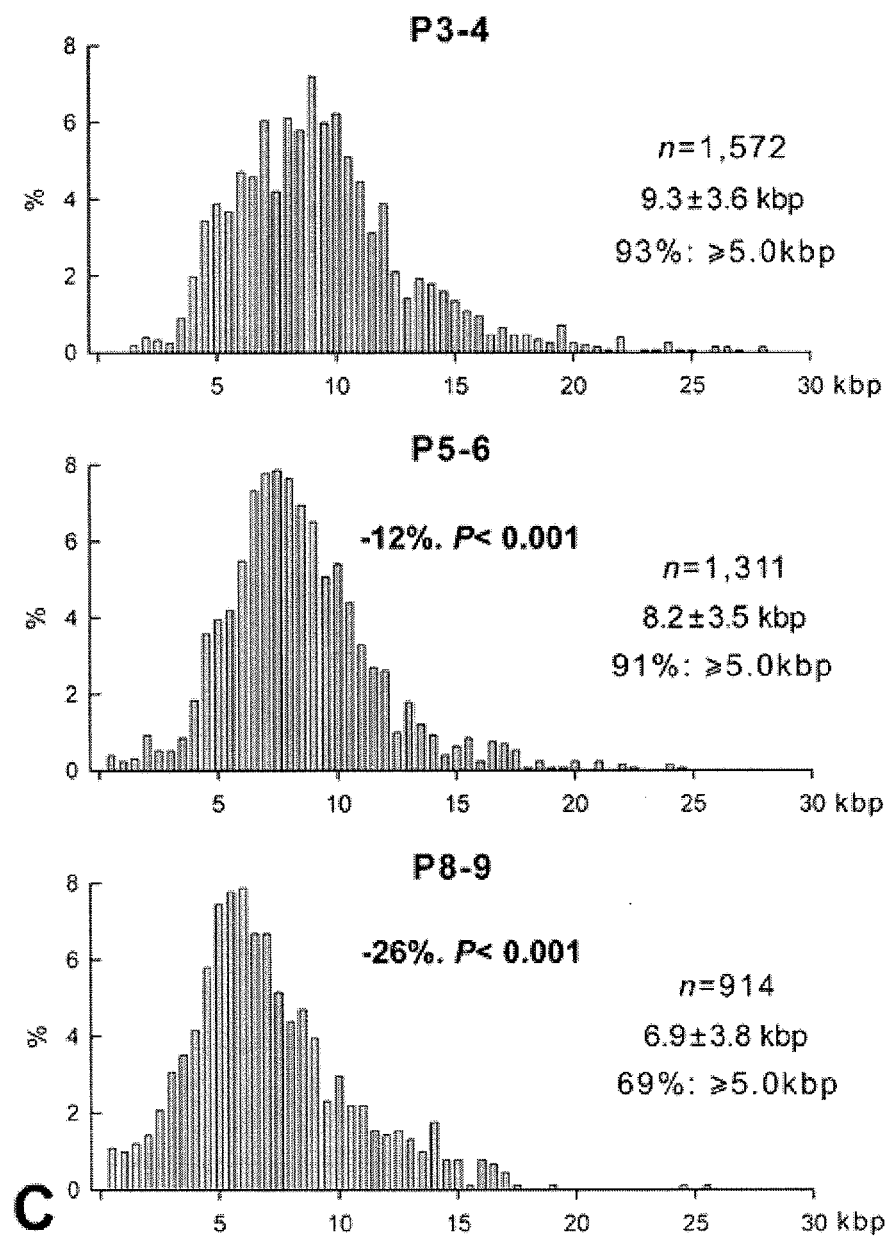
FIG. 52. (A) Telomerase activity in hCPCs. In this assay, hCPCs at P3-P4, P5-P6 and P8-P9 were analyzed. These passages correspond to 9-12, 15-18 and 25-28 population doublings. Products of telomerase activity start at 50 bp and display a 6-bp periodicity. Two protein concentrations were employed. Samples treated with RNase and CHAPS buffer were used as negative controls and HeLa cells as a positive control. The band at 36 bp corresponds to an internal control for PCR efficiency. Telomerase activity decreased nearly 50% from P3-P4 to P8-P9. (B) Telomere length in cardiac PCs. These images were obtained in hCPCs at P3-P4, P5-P6 and P8-P9. Magenta dots represent individual telomeres. Lymphoma cells with short (7 kbp, L5178Y-S) and long (48 kbp, L5178Y-R) known telomere length were used for comparison and reference point. (C) Distribution of telomere lengths in hCPCs at different passages. The average telomere length is indicated together with the degree of telomeric shortening and the fraction of cells with telomeres equal to or longer than 5 kbp.

To date, the most reliable marker of cellular senescence is the telomere-telomerase system (Kim et al. (2002) Oncogene, Vol. 21:503-511; Campisi J (2005) Cell, Vol. 120:513-522; and Yang et al. (2001) Mech Ageing Dev, Vol. 122:1685-1694). Telomerase activity is present in the normal adult human heart and is increased in myocardial hypertrophy (Urbanek et al. (2003) Proc Natl Acad Sci USA, Vol. 100:10440-10445), acute and chronic ischemic cardiomyopathy (Urbanek et al. (2005) Proc Natl Acad Sci USA, Vol. 102:8692-8697) and premature myocardial aging (Chimenti et al. (2003) Circ Res, Vol. 93:604-613). This ribonucleoprotein, however, does not prevent telomere erosion; severe telomeric shortening has been detected in both myocytes and hCPCs of the failing human heart (Urbanek et al. (2005) Proc Natl Acad Sci USA, Vol. 102:8692-8697; Chimenti et al. (2003) Circ Res, Vol. 93:604-613; and Urbanek et al. (2003) Proc Natl Acad Sci USA, Vol. 100:10440-10445) These observations are consistent with results obtained in hematopoietic stem cells (HSCs). HSCs express low to moderate levels of telomerase, but telomeres shorten considerably with age (Notaro et al. (1997) Proc Natl Acad Sci USA, Vol. 94:13782-13785). Two possibilities have been proposed to explain telomeric shortening in the presence of detectable telomerase activity: a suppressor of telomerase function may be operative during the cell cycle or a competition may occur between the reassembly of telomeric chromatin and extension of telomeres by telomerase (Notaro et al. (1997) Proc Natl Acad Sci USA, Vol. 94:13782-13785). In a manner similar to HSCs, telomere shortening in hCPCs occurs at a rate of ~130 bp per population doubling (FIG. 52). Chronic cardiac decompensation and aging lead to an imbalance between telomerase activity and length of telomeres in hCPCs, resulting in critical telomeric shortening, growth arrest and cellular senescence (Urbanek et al. (2005) Proc Natl Acad Sci USA, Vol. 102:8692-8697; Chimenti et al. (2003) Circ Res, Vol. 93:604-613). The presence of hCPCs with these characteristics has profound consequences on ventricular function.

Telomeres of intact length form loop structures that conceal the end of chromosomes (Griffith et al. (1999) Cell, Vol. 97:503-514). When telomeres shorten, T- and D-loops collapse and telomeres are perceived by the cells as sites of DNA damage (Griffith et al. (1999) Cell, Vol. 97:503-514; Greider CW (1999) Cell, Vol. 97:419-422; and Yang et al. (2005) Mol Cell Biol, Vol. 25:1070-1080). The double-stranded TTAGGG repeats become too short to bind telomere binding proteins and form T-loops, and the single-stranded 3' overhang is unable to form D-loops (Griffith et al. (1999) Cell, Vol. 97:503-514; Greider C W (1999) Cell, Vol. 97:419-422). The accumulation of multiple checkpoint proteins at the level of short telomeres indicates that dysfunctional telomeres trigger a DNA damage response in which the major player is the transcription factor p53 (Stansel et al. (2002) J Biol Chem, Vol. 277:11625-11628). The ataxia-telangiectasia mutated (ATM) protein kinase is required for the phosphorylation of p53 at serine 15 (Celli and de Lange (2005) Nat Cell Biol, Vol. 7:712-718). This event activates a cascade of post-translational modifications of p53 which result in transcription of p53 target genes followed by activation of the apoptotic program or the onset of cellular senescence. P53 phosphorylation at serine 15 is accompanied by enhanced expression of p21Cip1 to promote, if possible, DNA repair (Campisi J (2005) Cell, Vol. 120:513-522). Thus, p53 modulates growth arrest, apoptosis and senescence through the upregulation of specific proteins, including p21Cip1, Bax and Bad (Selivanova and Wiman (2005) Adv Canc Res, Vol. 66:143-180; Levine A J (1997) Cell, Vol. 88:323-331). Bax and Bad are implicated in apoptosis while high levels of p21Cip1 trigger irreversible growth arrest and cellular senescence. $P16^{INK4a}$ rarely co-localizes with DNA double-strand breaks (Herbig et al. (2004) Mol Cell, Vol. 14: 501-513); $p16^{INK4a}$ represents a delayed response which follows the induction of p53 and p21Cip1 (Jacobs and de Lange (2005) Cell Cycle, Vol. 4:1364-1368).

In cardiomyocytes, p53 acts as a transcription factor for the components of the myocyte RAS (Pierzchalski et al. (1997) Exp Cell Res, Vol. 234:57-65; Leri et al. (1998) Circulation, Vol. 97:194-203; Leri et al. (1998) J Clin Invest, Vol. 101: 1326-1342; Leri et al. (1999) Am J Pathol, Vol. 154:567-580; Leri et al. (1999) Circ Res, Vol. 84:752-762; Leri et al. (2000) Am J Pathol, Vol. 157:843-857; and Fiordaliso et al. (2001) Diabetes, Vol. 50:2363-2375) and a similar function of p53 is postulated to be operative in hCPCs. The promoter regions of Aogen and AT1 receptor contain consensus binding sites for p53. The regulation of Aogen by p53 is particularly relevant since the availability of the Aogen substrate represents the limiting step in the biosynthesis of Ang II. Moreover, the increased synthesis and release of Ang II in hCPCs may produce a prolonged stimulation of AT1 receptors creating a positive feedback loop that sustains hCPC apoptosis or senescence. The continuous secretion of Ang II with AT1 receptor activation triggers, in turn, the phosphorylation of the C-terminus of p53 at serine 390 by PKC and p38-MAPK (Fiordaliso et al. (2001) Diabetes, Vol. 50:2363-2375). This post-translational modification upregulates p53 function together with the transcription of p53-dependent (Bax, Bad, p21Cip1) and p53-regulated (Aogen, AT1 receptor) genes. Importantly, inhibition of p53 prevents the synthesis of Ang II, p53 and p38 MAP kinase phosphorylation and cell death. Similarly, the AT1 receptor blocker losartan prevents phosphorylation of p53 and p38 MAP kinase induced by Ang II (Fiordaliso et al. (2001) Diabetes, Vol. 50:2363-2375). Additionally, inhibition of p38 MAP kinase mimics at a more distal level the consequences of losartan by preventing Ang II-mediated myocyte death (Fiordaliso et al. (2001) Diabetes, Vol. 50:2363-2375).

The prevailing function of p53 on the IGF-1-IGF-1R system consists of the downregulation of IGF-1R expression by inhibition of transcription (Werner et al. (1996) Biochemistry, Vol. 93:8318-8323; Prisco et al. (1997) Mol Cell Biol, Vol. 17:1084-1092; and Girnita et al. (2000) Cancer Res, Vol. 60:5278-5283) or by formation of a complex between the receptor and Mdm2 which leads to enhanced ubiquitination and degradation of IGF-1R (Girnita et al. (2003) Proc Natl Acad Sci USA, Vol. 100: 8247-8252). Also, IGF-1 stimulation leads to phosphorylation of the amino-terminal of p53 and phosphorylated p53 upregulates Mdm2 (Leri et al. (1999) Am J Pathol, Vol. 154:567-580; Leri et al. (1999) Circ Res, Vol. 84:752-762) which, in turn, may degrade IGF-1R (Girnita et al. (2003) Proc Natl Acad Sci USA, Vol. 100: 8247-8252). Importantly, increased p53 activity has been linked to decreased IGF-1 production in epithelial organs (Gatza et al. (2008) Dev Biol, Vol. 313:130-141). Moreover, the p53-target gene PTEN acts as phosphatase on PIP3 opposing Akt phosphorylation (Levine et al. (2006) Genes Dev, Vol. 20:267-275) and IGF-1 cellular responses.

IGF-1 inhibits p53 via the upregulation of Mdm2 and the formation of Mdm2-p53 inactive protein complexes ultimately decreasing the synthesis of Ang II and p53 function (Leri et al. (1999) Am J Pathol, Vol. 154:567-580; Leri et al. (1999) Circ Res, Vol. 84:752-762). A major downstream effector of IGF-1 is Akt which phosphorylates the N-terminus of p53 leading to the selective transcription of the mdm2 gene (Ashcroft et al. (2000) Mol Cell Biol, Vol. 20:3224-3233; Haupt Y (2004) Cell Cycle, Vol. 3:884-885). Residues 16-28 of the p53 alpha-helical peptide bind to the hydrophobic pocket of Mdm2 (Chen et al. (2005) Mol Cancer Ther, Vol. 4:1019-1025) forming a protein-to-protein complex. Mdm2 represses p53 function by sequestering the transcription factor in the nucleolar compartment, decreasing its half-life and inhibiting its DNA binding activity (Stommel and Wahl (2005) Cell Cycle, Vol. 4:411-417; Vousden and Prives (2005) Cell, Vol. 120:7-10). As a consequence of the generation of Mdm2-p53 inactive complexes, the anti-apoptotic and anti-aging effects of IGF-1 on hCPCs may be mediated by downregulation of the local RAS. Collectively, these findings suggest that senescence of hCPCs may depend on the imbalance between RAS, on the one hand, and IGF-1, on the other.

Another important aspect concerns the relationship between telomerase and p53. Although p53 cannot bind directly to the promoter of the catalytic subunit of telomerase (TERT), p53 represses TERT expression by two mechanisms. P53 can form a complex with Sp1 which is no longer available for the activation of the TERT promoter (Kusumoto et al. (1999) Clin Cancer Res, Vol. 5: 2140-2147; Kanaya et al. (2000) Clin Cancer Res, Vol. 6:1239-1247; Xu et al. (2000) Oncogene, Vol. 19: 5123-5133; and Shats et al. (2004) J Biol Chem, Vol. 279: 50976-50985). Additionally, p53 inhibits TERT transcription through the induction of p21Cip1 which favors the accumulation of the hypophosphorylated pocket protein Rb (Helmbold et al. (2006) Oncogene, Vol. 25:5257-5262). Activated Rb stably suppresses TERT via the assembly of repressive E2F-Rb protein complexes on the promoter of TERT (Shats et al. (2004) J Biol Chem, Vol. 279: 50976-50985; Won et al. (2004) Proc Natl Acad Sci USA, Vol. 101:11328-11333). Thus, the local RAS downregulates telomerase while IGE-1 upregulates telomerase through the modulation of p53 function. Importantly, IGF-1 may phosphorylate telomerase in hCPCs through the PI3K-Akt pathway. We have identified a consensus site for Akt phosphorylation, RVRLRELSQE (amino acids 585 to 594; SEQ ID NO.: 23), in the mouse telomerase (Torella et al. (2004) Circ Res, Vol. 94:514-524) and a similar sequence is present in human TERT (Kang et al. (1999) J Biol Chem, Vol. 274: 13085-13090), suggesting that IGF-1 upregulates telomerase and, thereby, hCPC growth and survival, delaying cellular aging.

Based on these observations, we test the hypothesis that the growth and survival of hCPCs is regulated by the telomere-telomerase system which through p53 function controls the activity of the local RAS and IGF-1-IGF-1R pathway conditioning hCPC senescence and death.

Human CPCs are isolated from myocardial tissue samples obtained from patients with overt heart failure by enzymatic dissociation and sorting with a rabbit c-kit antibody (Santa Cruz Biotechnology). Sorted cells are expanded (P5-P6) in F12 medium supplemented with 5-10% FBS and insulin-selenium-transferrin mixture. From each hCPC preparation, cells are further sorted according to the expression of IGF-1R and AT1 receptors. Pellets of hCPCs are quickly frozen in liquid nitrogen and stored at −80° C. for molecular analysis.

To analyse the different growth factor receptor systems present in the isolated hCPCs, sorted hCPCs at P5-P6 are cultured in serum-free medium (SFM) to measure IGF-1 and Ang II secretion. Additionally, cultures are stimulated with IGF-1 (human recombinant IGF-1 150 ng/ml) or Ang II ($10^{-11}$ mol/L) for a period of 24 hours to detect whether a positive feedback loop is involved in growth factor production. Media containing the growth factors is removed and cells washed twice. Fresh SFM is added. The SFM contains antibodies against IGF-1R (Abcam) or the AT1 receptor antagonist losartan ($10^{-7}$M) and the AT2 receptor blocker PD123319 ($10^{-7}$ mol/L, Sigma). The blockers are employed to avoid ligand binding. Media is collected after 3, 9, 15 and 24 hours for IGF-1 and Ang II measurement. Growth factor quantities are determined by ELISA (IGF-1, R&D Systems; Ang II, Peninsula) and normalized by the total quantity of hCPC proteins and β-actin expression measured by Western blotting. In addition, the expression of angiotensinogen (Aogen), Renin, Cathepsin, angiotensin converting enzyme (ACE), ACE2, Chymase, AT1 receptor, AT2 receptor, IGF-1 and IGF-1R is determined by real-time RT-PCR, Western blotting and immunocytochemistry. It is expected that cellular senescence will correlate with a downregulation of the IGF-1-IGF-1R system and upregulation of the RAS system.

The next series of experiments examines the expression and activity of the Telomere-Telomerase System in the isolated hCPCs. To assess the expression of the catalytic subunit of telomerase and telomere related proteins, nuclear extracts are obtained by incubation of sorted hCPCs in hypotonic and hypertonic buffers. Proteins are either immunoprecipitated with telomerase reverse transcriptase (TERT) antibody and detected by Western blotting (for detection of telomerase catalytic subunit) or loaded on 8-10% SDS/PAGE, transferred onto nitrocellulose and exposed to specific antibodies against TRF-1 and TRF-2 (detection of telomere related proteins). Telomerase corresponds to a 120-125-kDa band. HeLa cells are used as positive control (Leri et al. (2001) Proc Natl Acad Sci USA, Vol. 98:8626-8631).

Telomerase activity is assessed by TRAP assay. Sorted hCPCs are homogenized in CHAPS buffer and centrifuged at 4° C. One to five μg of untreated and RNase-treated hCPC extracts are incubated with [γ32P]ATP-end-labeled telomerase substrate (TS oligonucleotide: 5'-AATCCGTCGAG-CAGAGTT-3' SEQ ID NO.: 1), Taq polymerase and anchored reverse primer (3'-GCGCGC[CTTACC]3CTAACC-5', SEQ ID NO.: 19) for 30 min. Samples are exposed to 27 amplification cycles. Telomere Length is measured by two approaches in IGF-1R-positive and AT1 receptor-positive hCPCs. The first approach consists of telomeric restriction fragment (TRF) analysis. In this approach, hCPCs are incubated overnight with the restriction enzymes RsaI and HinfI. Digested DNA fragments are run in 1% agarose gel with 0.5X TBE buffer. Gels are prehybridized in 5× Denhardt's solution, 5× sodium chloride/sodium citrate buffer, 0.1% SDS and 20 mM $NaH_2PO_4$ for 5 h at 55° C. A 32P-labeled probe of 1.6 kb containing the sequence $(TTAGGG)_n$ is added and hybridized. Gels are washed and exposed to film. Cell lines with known telomeric length are utilized for comparison. Southern blot hybridization results in a smear of telomeric fragments of varying size providing an estimation of the average telomeric length in the entire cell population (Kang et al. (1999) J Biol Chem, Vol. 274:13085-13090). The second approach involves the Q-FISH technique and is described in Example 1.

Telomerase Phosphorylation will be assessed by two different assays. The first assay, the Akt protein kinase assay, assesses the activity of the upstream kinase (Akt) that phosphorylates telomerase. This assay is performed in accordance to the protocol of the PepTag non-radioactive protein kinase C (PKC) assay system 11 (Promega, Madison, Wis.). For Akt kinase substrates, fluorescein-conjugated H2B histone (30RKRSRKESYS39, SEQ ID NO.: 20) and hTERT (817AVRIRGKSYV826, SEQ ID NO.: 21) oligopeptides are employed (Peptron). Nuclear extracts are obtained by incubation of sorted hCPCs in hypotonic and hypertonic buffers. Five μg of fluorescein oligopeptide are incubated with 10 μl of lysates in 20 μl of protein kinase reaction mixture (20 mM HEPES, pH 7.2, 10 mM $MgCl_2$, 10 mM $MnCl_2$, 1 mM dithiothreitol, 0.2 mM EGTA, 20 μM ATP, 1 μg phosphatidylserine, protein kinase activator) at 30° C. for 30 min. Reactions are stopped by heating at 95° C. for 10 min. The phosphorylated peptide is separated on 0.8% agarose gel at 100 V for 15 min. The phosphorylated negatively charged substrates migrate to the anode. The second assay detects the presence of phosphorylated human TERT. hCPC lysates are prepared using HNTG buffer (20 mM HEPES, pH 7.5; 150 mM NaCl; 0.1% Triton X-100; and 10% glycerol) and then incubated with anti-TERT (H-231, Santa Cruz) overnight. Immunoprecipitated proteins are washed with ice-cold HNTG buffer and subject to immunoblotting with anti-phospho-(Ser)-Akt-substrate (Cell Signaling). This antibody recognizes proteins containing the Akt consensus site containing phospho-Ser preceded by Arg at position −3 and −5(RXRXXS, SEQ ID NO.: 22). hCPCs that exhibit high proliferative capabilities are expected to have longer telomeres, higher telomerase activity, and more phosphorylated telomerase compared to hCPCs that have poor growth characteristics. In addition, IGF-1R expression is expected to correlate with high proliferative ability and longer telomeres, while AT1 receptor expression is expected to correlate with low proliferative ability and shorter telomeres.

The next series of experiments assesses the role of p53 in cellular sensescence of hCPCs. p53 and respective kinase phosphorylation are examined in preparations of sorted hCPCs by separating protein lysates (30-50 μg) on 10% SDS-PAGE, transferring separated proteins to nitrocellulose, and exposing the nitrocellulose to phospho-Ser390-p53 antibody and phospho-Ser15-p53 antibody, ATM protein kinase antibody, phospho-p38 MAP kinase antibody and phospho (Ser473)-Akt antibody, at a concentration of 1-2 μg/ml in TBST. The expression of hypophosphorylated Rb is also measured. The expression of p53-target genes, Bax, Mdm2, PTEN and p21Cip1, is determined by Western blotting. The formation of complexes between p53 and Mdm2, and p53 and Sp1 is detected by immunoprecipitation and Western blotting. Specifically, three separate immunoprecipitation assays are performed: Protein extracts are incubated overnight at 4° C. with 3 μg of mouse monoclonal anti-p53 (Pab 240, Santa Cruz) and 250 μl of HNTG buffer. Subsequently, 50 μl of protein A—agarose is added. After washing, samples are centrifuged at 14,000 rpm for 2 minutes. Immunoprecipitated proteins are separated on 10% SDS-PAGE, transferred onto nitrocellulose filters and exposed to rabbit polyclonal anti-Mdm2 (C-18 and K-20, Santa Cruz) or anti-Sp1 (Abcam) at a concentration of 1 μg/ml. The supernatant obtained from this immunoprecipitation is immunoprecipitated again with anti-p53 (Pab 240, Santa Cruz) and then exposed to rabbit polyclonal anti-p53 (FL-393, Santa Cruz) to obtain the amount of non-bound p53.

To evaluate the activity of p53 in sorted hCPCs, the transcriptional activity of p53 is evaluated by two approaches. The first approach employs an electrophoretic mobility shift assay. Consensus binding sites for p53 in the promoter region of the Aogen, AT1 receptor, Bax, p21Cip1 and IGF-1 receptor are utilized to design oligonucleotides for use in the assay. [γ32ATP]-labeled oligonucleotides are employed in bandshift assays, which are performed in sorted hCPCs cultured in the presence and absence of Ang II, IGF-1, losartan, PD123319 or IGF-1 blocking antibody. Nuclear extracts are obtained by exposing cells to hypotonic and hypertonic buffers and are incubated with excess of unlabeled self-oligonucleotide and p53-antibody. The second approach involves chromatin immunoprecipitation. To map the location of p53 on the promoters of Aogen, AT1 receptor, Bax, p21Cip1 and IGF-1 receptor specific genes, formaldehyde-cross-linked DNA is fragmented by sonication and pulled down with p53 antibodies. Immunoprecipitated chromatin is recovered and the cross-linking reversed. The promoter regions of the genes of interest are recognized by PCR. Senescence of hCPCs is expected to correlate with upregulation of p53 function.

Example 8

Human Cardiac Stem Cells with Immortal DNA have Superior Regenerative Capacity

Current understanding of stem cell self-renewal has recently been perturbed by the resurrection of an old theory proposed 35 years ago (Cairns (1975) Nature, Vol. 255:197-200). It has been suggested that stem cells may cosegregate the original template DNA strands ("oldest") in consecutive divisions so that the daughter cell that inherits the old DNA retains stem cell features, while the daughter cell that acquires the new DNA enters the transit amplifying pool. The non-random segregation of the immortal DNA strands opposes the accumulation of mutations resulting from non-repaired replication errors and prevents partly telomere shortening during cell division (Cairns (1975); Potten et al. (2002) N. Cell. Sci., Vol. 115: 2381-2388; Falconer et al. (2010) Nat. Protoc., Vol. 5: 1362-1377). The applicability of this concept to hematopoietic and other stem cells has been challenged (Kiel et al. (2007) Nature, Vol. 449:238-242) and arguments against this mechanism of stem cell division have been purported (Lansdorp (2007) Cell, Vol. 129: 1244-1247).

If the immortal strand hypothesis is correct, the number of mother stem cells has to be genetically determined in each organ sometime early in life and this cell class cannot be expanded thereafter. Conversely, this category of "true" stem cells may decrease dramatically as a result of environmental factors, oxidative stress and disease processes which are commonly present with the progression of life in humans. However, cardiac stem cells (CSCs) retaining the old DNA would represent the most powerful stem cell pool able to repopulate the damaged heart. The documentation that the human myocardium contains CSCs which divide according to the immortal DNA strand hypothesis would provide strong evidence in favor of the notion that the human heart is a self-renewing organ in which tissue homeostasis and repair is regulated by a compartment of resident CSCs.

A. Human CSCs Divide by Asymmetric and Symmetric Chromatid Segregation

The approach required to discriminate random from non-random DNA template segregation during division of human CSCs (hCSCs) is complex; in vivo studies in humans cannot be performed and the primitive or committed state of stem cells cannot be definitely ascertained in any system in vivo (Kiel et al. (2007); Lansdorp (2007)). The ancient "grandparent" DNA cannot be targeted by exogenously delivered thymidine analogs and the co-existence of old and newly synthesized labeled "parent" DNA is lost in the second generation (Potten et al. (2002); Falconer et al. (2010); Karpowicz et al. (2005) J. Cell. Biol., Vol. 170: 721-732; Shinin et al. (2006) Nat. Cell. Biol., Vol. 8: 677-687; Conboy et al. (2007) PLoS. Biol., Vol. 5: e102; Rando (2007) Cell, Vol. 129: 1239-1243), making it impossible to follow in vivo the destiny of hCSCs carrying the immortal DNA.

The division of hCSCs by non-random and/or random segregation of chromatids can only be documented by clonal assay of bromodeoxyuridine (BrdU) tagged hCSCs. This protocol underscores at the stem cell level, i.e., clonogenicity, whether clonal cells formed by division of BrdU-positive parent hCSCs with the old DNA show only one BrdU-labeled cell (newly synthesized strands of parent DNA) while all other hCSCs in the clone are BrdU-negative, being the descendants of the mother cell retaining the entire DNA template. In contrast, clones formed by division of hCSCs with random segregation of chromatids are expected to be composed of cells that are all BrdU-positive, although dilution of BrdU occurs with clonal expansion.

Figure 56:
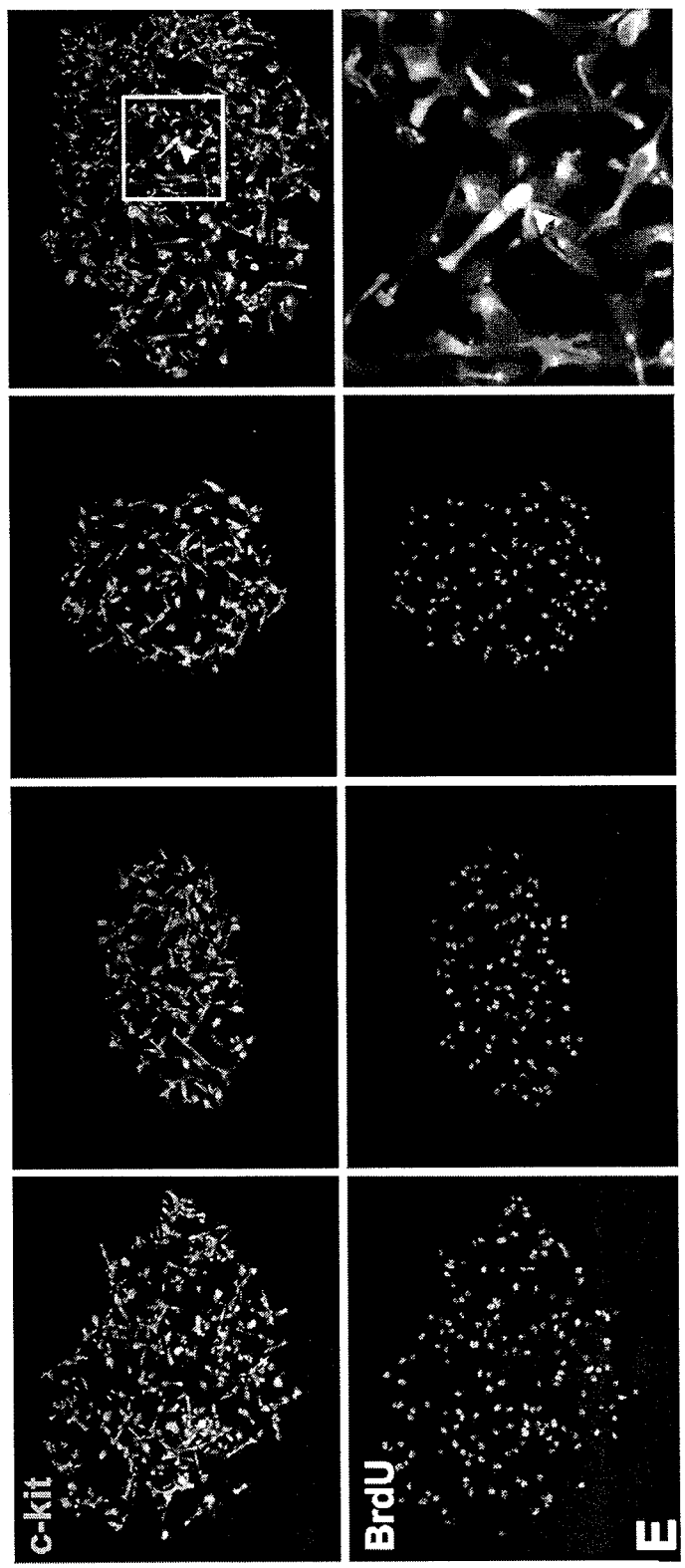
FIG. 56. Human cardiac stem cells (hCSCs) were isolated and expanded in vitro in the absence of BrdU and then exposed to BrdU for ~5-6 population doublings until nearly 100% "grandparent hCSCs" were BrdU-positive (99.5±1.0%). Then, these cells divided generating a pool of "parent hCSCs" also positive for BrdU (A). BrdU-labeled parent hCSCs were plated at limiting dilution (B) to generate clones according to the pattern of chromatid segregation (C, D). In 3 of 4 representative clones (E), all hCSCs were labeled by BrdU, while, in the fourth clone, hCSCs were all negative for BrdU with the exception of one cell.

Lineage negative c-kit-positive hCSCs were collected from 16 human myocardial samples as previously described in detail (Bearzi et al. (2007) Proc. Natl. Acad. Sci. U.S.A., Vol. 104: 14068-14073). Subsequently, the length of the cell cycle of these hCSCs (n=6) was determined by the labeled mitosis method (Baserga, Ed. The Biology of Cell Reproduction, Harvard University Press, Cambridge Mass/Longdon England, 1985) and found to be 26±3 hours (FIG. 59A). Based on this parameter, lineage negative c-kit-positive hCSCs were exposed to BrdU for a period of ~5-6 population doublings until nearly 100% "grandparent hCSCs" were BrdU-positive (99.5±1.0%) Then, these cells divided generating a pool of "parent hCSCs" also positive for BrdU (FIG. 56A). BrdU-tagged hCSCs were then plated at limiting dilution, less than 1 cell/cm$^2$, or deposited in individual wells of Terasaki plates at a density of 0.25-0.5 cells/well (FIG. 56B). Wells containing more than one cell were excluded. An average 13,000 hCSCs were seeded per patient; collectively, 1,281 clones were obtained, reaching a clonal efficiency of 0.6% (FIGS. 57A and B). Clonal efficiency was independent from age and the duration of the cardiac disease.

Of the 1,281 clones, 77 were characterized by BrdU-labeling of a single hCSC (FIGS. 56C and E) and 1,204 by BrdU-labeling of all clonal cells (FIGS. 56D and E), indicating that 6% of founder hCSCs divided carrying the original DNA template, while 94% replicated carrying only newly synthesized DNA. Thus, hCSCs appear to consist of two cell classes which self-renew by non-random and random segregation of chromatids, although the latter predominates. In the 16 patients, the percentage of hCSCs retaining the old DNA was inversely related to age while coronary artery disease, aortic stenosis and their duration did not influence the relative proportion of hCSCs with old and new DNA.

B. Cellular Senescence and Extensive Growth do not Affect the Pattern of HCSC Division One critical variable to be dealt with to prove or disprove the non-random chromatid segregation model of hCSC division involved the characterization of the single cells that retained BrdU in 6% of the clones. Three possibilities were considered (Lansdorp (2007)): a) Individual BrdU-positive cells could have reached growth arrest and replicative senescence early in the formation of the clones, being unable to generate clonal cells with progressive dilution of the label; b) Non-senescent BrdU-labeled sister cells could be responsible for the generation of clones with progressive dilution of BrdU which became undetectable by immunolabeling; and c) Dividing BrdU-positive hCSCs together with replicating BrdU-negative cells could result in the formation of "mixed" clones composed of BrdU-negative and BrdU-positive hCSCs.

Forty clones containing each only one BrdU-positive cell were labeled for p16$^{INK4a}$; the presence of the senescence-associated protein p16$^{INK4a}$ prevents the reentry of stem cells into the cell cycle permanently (Janzen et al. (2006) Nature, Vol. 443: 421-426; Molofsky et al. (2006) Nature, Vol. 443: 448-452; Krishnamurthy et al. (2006) Nature, Vol. 443: 453-457). In these clones, both BrdU-positive and BrdU-negative clonal cells did not express p16$^{INK4a}$ (FIG. 58A), excluding that the cells that inherited the labeled new DNA reached irreversible growth arrest. Both the individual cell in each clone that retained the old DNA and other cells that contained the new DNA did not undergo cell cycle withdrawal.

To collect supportive evidence that clonal cells were actually the product of rounds of division of hCSCs with the old DNA rather than the product of an extreme level of dilution of the thymidine analog with cell replication, BrdU-labeled parent hCSCs (see FIG. 56A) were loaded with quantum dots (Qdots) and plated. This protocol was implemented to determine whether cells which lost BrdU and retained the immortal DNA strands underwent several divisions that markedly reduced Qdots labeling in the cytoplasm; 14 clones containing each one BrdU-positive cell were analyzed. The intensity of Qdot fluorescence in the clonal BrdU-negative hCSCs decreased in proportion to the number of divisions while the 14 BrdU-positive hCSCs retained a large quantity of Qdots (FIG. 58B). Additionally, examples of clones consisting of a combination of cells carrying and non-carrying BrdU were never encountered in all clones examined. Thus, the non-random chromatid segregation model of hCSC division does not involve the acquisition of the senescent phenotype of the singularly BrdU labeled cells, the lack of replication of cells retaining the old DNA or the concurrent contribution of dividing BrdU-positive and BrdU-negative hCSCs to clonal expansion.

An important aspect of the immortal DNA strand hypothesis and the recognition that the human heart possesses two pools of hCSCs, which during replication segregate differently the old and new DNA, required the acquisition of direct morphological evidence of these distinct mechanisms of DNA partitioning. For this purpose, c-kit-positive hCSCs were exposed to BrdU for ~36 hours to allow them to incorporate the halogenated nucleotide. BrdU was then removed and a chasing period of ~30 hours was introduced so that hCSCs could traverse one cell cycle in the absence of BrdU. At the end of this period, cells were fixed and the distribution of BrdU in mitotic anaphase images was examined. In most cases, both sets of anaphase chromosomes were labeled by BrdU, documenting random chromatid segregation. However, in a limited number of mitotic cells, BrdU was detected only in one set of anaphase chromosomes which was consistent with the non-random chromatid segregation during cell division (FIGS. 59C and D).

To document further that a subset of hCSCs divides by non-random segregation of chromatids, chlorodeoxyuridine (CldU) labeled parent hCSCs were plated for clonal analysis. Subsequently, iododeoxyuridine (IdU) was added for the duration of the cell cycle, ~26 hours, to identify newly synthesized DNA strands in the first generation of two cells derived from the CldU labeled parent hCSCs. IdU was then removed from the culture and the analysis of DNA strands in the second cell generation was performed following a chasing period of ~26 hours. By this approach, clones of 3 cells were found in which one cell was positive for CldU and IdU, one cell was positive for IdU only, and one cell was negative for both CldU and IdU (FIG. 59B). The latter cell retained the old DNA while the other two contained the new DNA.

C. hCSCs Carrying the Immortal DNA have Greater Growth Reserve

Figure 61:
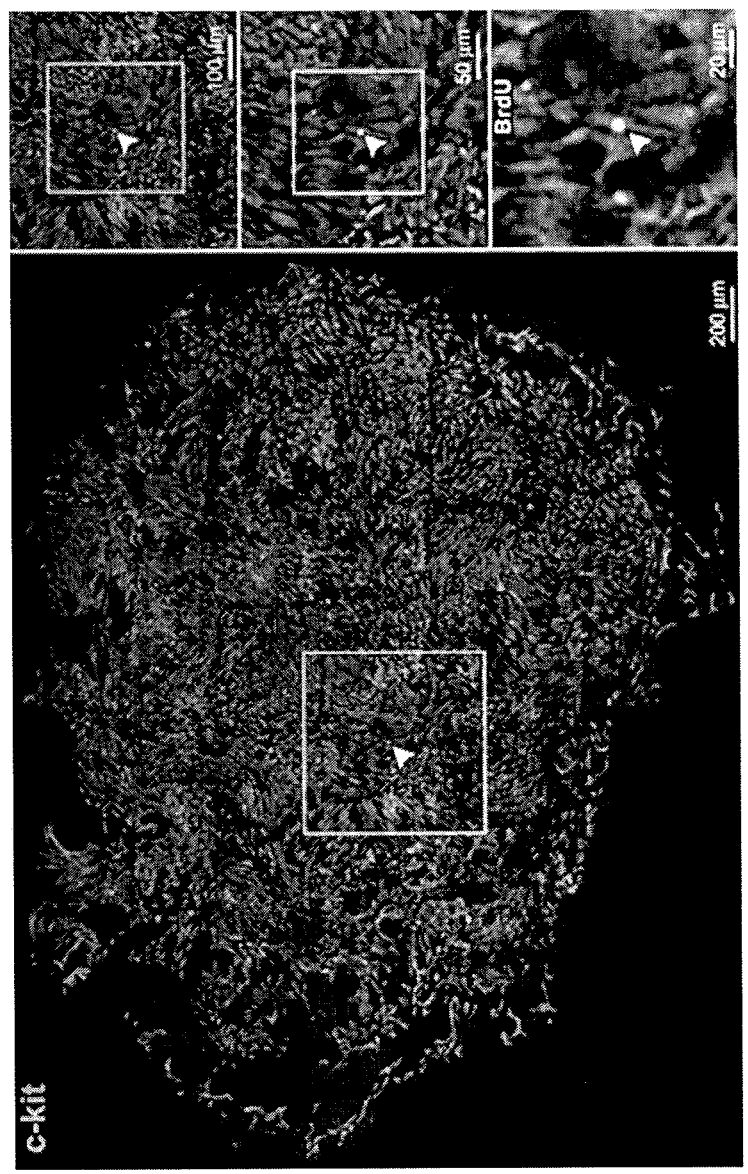
FIG. 61. A single BrdU-labeled "parent" hCSC (green) generated a clone of ~10,000 c-kit-positive cells in which only one cell was BrdU-positive. The "parent" BrdU-labeled DNA was lost after the second division. Rectangles delimit at higher magnification the cell that retained BrdU (white, arrowheads).

Based on the assumption that the growth reserve of stem cells possessing the old DNA is theoretically superior to that of stem cells inheriting only the newly synthesized DNA, the size and age of the clonal progeny derived from these two classes of hCSCs was determined. This quantitative analysis was conducted in 7 patients and included 105 clones generated by non-random and 135 clones formed by random segregation of chromatids. During the initial 7 days, developing clones consisting of a maximum of 300 cells per clone were analyzed. The number of cells present in the clones derived from hCSCs with old DNA was 1.6-fold higher than that found in clones generated by hCSCs with new DNA (FIGS. 60A-D and F). The enhanced rate of cell generation observed with hCSCs dividing by non-random chromatid segregation was consistent with a 23% shorter population doubling time of this cell pool (FIG. 60E). Importantly, the difference in the size of the clones increased with time. At 12 days, hCSCs with old DNA formed clones 2.2-fold larger than those obtained with hCSCs carrying the new DNA. Although clonal cells developed by hCSCs retaining the immortal DNA experienced a larger number of divisions, only 3 $p16^{INK4a}$-positive cells were detected in 105 clones. Conversely, $p16^{INK4a}$ labeling accounted for 2% of clonal cells generated by replication of hCSCs with random chromatid segregation (FIG. 60H). A single BrdU-labeled "parent" hCSC generated a clone of ~10,000 c-kit-positive cells in which only one cell was BrdU-positive (FIG. 61).

Importantly, telomere length measured by Q-FISH varied from 7 to 10 kbp and from 2.0 to 9 kbp in cells derived from hCSCs carrying the old and new DNA, respectively. In both hCSC classes, telomere length was inversely related to the age of the heart. Additionally, small colonies/clones consisting of 30 cells or less in which all cells expressed $p16^{INK4a}$ were restricted to division of hCSCs with new DNA; 40 such examples were encountered in the 1,204 generated clones. No senescent clones were found in the 105 obtained from replication of hCSCs with the old DNA. The clones generated by hCSCs with the old DNA were significantly larger and were composed of clonal cells which were all $p16^{INK4a}$-negative and expressed IGF-1 receptors. Conversely, some of the clones formed by hCSCs with the new DNA were very small and at times the clonal cells were uniformly $p16^{INK4a}$-positive and lacked IGF-1 receptors. Thus, hCSCs carrying the immortal DNA constitute a pool of powerful progenitors with a high degree of growth reserve.

D. Linear and Exponential Growth of hCSCs

The findings discussed above raised some challenging questions. The linear growth to be expected by hCSCs carrying the immortal DNA, and the exponential growth experienced by hCSCs with the newly synthesized DNA was inconsistent with the size of the clones formed by these cell categories. In fact, an opposite result was obtained. The possibility was considered that, early in the process, a smaller number of clonal cells had to be generated by hCSCs with the old DNA and, subsequently, a daughter cell containing only the newly synthesized DNA did not enter growth arrest but created a progeny which grew exponentially. Based on the data collected at 7 and 12 days after plating of hCSCs for clonal assay, the time at which both types of clones were of equal size was computed and found to be 4 days. Therefore, a change in the pattern of growth of hCSCs carrying the immortal DNA had to occur over a 4 day period. Our previous experiments suggested that linear expansion of hCSCs with old DNA was preserved during the first division of CldU-labeled "parent" cells, ~26-30 hours after seeding, pointing to 2 and 3 days as the critical intervals for a shift in cell division, i.e., from linear to exponential growth.

To characterize the mechanisms of cell growth in clones originated by hCSCs with old and new DNA, the number of cells developed by each stem cell was determined as a function of time. Four days after seeding, both cell classes showed exponential growth, although the rate of cell replication was higher in clones derived from hCSCs possessing immortal DNA. When data were plotted on a logarithmic scale, the line had an exponential and a linear segment that intersected at day 4.

Clones were made and the properties of clonal cells at 2, 3 and 6 days after plating were determined to establish their fate: cell cycle arrest, linear growth and exponential growth. CldU labeled "parent" hCSCs were seeded in single wells of Terasaki plates. Twenty-four hours later, when 2 cells in each well were present, IdU was added for 24 hours. Clones were then allowed to expand up to 6 days. Clonal cells made by hCSCs dividing by random segregation of chromatids showed an identical pattern at 2, 3 and 6 days; all cells within the clones were positive for CldU and IdU. Additionally, these cells were negative for the cell cycle inhibitor p53 and were positive for the cell cycle proteins Ki67 and MCM5, documenting exponential growth. In a manner similar to the hematopoietic system, p53 was employed as a marker of cell quiescence (Liu et al. (2009) Cell. Stem. Cell, Vol. 4: 37-48;

van Os et al. (2009) Cell. Stem. Cell, Vol. 4:7-8). A combination of Ki67 and MCM5 was used because these proteins together cover the various phases of the cell cycle (Scholzen and Gerdes (2000) J. Cell. Physiol., Vol. 182: 311-322; Bell and Dutta (2000) Annu. Rev. Biochem., Vol. 71: 333-374).

A complex pattern of cell behavior was found in clones obtained from hCSCs dividing by non-random segregation of chromatids. At day 2, the clones consisted of 3 cells: the cell carrying the immortal DNA was negative for CldU and p53, but contained IdU and expressed Ki67-MCM5; the other 2 cells were positive for p53 and were labeled by CldU or IdU. At day 3, the clones consisted of 4 cells: the cell with the old DNA was negative for CldU, IdU and p53, but expressed Ki67-MCM5; 2 cells were positive for p53 and were labeled by CldU or IdU; and one cell was negative for CldU and p53, but was positive for IdU and Ki67-MCM5. This cell reflected the daughter cell generated by division of the IdU-positive "mother" stem cell which did not enter the quiescent state and began to grow exponentially. In fact, at 6 days, clones consisted of 14 cells: 8 cells, representing the exponentially expanded population, showed diluted IdU labeling and were negative for p53 and positive for Ki67-MCM5; 2 cells expressed p53 and were either CldU or IdU positive; 3 cells were negative for CldU, IdU and Ki67-MCM5, but expressed p53; and, finally, one cell carrying the immortal DNA was Ki67-MCM5 positive and negative for CldU, IdU and p53. Thus, these clones were the result of linear growth of hCSCs retaining the immortal DNA and exponential growth of one hCSC carrying the newly synthesized DNA, which escaped growth inhibition after the third division.

Larger clones, at 12 days, maintained a similar behavior. Ki67 identified cycling cells with the new DNA which were responsible for the generation of the majority of clonal progeny. Ki67-MCM5-negative cells constituted the clonal cells derived from linear growth of the hCSC with the old DNA which expressed p53 and entered growth arrest. Importantly, p53 was detected in all quiescent cells negative for Ki67-MCM5, pointing to this tumor suppressor as the mechanism of growth arrest in cells containing the newly synthesized DNA. The p53-positive hCSCs expressed 53BP1 and Rad51 which are markers of non-homologous end joining mediated DNA repair (Huertas (2010) Nat. Struct. Mol. Biol., Vol. 17:11-16), suggesting that the non-dividing daughter cells carrying new DNA reacted to DNA damage by activating an error-prone DNA repair response (Mohrin et al. (2010) Cell. Stem. Cell., Vol. 7: 174-185). 53BP1 and Rad51 were not detected in the cells growing exponentially in the clones derived from hCSCs with the new DNA. Collectively, these observations suggest that the immortal strand hypothesis of stem cell self-renewal is operative in a class of progenitors of the human heart.

E. Progeny Formed by hCSCs Dividing by Asymmetric Chromatid Segregation

The notion that non-random segregation of chromatids during stem cell division results necessarily in the formation of a daughter stem cell with the old DNA and a daughter "committed" cell with the new DNA (Cairns (1975); Potten et al. (2002); Falconer et al. (2010); Karpowicz et al. (2005); Rando (2007)) is debatable. This pattern of cell growth excludes symmetric cell division and the possibility that stem cells can expand rapidly their pool or create a large progeny by the generation of two daughter stem cells or two daughter differentiating cells (Morrison and Kimble (2006) Nature, Vol. 441:1068-1074). Therefore, we determined whether clones formed by single hCSCs which contain the old DNA were actually composed by only one true stem cell (old DNA) and a cluster of committed cells (new DNA). Small aliquots of clonal cells were examined to establish the absence or presence of BrdU labeling in these cell subsets; clones derived from non-random DNA template segregation contained none or at most one BrdU-positive cell and clones formed by random DNA template segregation consisted of all BrdU-positive cells.

Both classes of clonogenic cells were then analyzed by FACS and found to express in less than 1% transcription factors and cytoplasmic proteins specific of myocytes, ECs and SMCs. These results tend to exclude the lineage commitment of clonogenic cells containing the new DNA whether derived from hCSCs which divided by non-random or random DNA template segregation. Similar data were collected by immunolabeling of clonal cells formed by hCSCs that divided by non-random chromatid segregation; all clonal cells were largely negative for the NRx2.5 and GATA4. These data suggest that asymmetric segregation of chromatids during division of hCSCs does not form a committed progeny and cannot be equated to asymmetric stem cell division but rather to symmetric stem cell division.

To support further this view, clonal cells were sub-cloned to acquire an additional characterization of the role of asymmetric chromatid segregation during cell division. Again, clones derived from BrdU-labeled parent hCSCs were identified by staining small aliquots of clonal cells for BrdU. The absence of positive cells for the halogenated nucleotide was considered indicative of the formation of clonal cells from non-random DNA template segregation and an appropriate sample for sub-clonal analysis. Therefore, the BrdU-negative clonal cells were deposited at limiting dilution and after cell attachment, BrdU was added for a period of ~26 hours (length of the cell cycle) to label all cycling cells; BrdU was then removed. Only one sub-clone with a single BrdU-positive cell was obtained while all other sub-clones were composed of undifferentiated BrdU-labeled cells. Thus, non-random chromatid segregation reflected symmetric stem cell division with the formation of two daughter stem cells, one with the old and the other with the new DNA.

The mitotic asymmetry of DNA segregation may be conditioned by the components of the spindle body machinery (Neumüller and Knoblich (2009) Genes. Dev., Vol. 23: 2675-2699). Dividing cells may recognize the old kinetochore or centriole, which may be inherited by the "mother" cell, together with the immortal DNA strand (Shinin et al. (2006) Nat. Cell. Biol., Vol. 8: 677-687). The mitotic spindle uses dynamic microtubules and mitotic motors to drive the movements that underlie "search and capture" of chromosomes, and their alignment and segregation (Brunet and Vernos (2001) EMBO. Rep., Vol. 2: 669-673). To understand the molecular basis of the biased segregation of chromatids in hCSCs, we studied the left-right dynein motor protein (LRD) (Armakolas and Klar (2007) Science, Vol. 315:100-101). Mutations of the LRD gene lead to embryonic left-right body axis asymmetry and this phenomenon is mediated by alterations in the modality of cell division (Sapienza (2007) Science, Vol. 315: 46-47). Thus, BrdU-labeled hCSCs were transfected with a plasmid containing siRNA for LRD and EGFP, FACS-sorted for EGFP, and plated at limiting dilution. Control hCSCs were transduced with scrambled siRNA and expressed normal levels of LRD. Nearly 5% of clones generated by control hCSCs showed a single BrdU bright cell, reflecting the expected number of hCSCs dividing by asymmetric chromatid segregation of the founder cell. In contrast, downregulation of LRD in founder hCSCs led to clones formed exclusively by symmetric chromatid segregation, suggesting that LRD may be one of the factors involved in asymmetric segregation of chromatids.

F. Myocardial Regeneration after Infarction

To document the clinical import of hCSCs with the old and new DNA, the approach discussed thus far could not be used. We had to develop a protocol that allowed the identification and collection of a significant number of living hCSCs, of both classes, to be delivered in vivo to infarcted hearts. This novel strategy takes advantage of the interaction between the BrdU integrated in the DNA of replicating hCSCs and the fluorescence intensity of DNA dyes (Crissman et al. (1994) Methods. Cell. Biol., Vol. 41: 341-349; Rampal et al. (1997) J. Chromatogr. A., Vol. 781: 357-365). The monomeric cyanine nucleic acid stain TO-PRO-3 intercalates randomly in double DNA strands and when is located next to BrdU-adenosine pairs, the TO-PRO-3 inherent level of fluorescence is dramatically enhanced (Rampal et al. (1997); Beisker et al. (1999) Cytometry, Vol. 37: 221-229). This does not occur with non-intercalating dyes, i.e., propidium iodide (PI), since its fluorescence efficiency is independent from the neighboring nucleotides (Crissman et al. (1994)). If DNA is labeled by both PI and TO-PRO-3, fluorescence resonance energy transfer (FRET) takes place (Beisker et al. (1999); Chan and Holmes (2004) Methods Mol. Biol., Vol. 263: 281-292; Van Wageningen et al. (2006) Cytometry A., Vol. 69: 291-298). This formed the basis for FACS sorting of living hCSCs with old and new DNA, i.e., separation of BrdU-positive cells (new DNA) from BrdU-negative cells (old DNA).

To determine the impact of BrdU incorporation on FRET, hCSCs were exposed to BrdU for ~5-6 population doublings to achieve nearly 100% BrdU labeling. BrdU-positive hCSCs were then labeled with both PI and TO-PRO-3. The presence of BrdU led to a decrease in amplitude of the PI spectrum and to an increase of TO-PRO-3 signal. Following a 36 hour chasing period, which allowed hCSCs with the mother DNA to divide and transfer the newly synthesized BrdU-labeled DNA to one of the daughter cells, BrdU-positive and BrdU-negative hCSCs were FACS-sorted and cultured separately for 5 days to deter mine their population doubling time (PDT); hCSCs with the old DNA had, as shown before, a shorter PDT, consistent with a higher growth rate.

If the enhanced proliferative potential in vitro of the progeny formed by hCSCs with "mother" DNA is preserved in vivo, this cell class can be expected to induce a more powerful level of cardiac repair in the damaged heart. Therefore, the extent of myocardial regeneration promoted by the progeny of hCSCs with the old and new DNA was determined after infarction in immunosuppressed rats (Bearzi et al. (2007); Bearzi et al. (2009) Proc. Natl. Acad. Sci. U.S.A., Vol. 106: 15885-15890). In these in vivo studies, the two categories of hCSCs were prepared by the FACS-FRET protocol described above and infected with a EGFP lentivirus for their subsequent tracking. Ten days after coronary artery occlusion and cell delivery, significant differences were found in the therapeutic efficacy of the progeny of hCSCs with the old and new DNA. The former cell type resulted in a superior degree of tissue reconstitution; the infarct was replaced almost completely by growth and differentiation of this category of hCSCs, a reparative response never seen previously (Bearzi et al. (2007); Beltrami et al. (2003) Cell, Vol. 114: 763-776; Urbanek et al. (2005) Circ. Res., Vol. 97: 663-673; Padin-Iruegas et al. (2009) Circulation, Vol. 876-887 7, 39-42). Wall thickening, number of myocytes formed, and extent of cell replication were all higher with the progeny of hCSCs with the "mother" DNA, with the exception of myocyte size, which was similar in both groups of infarcted animals. Newly formed myocytes expressed connexin 43 and N-cadherin and showed sarcomere striation in the subsarcolemmal region. The number of regenerated arterioles and capillaries was also larger with this cell type. The human origin of the regenerated structures was confirmed by the detection of human DNA sequences with an Alu probe and the specificity of the recorded immunolabeling signals by spectral analysis. Importantly, both hCSC progeny improved the hemodynamic performance of the infarcted heart, although cells derived from hCSCs carrying the immortal DNA showed an additional positive effect. The recovery of systolic pressure and positive and negative dP/dt, and the attenuation in the increase of computed diastolic stress were significantly greater than those obtained with cells formed by hCSCs with new DNA.

G. Discussion

The results described in this Example provide direct evidence that the human heart possesses a small pool of cardiac stem cells that during division retain the old template DNA strands and, following growth inhibition and activation of an error-prone DNA repair response in the daughter cell carrying the newly synthesized DNA, generate two daughter cells, which retain the old and new DNA, respectively. The former undergoes linear growth while the latter experiences exponential growth and may be responsible for the large compartment of hCSCs which replicate in the absence of a selective partitioning of chromatids in the myocardium. However, both hCSC classes possess stem cell characteristics being undifferentiated, self-renewing and clonogenic in vitro and in vivo. These observations support only in part the model of stem cell growth proposed by John Cairns and its implication in terms of the destiny of the daughter cells (Cairns (1975)). According to the immortal strand hypothesis, cells carrying the old DNA templates function as stem cells and preserve the stem cell pool of the organ, while cells containing the newly synthesized DNA strands undergo lineage specification. Thus, asymmetric segregation of chromatids has been considered equivalent to asymmetric stem cell division, but this is not the case. Additionally, our previous findings indicate that hCSCs divide symmetrically and asymmetrically in vitro and in vivo generating daughter cells with identical or divergent fate (Bearzi et al. (2007); Bearzi et al. (2009)). These patterns of hCSC division have been determined based on the localization of the endocytic proteins numb and α-adaptin (Zhong (2003) Neuron, Vol. 37: 11-14) and the function of the Notch receptor (Boni et al. (2008) Proc. Natl. Acad. Sci. U.S.A., Vol. 105: 15529-15534).

The current observations, which underscore some of the shortcomings of Cairns' model of stem cell self-renewal, raise the possibility that each cardiac stem cell niche is composed of a dominant cell carrying the old DNA and a cluster of CSCs containing the new DNA. The brightly BrdU labeled CSC found within each niche structure (Urbanek et al. (2006) Proc. Natl. Acad. Sci. U.S.A., Vol. 103: 9226-9231) most likely corresponds to the BrdU-labeled grandparent CSC which did not divide subsequently. This notion is consistent with the lack of expression of p53, 53BP1 and Rad51 in BrdU-bright CSCs of the mouse heart as described above. Only CSCs formed by random chromatid segregation would leave the niche area and differentiate into functionally competent cardiomyocytes and vascular structures. This pattern of stem cell growth would protect the pool size of grandparent CSCs within the niches. Importantly, the presence of CSCs brightly labeled by the thymidine analog allows the recognition of cardiac niches which contain a true stem cell carrying the immortal DNA that controls the destiny of the less commanding cells.

Human CSCs carrying the immortal DNA strand have long telomeres and generate a large pool of non-senescent cells. This high self-replicating potential exceeds significantly the growth of hCSCs that possess only the newly synthesized DNA, making the former class of stem cells a more desirable progenitor for myocardial regeneration following injury. In fact, the progeny formed by hCSCs with old DNA led to a restoration of the infarcted myocardium which was structurally and functionally superior to that induced by cells derived by hCSCs with new DNA. Replacement of the entire infarcted region of the wall with newly formed cardiomyocytes and coronary vessels was never seen before with cardiac and non-cardiac progenitor cells. The impressive recovery in ventricular hemodynamics and anatomy mediated by clonogenic cells developed from hCSCs carrying the "mother" DNA underscores the clinical relevance of this stem cell category for the management of ischemic and non-ischemic heart failure.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A pharmaceutical composition comprising a population of isolated human adult c-kit positive cardiac stem cells and a pharmaceutically acceptable carrier, wherein at least 50% of said isolated cardiac stem cells have immortal DNA.

2. The composition of claim 1, wherein the cardiac stem cells are IGF-1 receptor positive.

3. The composition of claim 1, wherein the cardiac stem cells have telomeres greater than 5 kbp in length.

4. The composition of claim 3, wherein the cardiac stem cells have telomeres greater than 7 kbp in length.

5. The composition of claim 1, wherein the cardiac stem cells are p16$^{INK4a}$ negative.

6. The composition of claim 1, wherein the cardiac stem cells are isolated from human myocardial tissue.

7. The composition of claim 1, wherein the population is obtained by selecting cardiac stem cells that are bromodeoxyuridine (BrdU) negative following at least one passage of the cells in culture after BrdU labeling.

8. A method of repairing damaged myocardium in a subject in need thereof by administering to the subject a composition of claim 1, wherein the structural and functional integrity of the damaged myocardium is at least partially restored following administration of the composition.

9. The method of claim 8, wherein the isolated adult cardiac stem cells are autologous.

10. The method of claim 8, wherein the composition is administered intramyocardially or intracoronarily.

11. The composition of claim 1, wherein at least 80% of the isolated cardiac stem cells have immortal DNA.

12. The composition of claim 1, wherein the cardiac stem cells are negative for markers of the cardiac, skeletal muscle, neural, and hematopoietic cell lineages.

13. An isolated population of human adult c-kit positive cardiac stem cells, wherein at least 50% of the cardiac stem cells have immortal DNA, and wherein the population is obtained by
labeling human adult c-kit positive cardiac stem cells with a DNA label, culturing the labeled cardiac stem cells for at least one population doubling in the absence of the DNA label, and selecting the cardiac stem cells that are negative for the DNA label.

14. The cell population of claim 13, wherein the DNA label is BrdU, chlorodeoxyuridine (CldU), or iododeoxyuridine (IdU).

15. The cell population of claim 13, wherein the cardiac stem cells are IGF-1 receptor positive and p16$^{INK4a}$ negative.

16. The cell population of claim 13, wherein the cardiac stem cells are negative for markers of the cardiac, skeletal muscle, neural, and hematopoietic cell lineages.

17. The cell population of claim 13, wherein at least 80% of the cardiac stem cells in the population have immortal DNA.

18. The cell population of claim 13, wherein 100% of the cardiac stem cells in the population have immortal DNA.

19. The cell population of claim 13, wherein the cardiac stem cells are isolated from human myocardial tissue.

20. The composition of claim 1, wherein 100% of the isolated cardiac stem cells have immortal DNA.

21. The cell population of claim 13, wherein the cardiac stem cells in the population divide by non-random chromatid segregation when expanded in culture.

* * * * *